(12) United States Patent
Yamanaka et al.

(10) Patent No.: US 7,192,943 B2
(45) Date of Patent: Mar. 20, 2007

(54) CEPHEM COMPOUNDS

(75) Inventors: Toshio Yamanaka, Osaka (JP); Kenji Murano, Osaka (JP); Ayako Toda, Osaka (JP); Hidenori Ohki, Osaka (JP); Masaru Oogaki, Osaka (JP); Shinya Okuda, Osaka (JP); Kohji Kawabata, Osaka (JP); Satoshi Inoue, Akitakata (JP); Keiji Misumi, Akitakata (JP); Kenji Itoh, Akitakata (JP); Kenji Sato, Akitakata (JP)

(73) Assignees: Astellas Pharma Inc., Tokyo (JP); Wakunaga Pharmaceutical Co., Ltd., Osaka (JP)

( * ) Notice: Subject to any disclaimer, the term of this patent is extended or adjusted under 35 U.S.C. 154(b) by 159 days.

(21) Appl. No.: 10/942,916

(22) Filed: Sep. 17, 2004

(65) Prior Publication Data

US 2005/0096306 A1 May 5, 2005

(30) Foreign Application Priority Data

Sep. 18, 2003 (AU) .............................. 2003905084

(51) Int. Cl.
C07D 501/46 (2006.01)
A61K 31/546 (2006.01)
A61P 31/04 (2006.01)

(52) U.S. Cl. ........................... 514/202; 540/222
(58) Field of Classification Search ................ None
See application file for complete search history.

(56) References Cited

U.S. PATENT DOCUMENTS

| | | | | |
|---|---|---|---|---|
| 4,927,818 A | * | 5/1990 | Takaya et al. | 514/202 |
| 4,952,578 A | * | 8/1990 | Sakane et al. | 514/202 |
| 5,109,130 A | * | 4/1992 | Sakane et al. | 540/222 |
| 5,173,485 A | * | 12/1992 | Sakane et al. | 514/202 |
| 5,187,160 A | * | 2/1993 | Sakane et al. | 514/202 |
| 5,194,432 A | | 3/1993 | Takaya et al. | |
| 5,210,080 A | * | 5/1993 | Takaya et al. | 514/202 |
| 5,215,982 A | * | 6/1993 | Sakane et al. | 514/202 |
| 5,302,712 A | * | 4/1994 | Sakane et al. | 540/222 |
| 5,663,163 A | * | 9/1997 | Takaya et al. | 514/202 |
| 2004/0132994 A1 | * | 7/2004 | Ohki et al. | 540/222 |
| 2004/0248875 A1 | * | 12/2004 | Ohki et al. | 514/202 |
| 2005/0004094 A1 | * | 1/2005 | Yamanaka et al. | 514/202 |

FOREIGN PATENT DOCUMENTS

| | | |
|---|---|---|
| EP | 0 047 977 A2 | 3/1982 |
| EP | 0 062 321 A2 | 10/1982 |
| EP | 0 771 803 A1 | 5/1997 |
| EP | 1 134 222 A1 | 9/2001 |
| WO | WO 97/41128 | 11/1997 |
| WO | WO 02/090364 A1 | 11/2002 |
| WO | WO 2004/039814 A1 | 5/2004 |

OTHER PUBLICATIONS

Raymond F. Brown, et al., "Synthesis and Biological Evaluation of a Series of Parenteral 3'-Quaternary Ammonium Cephalosporins", Journal of Medicinal Chemistry, vol. 33, XP-001084083, 1990, pp. 2114-2121.

Kenji Sakagami, et al., "Synthetic Cephalosporins. VI. Synthesis and Antibacterial Activity of 7-[(Z)-2-(2-Aminothiazol-4-yl)-2-(1-carboxy-1-methyl)ethoxyiminoacetamido]-3-(3-hydroxy-4-pyridon-1-yl)methyl-3-cephem-4-carboxylic Acid and Related Compounds", Chem. Pharm. Bull., vol. 38, No. 8, XP-001083825, 1990, pp. 2271-2273.

Derwent Publications, AN 1992-387716, XP-002267713, JP 04-288086, Oct. 13, 1992.

* cited by examiner

*Primary Examiner*—Mark L. Berch
(74) *Attorney, Agent, or Firm*—Oblon, Spivak, McClelland, Maier & Neustadt, P.C.

(57) ABSTRACT

The present invention relates to a compound of the formula [I]:

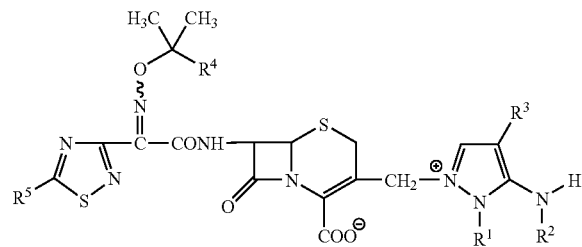

wherein $R^1$ is lower alkyl or hydroxy(lower)alkyl, and
$R^2$ is hydrogen or amino protecting group, or
$R^1$ and $R^2$ are bonded together and form lower alkylene;
R is -A-$R^6$ wherein A is bond, —NHCO—$(CH_2CO)_n$—, lower alkylene, —NH—CO—CO— or the like, and
$R^6$ is

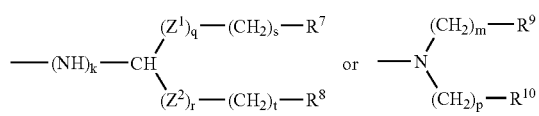

wherein $R^7$, $R^8$, $R^9$ and $R^{10}$ are independently amino, guanidino, amidino or the like;
$R^4$ is carboxy or protected carboxy; and
$R^5$ is amino or protected amino, or a pharmaceutically acceptable salt thereof, a process for preparing a compound of the formula [I], and a pharmaceutical composition comprising a compound of the formula [I] in admixture with a pharmaceutically acceptable carrier.

20 Claims, No Drawings

CEPHEM COMPOUNDS

TECHNICAL FIELD

The present invention relates to new cephem compounds and pharmaceutically acceptable salts thereof. More particularly, the present invention relates to new cephem compounds and pharmaceutically acceptable salts thereof, which have antimicrobial activities, to processes for preparation thereof, to pharmaceutical composition comprising the same, and to a method for treating infectious diseases in human being and animals.

DISCLOSURE OF INVENTION

One object of the present invention is to provide novel cephem compounds and pharmaceutically acceptable salts thereof, which are highly active against a number of pathogenic microorganisms.

Another object of the present invention is to provide processes for the preparation of said cephem compounds and salts thereof.

A further object of the present invention is to provide a pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula [I]:

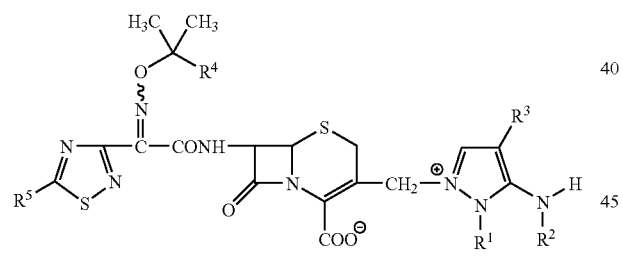

[I]

wherein
$R^1$ is lower alkyl or hydroxy(lower)alkyl, and
$R^2$ is hydrogen or amino protecting group, or
$R^1$ and $R^2$ are bonded together and form lower alkylene;
$R^3$ is -A-$R^6$
   wherein
   A is bond, —NHCO—$(CH_2CO)_n$— wherein n is 0 or 1, lower alkylene, —NH—CO—CO— or

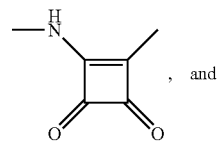

, and $R^6$ is

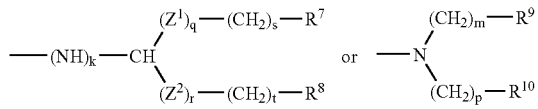

wherein
   $Z^1$ and $Z^2$ are independently —NHCO— or —CONH—,
   k, q and r are independently 0 or 1,
   s and t are independently an integer of 0 to 6,
   m and p are independently an integer of 0 to 6, and
   $R^7$, $R^8$, $R^9$ and $R^{10}$ are independently amino, protected amino, guanidino, protected guanidino, amidino or protected amidino;
$R^4$ is carboxy or protected carboxy; and
$R^5$ is amino or protected amino.

As to the object compound [I], the following points are to be noted.

That is, the object compound [I] includes syn isomer (Z form), anti isomer (E form) and a mixture thereof. Syn isomer (Z form) means one geometrical isomer having the partial structure represented by the following formula:

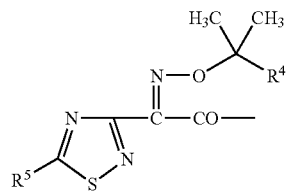

wherein $R^4$ and $R^5$ are each as defined above, and anti isomer (E form) means the other geometrical isomer having the partial structure represented by the following formula:

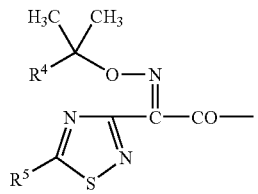

wherein $R^4$ and $R^5$ are each as defined above, and all of such geometrical isomers and mixture thereof are included within the scope of this invention.

In the present specification and claims, the partial structure of these geometrical isomers and mixture thereof are represented for convenience' sake by the following formula:

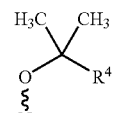

wherein $R^4$ and $R^5$ are each as defined above.

Another point to be noted is that the pyrazolio moiety of the compound [I] can also exist in the tautomeric form, and such tautomeric equilibrium can be represented by the following formula.

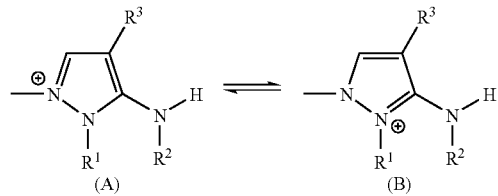

wherein $R^1$, $R^2$ and $R^3$ are each as defined above.

Both of the above tautomeric isomers are included within the scope of the present invention, and in the present specification and claims, however, the object compound [I] is represented for convenience' sake by one expression of the pyrazolio group of the formula (A).

The cephem compound [I] of the present invention can be prepared by the following processes as illustrated in the following.

Process 1

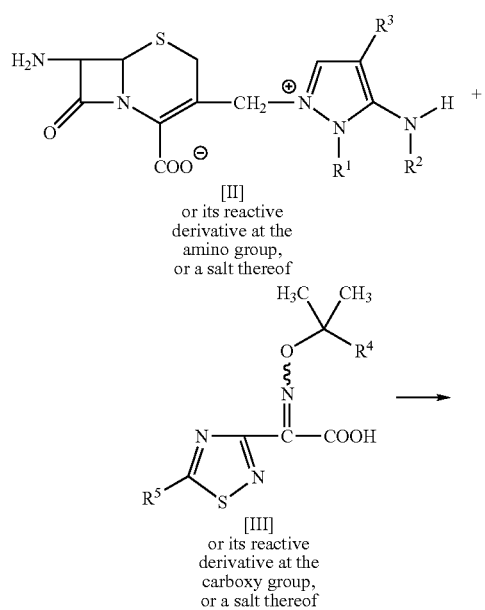

Process 2

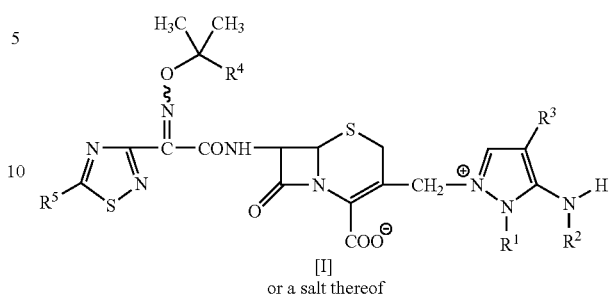

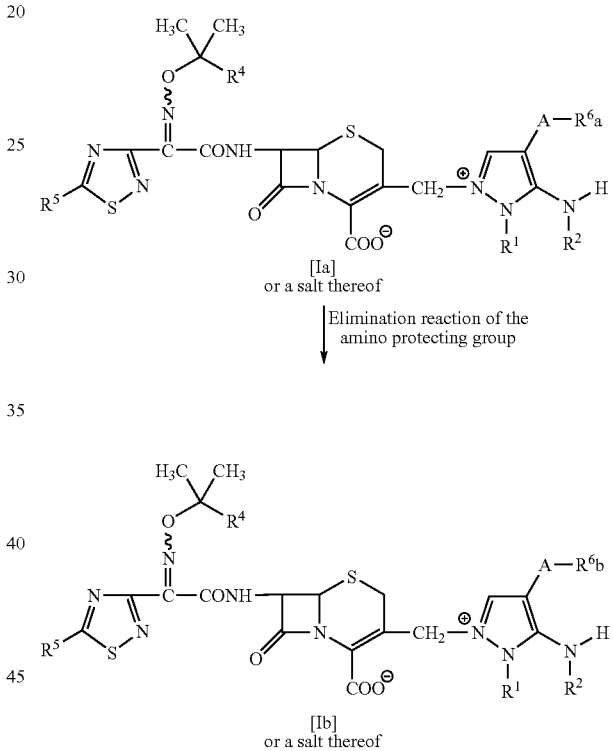

Process 3

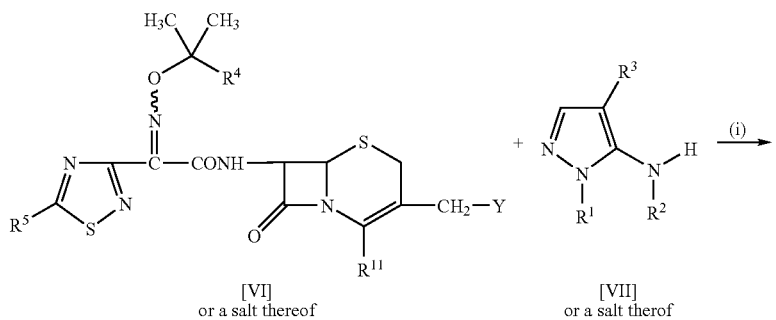

-continued

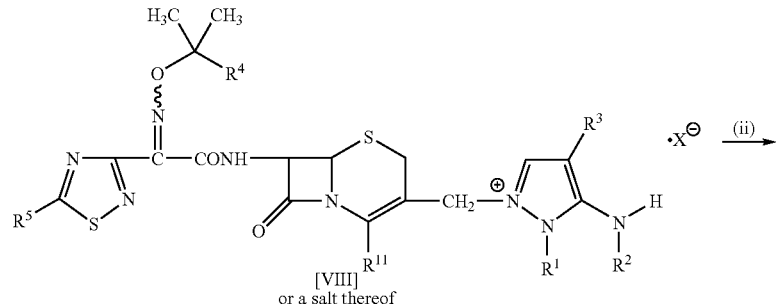
[VIII] or a salt thereof

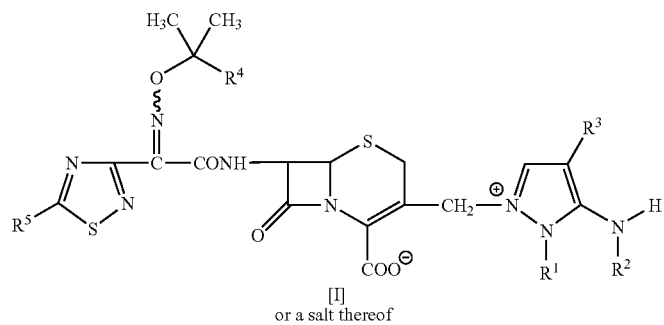
[I] or a salt thereof

Process 4

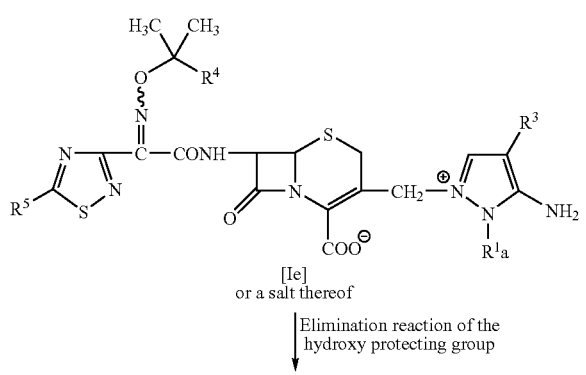
[Ie] or a salt thereof

| Elimination reaction of the hydroxy protecting group

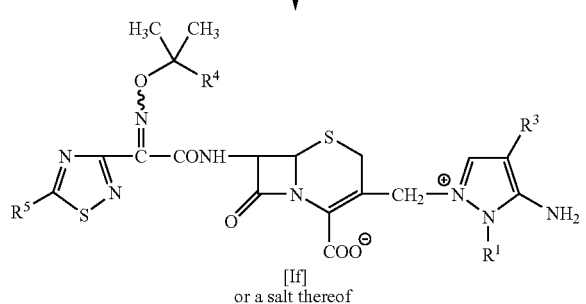
[If] or a salt thereof wherein $R^1$, $R^2$, $R^3$, $R^4$ and $R^5$ are each as defined above,
$R^{11}$ is protected carboxy,
Y is a leaving group,
$X^\ominus$ is an anion, $R^6a$ is $$-(NH)_k-CH\begin{matrix}(Z^1)_q-(CH_2)_s-R^7a\\(Z^2)_r-(CH_2)_t-R^8a\end{matrix} \quad \text{or} \quad -N\begin{matrix}(CH_2)_m-R^9a\\(CH_2)_p-R^{10}a\end{matrix}$$

wherein $Z^1$, $Z^2$, k, q, r, s, t, m and p are each as defined above, and
$R^7a$, $R^8a$, $R^9a$ and $R^{10}a$ are independently protected amino, protected guanidino or protected amidino, $R^6b$ is $$-(NH)_k-CH\begin{matrix}(Z^1)_q-(CH_2)_s-R^7b\\(Z^2)_r-(CH_2)_t-R^8b\end{matrix} \quad \text{or} \quad -N\begin{matrix}(CH_2)_m-R^9b\\(CH_2)_p-R^{10}b\end{matrix}$$

wherein $Z^1$, $Z^2$, k, q, r, S, t, m and p are each as defined above, and
$R^7b$, $R^8b$, $R^9b$ and $R^{10}b$ are independently amino, guanidino or amidino, $R^1a$ is protected hydroxy(lower)alkyl, and
$R^1b$ is hydroxy(lower)alkyl.

The starting compounds [II] and [VI] can be prepared by the following processes.

Process A

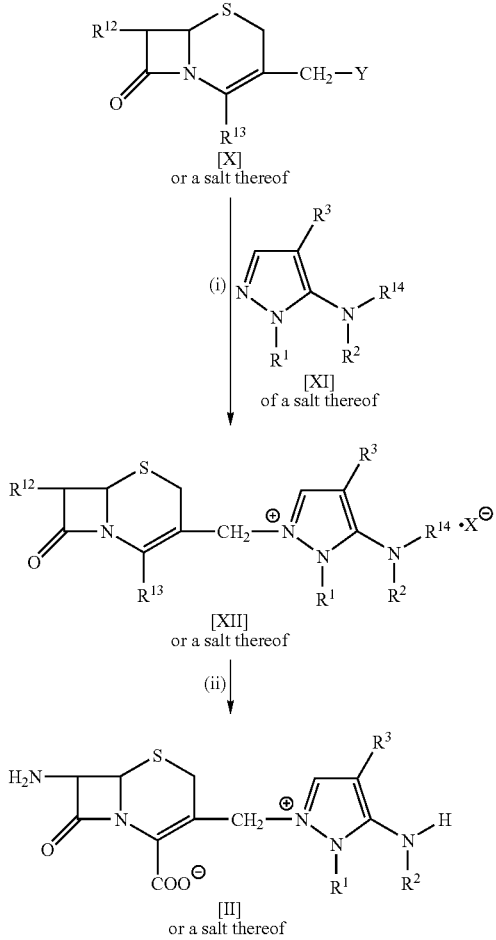

Process B

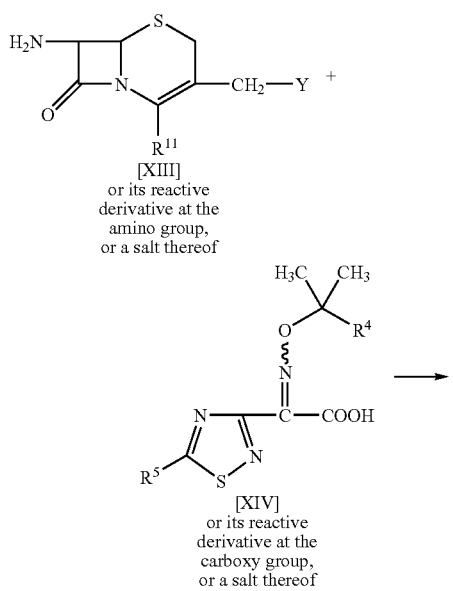

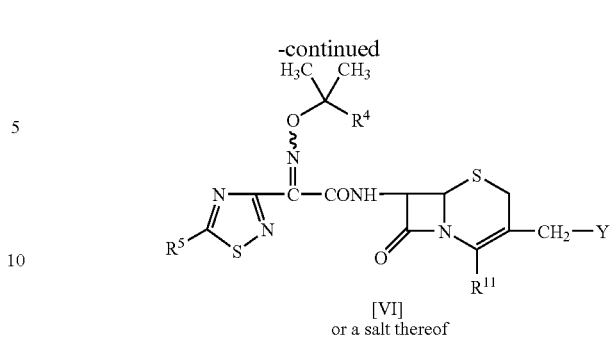

wherein $R^1$, $R^2$, $R^3$, $R^4$, $R^5$, $R^{11}$, Y and $X^\ominus$ are each as defined above,
$R^{12}$ is protected amino,
$R^{13}$ is protected carboxy, and
$R^{14}$ is amino protecting group.

The starting compounds [VII] and [XI] or salts thereof can be prepared by the methods disclosed in the Preparations 2–65 described later or similar manners thereto.

In the above and subsequent descriptions of this specification, suitable examples of the various definitions are explained in detail as follows.

The term "lower" is used to mean a group having 1 to 6, preferably 1 to 4, carbon atoms, unless otherwise indicated.

Suitable "lower alkyl" and "lower alkyl" moiety in "hydroxy(lower)alkyl", "protected hydroxy(lower)alkyl" and "aryl(lower)alkyl", include straight or branched alkyl having 1 to 6 carbon atoms, such as methyl, ethyl, propyl, isopropyl, butyl, isobutyl, sec-butyl, tert-butyl, pentyl, tert-pentyl and hexyl, in which more preferred one is $C_1$–$C_4$ alkyl.

Suitable "hydroxy(lower)alkyl" includes hydroxy($C_1$–$C_6$) alkyl such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and 6-hydroxyhexyl, in which more preferred one is hydroxy($C_1$–$C_4$)alkyl.

Suitable "lower alkylene" formed by $R^1$ and $R^2$ includes straight alkylene having 1 to 6, preferably 2 to 4 carbon atoms, such as methylene, ethylene, trimethylene and tetramethylene, in which more preferred one is straight alkylene having 2 or 3 carbon atoms.

Suitable "lower alkylene" for A includes straight or branched alkylene having 1 to 6 carbon atoms, such as methylene, ethylene, trimethylene, tetramethylene, pentamethylene, hexamethylene and propylene, in which more preferred one is straight alkylene having 1 to 3 carbon atoms, and the most preferred one is methylene.

Suitable "aryl" moiety in "aryl(lower)alkyl" includes $C_6$–$C_{12}$ aryl such as phenyl and naphthyl, in which more preferred one is phenyl.

Suitable "aryl(lower)alkyl" includes mono-, di- or triphenyl(lower)alkyl such as benzyl, phenethyl, benzhydryl and trityl.

Suitable "lower alkanoyl" and "lower alkanoyl" moiety in "lower alkanoylamino" include straight or branched alkanoyl having 1 to 6 carbon atoms, such as formyl, acetyl, propionyl, butyryl, isobutyryl, valeryl, isovaleryl, pivaloyl and hexanoyl, in which more preferred one is $C_1$–$C_4$ alkanoyl.

Suitable "lower alkoxy" moiety in "lower alkoxycarbonyl" and "lower alkoxycarbonylamino" includes straight or branched alkoxy having 1 to 6 carbon atoms, such as methoxy, ethoxy, propoxy, isopropoxy, butoxy, iso-butoxy, sec-butoxy, tert-butoxy, pentyloxy, tert-pentyloxy and hexyloxy, in which more preferred one is $C_1$–$C_4$ alkoxy.

Suitable "amino protecting group" in "protected amino" includes an acyl group as mentioned below, substituted or unsubstituted aryl(lower)alkylidene [e.g., benzylidene, hydroxybenzylidene, etc.], aryl(lower)alkyl such as mono-, di- or triphenyl(lower)alkyl [e.g., benzyl, phenethyl, benzhydryl, trityl, etc.], and the like.

Suitable "acyl" includes lower alkanoyl [e.g., formyl, acetyl, propionyl, hexanoyl, pivaloyl, etc.], mono(or di or tri)halo(lower)alkanoyl [e.g., chloroacetyl, trifluoroacetyl, etc.], lower alkoxycarbonyl [e.g., methoxycarbonyl, ethoxycarbonyl, tert-butoxycarbonyl, tert-pentyloxycarbonyl, hexyloxycarbonyl, etc.], carbamoyl, aroyl [e.g., benzoyl, toluoyl, naphthoyl, etc.], aryl(lower)alkanoyl [e.g., phenylacetyl, phenylpropionyl, etc.], aryloxycarbonyl [e.g., phenoxycarbonyl, naphthyloxycarbonyl, etc.], aryloxy(lower)alkanoyl [e.g., phenoxyacetyl, phenoxypropionyl, etc.], arylglyoxyloyl [e.g., phenylglyoxyloyl, naphthylglyoxyloyl, etc.], aryl(lower)alkoxycarbonyl which optionally substituted by suitable substituent(s) [e.g., benzyloxycarbonyl, phenethyloxycarbonyl, p-nitrobenzyloxycarbonyl, etc.], and the like.

Preferable examples of "amino protecting group" include aryl(lower)alkyl and acyl, in which more preferred ones are aryl(lower)alkyl, lower alkanoyl and lower alkoxycarbonyl, and particularly preferred ones are mono-, di- or triphenyl ($C_1$–$C_6$)alkyl, $C_1$–$C_6$ alkanoyl and ($C_1$–$C_6$)alkoxycarbonyl.

Preferable examples of "protected amino" include aryl(lower)alkylamino and acylamino, in which more preferred ones are aryl(lower)alkylamino, lower alkanoylamino and lower alkoxycarbonylamino, and particularly preferred ones are mono-, di- or triphenyl($C_1$–$C_6$)alkylamino, $C_1$–$C_6$ alkanoylamino and ($C_1$–$C_6$)alkoxycarbonylamino.

As suitable "protecting group" in "protected guanidino" and "protected amidino", those exemplified for the aforementioned "amino protecting group" in "protected amino" can be mentioned.

Preferable examples of "protected guanidino" include acylguanidino (monoacylguanidino and diacylguanidino) such as 2,3-bis[(lower)alkoxycarbonyl]guanidino [e.g., 2,3-bis(tert-butoxycarbonyl)guanidino], in which more preferred one is 2,3-bis[($C_1$–$C_6$)alkoxycarbonyl]guanidino.

Preferable examples of "protected amidino" include acylamidino (monoacylamidino and diacylamidino) such as $N^1$,$N^2$-bis[(lower)alkoxycarbonyl]amidino [e.g., $N^1$,$N^2$-bis(tert-butoxycarbonyl)amidino], in which more preferred one is $N^1$,$N^2$-bis [($C_1$–$C_6$)alkoxycarbonyl]amidino.

Suitable "protected hydroxy" in the "protected hydroxy(lower)alkyl" includes acyloxy group, aryl(lower)alkyloxy group, and the like. Suitable "acyl" moiety in the "acyloxy" includes lower alkanoyl [e.g., formyl, acetyl, propionyl, hexanoyl, pivaloyl, etc.], mono(or di or tri)halo(lower)alkanoyl, [e.g., chloroacetyl, trifluoroacetyl, etc.], lower alkoxycarbonyl, [e.g., methoxycarbonyl, ethoxycarbonyl, tert-butoxycarbonyl, tert-pentyloxycarbonyl, hexyloxycarbonyl, etc.], carbamoyl, and the like. Suitable "aryl(lower)alkyl" moiety in the "aryl(lower)alkyloxy" includes mono-, di- or triphenyl(lower)alkyl [e.g., benzyl, phenethyl, benzhydryl, trityl, etc.], and the like.

Suitable "protected carboxy" includes esterified carboxy and the like, and concrete examples of esterified carboxy include lower alkoxycarbonyl [e.g., methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, 1-cyclopropylethoxycarbonyl, etc.] which may have suitable substituent(s), for example, lower alkanoyloxy(lower)alkoxycarbonyl [e.g., acetoxymethoxycarbonyl, propionyloxymethoxycarbonyl, butyryloxymethoxycarbonyl, valeryloxymethoxycarbonyl, pivaloyloxymethoxycarbonyl, 1-acetoxyethoxycarbonyl, 1-propionyloxyethoxycarbonyl, 2-propionyloxyethoxycarbonyl, hexanoyloxymethoxycarbonyl, etc.], lower alkanesulfonyl(lower)alkoxycarbonyl, [e.g., 2-mesylethoxycarbonyl, etc.] or mono(or di or tri)halo(lower)alkoxycarbonyl [e.g., 2-iodoethoxycarbonyl, 2,2,2-trichloroethoxycarbonyl, etc.]; lower alkenyloxycarbonyl [e.g., vinyloxycarbonyl, allyloxycarbonyl, etc.]; lower alkynyloxycarbonyl [e.g., ethynyloxycarbonyl, propynyloxycarbonyl, etc.]; aryl(lower)alkoxycarbonyl which may have suitable substituent(s) [e.g., benzyloxycarbonyl, 4-methoxybenzyloxycarbonyl, 4-nitrobezyloxycarbonyl, phenethyloxycarbonyl, trityloxycarbonyl, benzhydryloxycarbonyl, bis(methoxyphenyl)methoxycarbonyl, 3,4-dimethoxybenzyloxycarbonyl, 4-hydroxy-3,5-di-tert-butylbenzyloxycarbonyl, etc.]; aryloxycarbonyl which may have suitable substituent(s) [e.g., phenoxycarbonyl, 4-chlorophenoxycarbonyl, tolyloxycarbonyl, 4-tert-butylphenoxycarbonyl, xylyloxycarbonyl, mesityloxycarbonyl, cumenyloxycarbonyl, etc.]; and the like.

Preferable examples of "protected carboxy" include lower alkoxycarbonyl and aryl(lower)alkoxycarbonyl which may have suitable substituent(s), in which more preferred one is ($C_1$–$C_6$)alkoxycarbonyl.

Suitable "leaving group" includes halogen [e.g., chlorine, bromine, iodine, etc.] or acyloxy such as arylsulfonyloxy [e.g., benzenesulfonyloxy, tosyloxy, etc.], lower alkylsulfonyloxy [e.g., mesyloxy, etc.], lower alkanoyloxy [e.g., acetyloxy, propionyloxy, etc.], and the like.

Suitable "anion" includes formate, acetate, trifluoroacetate, maleate, tartrate, methanesulfonate, benzenesulfonate, toluenesulfonate, chloride, bromide, iodide, sulfate, phosphate, and the like.

Suitable pharmaceutically acceptable salts of the object compound [I] are conventional non-toxic salts and include, for example, a salt with a base or an acid addition salt such as a salt with an inorganic base, for example, an alkali metal salt [e.g., sodium salt, potassium salt, etc.], an alkaline earth metal salt [e.g., calcium salt, magnesium salt, etc.], an ammonium salt; a salt with an organic base, for example, an organic amine salt [e.g., trimethylamine salt, triethylamine salt, pyridine salt, picoline salt, ethanolamine salt, triethanolamine salt, dicyclohexylamine salt, N,N'-dibenzylethylenediamine salt, etc.]; an inorganic acid addition salt [e.g., hydrochloride, hydrobromide, sulfate, hydrogensulfate, phosphate, etc.]; an organic carboxylic or sulfonic acid addition salt [e.g., formate, acetate, trifluoroacetate, maleate, tartrate, citrate, fumarate, methanesulfonate, benzenesulfonate, toluenesulfonate, etc.]; and a salt with a basic or acidic amino acid [e.g., arginine, aspartic acid, glutamic acid, etc.].

The preferred embodiments of the cephem compound of the present invention represented by the general formula [I] are as follows.

(1) The compound of the formula [I] wherein $R^1$ is lower alkyl or hydroxy(lower)alkyl, and $R^2$ is hydrogen, aryl(lower)alkyl or acyl, or $R^1$ and $R^2$ are bonded together and form lower alkylene;

$R^4$ is carboxy or esterified carboxy;

$R^5$ is amino, aryl(lower)alkylamino or acylamino; and $R^7$, $R^8$, $R^9$ and $R^{10}$ are independently amino, aryl(lower)alkylamino, acylamino, guanidino, acylguanidino, amidino or acylamidino, or a pharmaceutically acceptable salt thereof.

(2) The compound of (1) above wherein
  $R^1$ is lower alkyl or hydroxy(lower)alkyl, and
  $R^2$ is hydrogen, aryl(lower)alkyl, lower alkanoyl or lower alkoxycarbonyl, or
  $R^1$ and $R^2$ are bonded together and form lower alkylene;
  $R^4$ is carboxy or lower alkoxycarbonyl;
  $R^5$ is amino, aryl(lower)alkylamino, lower alkanoylamino or lower alkoxycarbonylamino; and
  $R^7$, $R^8$, $R^9$ and $R^{10}$ are independently amino, aryl(lower)alkylamino, lower alkanoylamino, lower alkoxycarbonylamino, guanidino, 2,3-bis[(lower)alkoxycarbonyl]guanidino, amidino or $N^1,N^2$-bis[(lower)alkoxycarbonyl]amidino, or a pharmaceutically acceptable salt thereof.

(3) The compound of (2) above wherein
  $R^1$ is $C_1$–$C_6$ alkyl or hydroxy($C_1$–$C_6$)alkyl, and
  $R^2$ is hydrogen, mono-, di- or triphenyl($C_1$–$C_6$)alkyl, $C_1$–$C_6$ alkanoyl or ($C_1$–$C_6$)alkoxycarbonyl, or
  $R^1$ and $R^2$ are bonded together and form $C_1$–$C_6$ alkylene;
  $R^4$ is carboxy or ($C_1$–$C_6$)alkoxycarbonyl;
  $R^5$ is amino, mono-, di- or triphenyl($C_1$–$C_6$)alkylamino, $C_1$–$C_6$ alkanoylamino or ($C_1$–$C_6$)alkoxycarbonylamino;
  $R^7$, $R^8$, $R^9$ and $R^{10}$ are independently amino, mono-, di- or triphenyl($C_1$–$C_6$)alkylamino, $C_1$–$C_6$ alkanoylamino, ($C_1$–$C_6$)alkoxycarbonylamino, guanidino, 2,3-bis[($C_1$–$C_6$)alkoxycarbonyl]guanidino, amidino or $N^1,N^2$-bis[($C_1$–$C_6$)alkoxycarbonyl]amidino, or a pharmaceutically acceptable salt thereof.

(4) The compound of (2) above wherein
  $R^1$ is lower alkyl;
  $R^2$ is hydrogen;
  $R^4$ is carboxy;
  $R^5$ is amino; and
  $R^7$, $R^8$, $R^9$ and $R^{10}$ are amino, or a pharmaceutically acceptable salt thereof.

(5) The compound of (4) above wherein
  $R^1$ is $C_1$–$C_6$ alkyl;
  $R^2$ is hydrogen;
  $R^4$ is carboxy;
  $R^5$ is amino; and
  $R^7$, $R^8$, $R^9$ and $R^{10}$ are amino, or a pharmaceutically acceptable salt thereof.

(6) The compound of the formula [I] wherein
  A is —NHCO—$(CH_2CO)_n$— wherein n is 0 or 1, and
  $R^6$ is $$-NH-CH\begin{smallmatrix}CH_2R^7\\CH_2R^8\end{smallmatrix} \quad \text{or} \quad -N\begin{smallmatrix}(CH_2)_m-R^9\\(CH_2)_p-R^{10}\end{smallmatrix}$$

wherein m and p are independently an integer of 1 to 3, and $R^7$, $R^8$, $R^9$ and $R^{10}$ are independently amino or protected amino, or a pharmaceutically acceptable salt thereof.

(7) The compound of (6) above wherein
  A is —NHCO—, and
  $R^7$, $R^8$, $R^9$ and $R^{10}$ are amino, or a pharmaceutically acceptable salt thereof.

(8) The compound of the formula [I] wherein
  A is —NHCO—$(CH_2CO)_n$— wherein n is 0 or 1, —NH—CO—CO— or $$-\underset{H}{N}\hspace{-2pt}\diagdown\hspace{-6pt}\underset{\underset{\displaystyle O}{\|}}{\square}\hspace{-6pt}\diagup\hspace{-2pt}\underset{O}{\|}\text{CH}_3\text{, and}$$

$R^6$ is $$-NH-CH\begin{smallmatrix}(CH_2)_s-R^7\\(CH_2)_t-R^8\end{smallmatrix} \quad \text{or} \quad -N\begin{smallmatrix}(CH_2)_m-R^9\\(CH_2)_p-R^{10}\end{smallmatrix}$$

wherein s, t, m and p are independently an integer of 1 to 6, and $R^7$, $R^8$, $R^9$ and $R^{10}$ are amino or protected amino, or a pharmaceutically acceptable salt thereof.

(9) The compound of the formula [I], wherein
  A is a bond or —NHCO—, and
  $R^6$ is:

$$-CH\begin{smallmatrix}(CH_2)_s-R^7\\(CH_2)_t-R^8\end{smallmatrix},$$

wherein s and t are independently an integer of 0 to 6, and $R^7$ and $R^8$ are independently amino, protected amino, guanidino, protected guanidino, amidino or protected amidino, or a pharmaceutically acceptable salt thereof.

(10) The compound of (9), wherein
  A is —NHCO—, and
  $R^7$ and $R^8$ are independently amino or guanidino, or a pharmaceutically acceptable salt thereof.

(11) The compound of the formula [I], wherein
  A is lower alkylene, and
  $R^6$ is:

$$-N\begin{smallmatrix}(CH_2)_m-R^9\\(CH_2)_p-R^{10}\end{smallmatrix},$$

wherein m and p are independently an integer of 0 to 6, and $R^9$ and $R^{10}$ are independently amino or amidino, or a pharmaceutically acceptable salt thereof.

(12) The compound of the formula [I], wherein
  A is —NHCO— and
  $R^6$ is:

$$-(NH)_k-CH\begin{smallmatrix}(Z^1)_q-(CH_2)_s-R^7\\(Z^2)_r-(CH_2)_t-R^8\end{smallmatrix},$$

wherein $Z^1$ and $Z^2$ are independently —NHCO—, or —CONH—,
k, q and r are independently 0 or 1,
s and t are independently an integer of 1 to 6, and $R^7$ and $R^8$ are amino; or a pharmaceutically acceptable salt thereof.

A is preferably —NHCO—(CH₂CO)$_n$— wherein n is 0 or 1, —NH—CO—CO— or

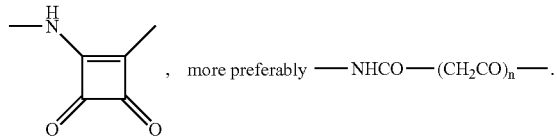, more preferably —NHCO—(CH₂CO)$_n$—.

n is preferably 0.
R⁶ is preferably selected from

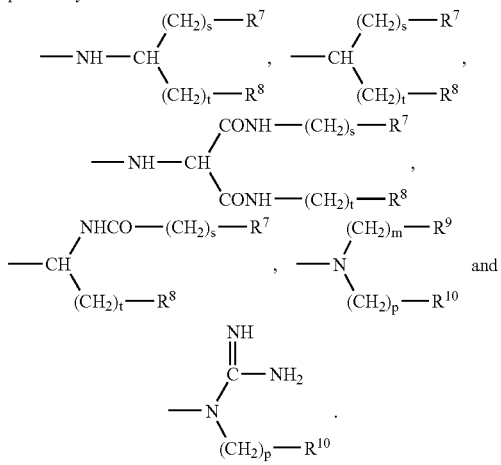

More preferably, R⁶ is

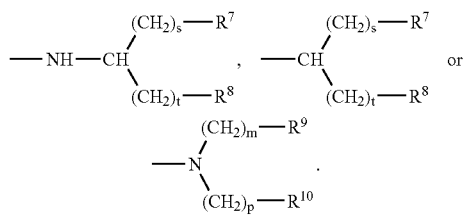

Particularly preferably, R⁶ is

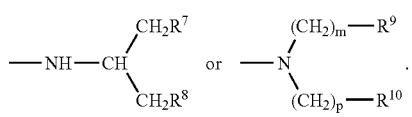

k is preferably 1.

q and r are preferably 0.

s and t are preferably an integer of 1 to 6, more preferably an integer of 1 to 4.

Alternatively, when one of s and t is 0, the other is preferably an integer of 1 to 6, more preferably an integer of 1 to 4.

When q is 1, s is preferably an integer of 1 to 6, more preferably an integer of 1 to 4.

When r is 1, t is preferably an integer of 1 to 6, more preferably an integer of 1 to 4.

m and p are preferably an integer of 1 to 6, more preferably an integer of 1 to 4, particularly preferably an integer of 1 to 3.

R⁷ and R⁸ are preferably independently amino or guanidino, more preferably amino.

R⁹ and R¹⁰ are preferably independently amino or amidino, more preferably amino.

R⁴ is preferably carboxy.

R⁵ is preferably amino.

A preferred embodiment of the compound of the formula [I] is selected from the group consisting of 7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylate, 7β-[(Z)-2-(5-amino-1,2,4-thiadiazol-3-yl)-2-(1-carboxy-1-methylethoxyimino)acetamido]-3-[3-amino-4-({[N-(2-aminoethyl)-N-(3-aminopropyl)amino]carbonyl}amino)-2-methyl-1-pyrazolio]methyl-3-cephem-4-carboxylate, 7β-[(Z)-2-(5-amino-1,2,4-thiadiazol-3-yl)-2-(1-carboxy-1-methylethoxyimino)acetamido]-3-3-amino-4-{3-[2-amino-1-(aminomethyl)ethyl]ureido}-2-methyl-1-pyrazolio)methyl-3-cephem-4-carboxylate, 7β-[(Z)-2-(5-amino-1,2,4-thiadiazol-3-yl)-2-(1-carboxy-1-methylethoxyimino)acetamido]-3-{3-amino-4-[(3-{[2-amino-1-(aminomethyl)ethyl]amino}-3-oxopropanoyl)amino]-2-methyl-1-pyrazolio}methyl-3-cephem-4-carboxylate, 7β-[(Z)-2-(5-amino-1,2,4-thiadiazol-3-yl)-2-(1-carboxy-1-methylethoxyimino)acetamido]-3-[3-amino-4-{[4-amino-2-(2-aminoethyl)butanoyl]amino}-2-methyl-1-pyrazolio]methyl-3-cephem-4-carboxylate, and 7β-[(Z)-2-(5-amino-1,2,4-thiadiazol-3-yl)-2-(1-carboxy-1-methylethoxyimino)acetamido]-3-[3-amino-4-{[3-amino-2-(aminomethyl)propanoyl]amino}-2-methyl-1-pyrazolio]methyl-3-cephem-4-carboxylate, or a pharmaceutically acceptable salt thereof.

The processes for preparing the object compound of the present invention are explained in detail in the following.

Process 1

The compound [I] or a salt thereof can be prepared by reacting the compound [II] or its reactive derivative at the amino group, or a salt thereof with the compound [III] or its reactive derivative at the carboxy group, or a salt thereof.

Suitable reactive derivative at the amino group of the compound [II] includes Schiff's base type imino or its tautomeric enamine type isomer formed by the reaction of the compound [II] with a carbonyl compound such as aldehyde, ketone and the like; a silyl derivative formed by the reaction of the compound [II] with a silyl compound such as bis(trimethylsilyl)acetamide, mono(trimethylsilyl)acetamide [e.g., N-(trimethylsilyl)acetamide], bis(trimethylsilyl)urea and the like; a derivative formed by the reaction of the compound [II] with phosphorus trichloride or phosgene.

Suitable salts of the compound [II] and its reactive derivative can be referred to the ones as exemplified for the compound [I].

Suitable reactive derivative at the carboxy group of the compound [III] includes an acid halide, an acid anhydride, an activated amide, and an activated ester. A suitable example of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, alkanesulfonic acid [e.g., methanesulfonic acid, etc.], aliphatic carboxylic acid [e.g., acetic acid, propionic acid, butyric acid, isobutyric acid, pivalic acid, pentanoic acid, isopentanoic acid, 2-ethylbutyric acid, trichloroacetic acid, etc.] and aromatic carboxylic acid [e.g., benzoic acid, etc.]; a symmetrical acid anhydride; an activated amide with imidazole, 4-substituted imidazole, dimethylpyrazole, triazole or tetrazole; an activated ester [e.g., cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.]; or an ester with an N-hydroxy compound [e.g., N,N-dimethylhydroxylamine, 1-hydroxy-2-(1H)-pyridone, N-hydroxysuccinimide, N-hydroxyphthalimide, N-hydroxy-1H-benzotriazole, etc.]. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely affect the reaction. These conventional solvents may also be used in a mixture with water.

In this reaction, when the compound [III] is used in free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.], triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; and the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, and the like.

The reaction temperature is not critical, and the reaction is usually carried out under cooling to warming.

Process 2

The compound [Ib] or a salt thereof can be prepared by subjecting the compound [Ia] or a salt thereof to elimination reaction of the amino protecting group.

Elimination reaction is carried out in accordance with a conventional method such as hydrolysis and the like.

The hydrolysis is preferably carried out in the presence of a base or an acid including Lewis acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, and the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], and the like is preferably carried out in the presence of cation trapping agents [e.g., anisole, phenol, etc.].

The reaction is usually carried out in a solvent such as water, alcohol [e.g., methanol, ethanol, etc.], methylene chloride, tetrahydrofuran, a mixture thereof or any other solvent which does not adversely influence the reaction. A liquid base or acid can be also used as a solvent.

The reaction temperature is not critical and the reaction is usually carried out under cooling to warming.

Process 3-(i)

The compound [VIII] or a salt thereof can be prepared by reacting the compound [VI] or a salt thereof with the compound [VII] or a salt thereof.

Suitable salt of the compounds [VI], [VII] and [VIII] can be referred to the ones as exemplified for the compound [I].

The present reaction may be carried out in a solvent such as water, phosphate buffer, acetone, chloroform, acetonitrile nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [VII] is liquid, it can also be used as a solvent.

The reaction is preferably conducted in the presence of a base, for example, an inorganic base such as alkali metal hydroxide, alkali metal carbonate, alkali metal hydrogencarbonate, an organic base such as trialkylamine, and the like.

The reaction temperature is not critical, and the reaction is usually carried out at ambient temperature, under warming or under heating. The present reaction is preferably carried out in the presence of alkali metal halide [e.g., sodium iodide, potassium iodide, etc.], alkali metal thiocyanate [e.g., sodium thiocyanate, potassium thiocyanate, etc.], and the like.

Anion $X^\ominus$ may be one derived from a leaving group Y, and it may be converted to other anion by a conventional method.

Process 3-(ii)

The compound [I] or a salt thereof can be prepared by subjecting the compound [VIII] or a salt thereof to elimination reaction of the carboxy protecting group.

Elimination reaction is carried out in similar manner to the reaction in the aforementioned Process 2, and therefore the reagents to be used and reaction conditions (e.g., solvent, reaction temperature, etc.) can be referred to those of Process 2.

Process 4

The compound [If] or a salt thereof can be prepared by subjecting the compound [Ie] or a salt thereof to elimination reaction of the hydroxy protecting group.

Suitable method of this elimination reaction includes conventional one such as hydrolysis, reduction and the like.

(i) For Hydrolysis:

The hydrolysis is preferably carried out in the presence of a base or an acid including Lewis acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, and the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.] and the like is preferably carried out in the presence of cation trapping agents [e.g., anisole, phenol, etc.].

The reaction is usually carried out in a solvent such as water, alcohol [e.g., methanol, ethanol, etc.], methylene chloride, tetrahydrofuran, a mixture thereof or any other solvent which does not adversely influence the reaction. A liquid base or acid can be also used as a solvent.

The reaction temperature is not critical and the reaction is usually carried out under cooling to warming.

(ii) For Reduction:

Reduction is carried out in a conventional manner, including chemical reduction and catalytic reduction.

Suitable reducing reagents to be used in chemical reduction are a combination of a metal [e.g., tin, zinc, iron, etc.] or metallic compound [e.g., chromium chloride, chromium acetate, etc.] and an organic acid or inorganic acid [e.g., formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g., platinum plate, spongy platinum, platinum black, colloidal platinum, platinum oxide, platinum wire, etc.], palladium catalysts [e.g., spongy palladium, palladium black, palladium oxide, palladium on carbon, colloidal palladium, palladium on barium sulfate, palladium on barium carbonate, etc.], nickel catalysts [e.g., reduced nickel, nickel oxide, Raney nickel, etc.], cobalt catalysts [e.g., reduced cobalt, Raney cobalt, etc.], iron catalysts [e.g., reduced iron, Raney iron, etc.], copper catalysts [e.g., reduced copper, Raney copper, Ullman copper, etc.] and the like.

The reduction is usually carried out in a conventional solvent which does not adversely influence the reaction such as water, methanol, ethanol, propanol, N,N-dimethylformamide or a mixture thereof.

Additionally, in case that the above-mentioned acids to be used in chemical reduction are liquid, they can also be used as a solvent.

Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

When $R^5$ is protected amino, the amino protecting group in $R^5$ can be eliminated by a conventional method such as hydrolysis.

Processes A and B for the preparation of the starting compounds are explained in detail in the following.

Process A-(i)

The compound [XII] or a salt thereof can be prepared by reacting the compound [α] or a salt thereof with the compound [XI] or a salt thereof.

This reaction can be carried out in a similar manner to the reaction in the aforementioned Process 3-(i), and therefore the reagents to be used and reaction conditions (e.g., solvent, reaction temperature, etc.) can be referred to those of Process 3-(i).

Process A-(ii)

The compound [II] or a salt thereof can be prepared by subjecting the compound [XII] or a salt thereof to elimination reaction of the amino protecting groups in $R^{12}$ and $R^{14}$ and the carboxy protecting group in $R^{13}$.

This reaction can be carried out in a similar manner to the reaction in the aforementioned Process 2, and therefore the reagents to be used and reaction conditions (e.g., solvent, reaction temperature, etc.) can be referred to those of Process 2.

Process B

The compound [VI] or a salt thereof can be prepared by reacting the compound [XIII] or its reactive derivative at the amino group, or a salt thereof with the compound [XIV] or its reactive derivative at the carboxy group, or a salt thereof.

This reaction can be carried out in a similar manner to the reaction in the aforementioned Process 1, and therefore the reagents to be used and reaction conditions (e.g., solvent, reaction temperature, etc.) can be referred to those of Process 1.

The compounds obtained by the above processes can be isolated and purified by a conventional method such as pulverization, recrystallization, column chromatography, reprecipitation, and the like.

It is to be noted that the compound [I] and other compounds may include one or more stereoisomer(s) such as optical isomer(s) and geometrical isomer(s) due to asymmetric carbon atom(s) and double bond(s), and all of such isomers and mixtures thereof are included within the scope of this invention.

The object compounds [I] and pharmaceutically acceptable salts thereof include solvates [e.g., enclosure compounds (e.g., hydrate, etc.)].

The object compound [I] and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound [I], the test data on MIC (minimal inhibitory concentration) of a representative compound of this invention are shown in the following.

Test Method:

In vitro antibacterial activity was determined by the two-fold agar-plate dilution method as described below.

One loopful of an overnight culture of each test strain in Trypticase-soy broth ($10^6$ viable cells per ml) was streaked on heart infusion agar (HI-agar) containing graded concentrations of representative test compound, and the minimal inhibitory concentration (MIC) was expressed in µg/ml after incubation at 37° C. for 20 hours.

Test Compound

Compound (a): 7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylate (Example 1)

Compound (b): 7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylic acid hydrogensulfate (Example 2)

Compound (c): 7β-[(Z)-2-(5-amino-1,2,4-thiadiazol-3-yl)-2-(1-carboxy-1-methylethoxyimino)acetamido]-3-[3-amino-4-({[N-(2-aminoethyl)-N-(3-aminopropyl)amino]carbonyl}-amino)-2-methyl-1-pyrazolio]methyl-3-cephem-4-carboxylate (Example 3)

Compound (d): 7β-[(Z)-2-(5-amino-1,2,4-thiadiazol-3-yl)-2-(1-carboxy-1-methylethoxyimino)acetamido]-3-(3-amino-4-{3-[2-amino-1-(aminomethyl)ethyl]ureido}-2-methyl-1-pyrazolio)methyl-3-cephem-4-carboxylic acid hydrogensulfate (Example 4)

Compound (e): 7β-[(Z)-2-(5-amino-1,2,4-thiadiazol-3-yl)-2-(1-carboxy-1-methylethoxyimino)acetamido]-3-{3-amino-4-[(3-{[2-amino-1-(aminomethyl)ethyl]amino}-3-oxopropanoyl)amino]-2-methyl-1-pyrazolio}methyl-3-cephem-4-carboxylate (Example 5)

Ceftazidime

Test Results:

TABLE 1

| Test strain | Test compound | MIC (μg/ml) |
| --- | --- | --- |
| Pseudomonas aeruginosa FP 1380 | (a) | 1 |
| | (b) | 1 |
| | (c) | 1 |
| | (d) | 1 |
| | (e) | 1 |
| | Ceftazidime | 128 |

For therapeutic administration, the object compound [I] and pharmaceutically acceptable salts thereof of the present invention are used in the form of a conventional pharmaceutical preparation which contains said compound as an active ingredient, in admixture with pharmaceutically acceptable carriers such as an organic or inorganic solid or liquid excipient which is suitable for oral, parenteral or external administration. The pharmaceutical preparations may be in a solid form such as tablet, granule, powder, capsule, or in a liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may very from and also depend upon the age, conditions of the patient, a kind of diseases, a kind of the compound [I] to be applied, etc. In general amounts between 1 mg and 4,000 mg or even more per day may be administered to a patient. An average single dose of about 50 mg, 100 mg, 250 mg, 500 mg, 1000 mg or 2000 mg of the object compounds [I] of the present invention may be used in treating diseases infected by pathogenic microorganisms.

The following Preparations and Examples are given for the purpose of illustrating the present invention in more detail.

PREPARATION 1

To a solution of (Z)-2-(5-amino-1,2,4-thiadiazol-3-yl)-2-(1-tert-butoxycarbonyl-1-methylethoxyimino)acetic acid (319 g) in N,N-dimethylacetamide (1.5 L) were added potassium carbonate (113 g) and methanesulfonyl chloride (126 ml) under ice-cooling. The mixture was stirred at 10° C. for 2 hours. The reaction mixture was added to a mixture of ethyl acetate and water. The organic layer was washed with water and brine to give an activated acid solution. On the other hand, a suspension of 4-methoxybenzyl 7β-amino-3-chloromethyl-3-cephem-4-carboxylate hydrochloride (300 g) in a mixture of water (1 L) and ethyl acetate (1 L) was adjusted to pH 6 with triethylamine under ice-cooling. To the resulting mixture was dropwise added the above obtained activated acid solution at 10° C. under stirring. Stirring was continued at 5–10° C. for 1.5 hours keeping pH of the reaction mixture at 6 with triethylamine. The organic layer was separated, washed with water and brine, and evaporated in vacuo. The concentrate was poured into diisopropyl ether (15 L), and the resulting precipitate was collected by filtration and dried to give 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (495.7 g).

$^1$H-NMR(DMSO-$d_6$) δ 1.39 (9H, s), 1.44 (6H, s), 3.45–3.70 (2H, m), 3.76 (3H, s), 4.46 and 4.54 (1H, ABq, J=16 Hz), 5.10–5.28 (2H+1H, m), 5.90 (1H, dd, J=4.9 Hz, 8.5 Hz), 6.94 (2H, d, J=8.7 Hz), 7.36 (2H, d, J=8.7 Hz), 8.18 (2H, brs), 9.52 (1H, d, J=8.5 Hz)

PREPARATION 2

To a solution of 5-amino-1-methylpyrazole (100 g) in water (700 ml) were added concentrated hydrochloric acid (86 ml) and sodium nitrite (63.9 g) in water (200 ml) at a temperature below 10° C. The reaction mixture was stirred at 5° C. for 30 minutes. The precipitated solid was collected by filtration and dried to give 5-amino-1-methyl-4-nitrosopyrazole (117 g).

$^1$H-NMR(DMSO-$d_6$) δ 3.52 and 3.59 (3H, s), 7.22 and 8.51 (1H, s), 8.17 and 8.51 (1H, brs)

PREPARATION 3

To a suspension of 5-amino-1-methyl-4-nitrosopyrazole (117 g) were added sulfuric acid (91 g) and 10% palladium on carbon (58 g). The mixture was hydrogenated under balloon pressure for 10 hours. The reaction mixture was filtered and the filtrate was concentrated in vacuo. To the concentrate was added isopropyl alcohol (2.3 L) and the mixture was stirred for 1 hour. The precipitated solid was collected by filtration and dried to give 4,5-diamino-1-methylpyrazole sulfate (158 g).

$^1$H-NMR($D_2O$) δ 3.74 (3H, s), 7.80 (1H, s)

PREPARATION 4

A solution of 4,5-diamino-1-methylpyrazole sulfate (158 g) in water (1.1 L) was neutralized to pH 6.9 with 4N aqueous sodium hydroxide solution, and dioxane (474 ml) was added to this solution. To the resulting mixture was added dropwise phenyl chloroformate (124 g) maintaining pH of the mixture at 6.9 with 4N aqueous sodium hydroxide solution at a temperature below 10° C. The reaction mixture was stirred for 1 hour. The precipitated solid was collected by filtration and dried to give 5-amino-1-methyl-4-phenoxycarbonylaminopyrazole (155 g).

$^1$H-NMR(DMSO-d$_6$) δ 3.52 (3H, s), 5.00 (2H, brs), 7.10–7.50 (6H, m), 8.93 (1H, brs)

PREPARATION 5

To a suspension of 5-amino-1-methyl-4-phenoxycarbonylaminopyrazole (153.8 g) in tetrahydrofuran (1 L) were added triethylamine (67 g) and triphenylmethyl chloride (185 g) at room temperature. The mixture was stirred for 6.5 hours. To the reaction mixture was added heptane (2.6 L) and the mixture was stirred for 1 hour. The precipitated solid was collected by filtration and washed with heptane-diisopropyl ether (1:1). The crude solid was suspended in water (3 L) and the suspension was stirred for 1 hour. The solid was collected by filtration and dried to give 1-methyl-4-phenoxycarbonylamino-5-triphenylmethylaminopyrazole (253.6 g).

$^1$H-NMR(DMSO-d$_6$) δ 2.74 (3H, s), 5.57 (1H, brs), 7.00–7.50 (21H, m), 8.12 (1H, brs)

PREPARATION 6

To a solution of tert-butyl 2-aminoethylcarbamate (4.81 g) in dehydrated chloroform (10 ml) were added sodium carbonate (1.06 g) and N-(2-bromoethyl)tritylamine (3.66 g), and the mixture was stirred under reflux for 3 hours. To the reaction mixture were added diethyl ether and hexane, and the solution was washed with water. The mixture was extracted with 5% aqueous citric acid solution, and the aqueous layer was washed with diethyl ether. The aqueous layer was then made alkaline with sodium hydrogencarbonate followed by extraction with diethyl ether. The organic layer was washed with brine, dried over anhydrous sodium sulfate, filtered and concentrated in vacuo to give tert-butyl 2-{[2-(tritylamino)ethyl]amino}ethylcarbamate (1.86 g) as a viscous oil.

$^1$H-NMR(CDCl$_3$) δ 1.43 (9H, s), 1.77 (2H, br), 2.27 (2H, t, J=6.0 Hz), 2.64 (2H, t, J=6.0 Hz), 2.70 (2H, t, J=6.0 Hz), 3.13–3.23 (2H, m), 4.93 (1H, br), 7.13–7.32 (9H, m), 7.43–7.51 (6H, m)

PREPARATION 7

To a suspension of phenyl [1-methyl-5-(tritylamino)pyrazol-4-yl]carbamate (712 mg) and tert-butyl 2-{[2-(tritylamino)ethyl]amino}ethylcarbamate (668 mg) in dehydrated chloroform (4 ml) was added N-ethyldiisopropylamine (0.257 ml), and the mixture was stirred under reflux for 16 hours. To the reaction mixture was added ethyl acetate, and the solution was washed successively with water, 5% aqueous citric acid solution, 1M aqueous sodium hydroxide solution and brine. The organic layer was dried over anhydrous sodium sulfate, filtered and concentrated in vacuo. The residue was purified by column chromatography on silica gel eluting with 5% methanol/methylene chloride to give tert-butyl (2-{N-({[1-methyl-5-(tritylamino)pyrazol-4-yl]amino}carbonyl)-N-[2-(tritylamino)ethyl]amino}ethyl)carbamate (1.15 g) as a solid.

$^1$H-NMR(CDCl$_3$) δ 1.29 (9H, s), 2.07 (1H, br), 2.37–2.47 (2H, m), 2.80 (3H, s), 2.89–2.92 (2H, m), 3.10–3.20 (2H, m), 3.21–3.32 (2H, m), 5.09 (1H, brs), 5.39 (1H, br), 6.97 (1H, s), 7.15–7.35 (30H, m), 7.81 (1H, br)

PREPARATION 8

To a suspension of phenyl [1-methyl-5-(tritylamino)pyrazol-4-yl]carbamate (949 mg) and di-tert-butyl [iminobis(2,1-ethanediyl)]biscarbamate (693 mg) in dehydrated chloroform (4.5 ml) was added N-ethyldiisopropylamine (0.342 ml), and the mixture was stirred under reflux for 18.5 hours. To the reaction mixture was added ethyl acetate, and the solution was washed successively with 5% aqueous citric acid solution, 1M aqueous sodium hydroxide solution and brine. The organic layer was dried over anhydrous sodium sulfate, filtered and concentrated in vacuo. The residue was triturated with a mixed solvent of diisopropyl ether, diethyl ether and hexane to give di-tert-butyl [[({[1-methyl-5-(tritylamino)pyrazol-4-yl]amino}carbonyl)imino]bis(2,1-ethanediyl)]biscarbamate (1.17 g) as a solid.

$^1$H-NMR(CDCl$_3$) δ 1.39 (18H, s), 2.85 (3H, s), 3.05–3.17 (4H, m), 3.03–3.24 (4H, m), 5.04 (2H, br), 5.09 (1H, brs), 7.13–7.26 (15H, m), 7.17 (1H, s)

PREPARATION 9

To a solution of tert-butyl 2-aminoethylcarbamate (481 mg) in dehydrated chloroform (3 ml) were added sodium carbonate (212 mg) and (3-bromopropyl)tritylamine (694 mg), and the mixture was stirred under reflux for 3.5 hours. To the reaction mixture were added diethyl ether and hexane, and the solution was washed with water. The mixture was extracted with 5% aqueous citric acid solution, and the aqueous layer was washed with diethyl ether. The aqueous solution was then made alkaline with sodium hydrogencarbonate followed by extraction with diethyl ether. The organic layer was washed with brine, dried over anhydrous sodium sulfate, filtered and concentrated in vacuo to give tert-butyl 2-{[3-(tritylamino)propyl]amino}ethylcarbamate (410 mg) as a viscous oil.

$^1$H-NMR(CDCl$_3$) δ 1.43 (9H, s), 1.60–1.80 (2H, br), 1.65 (2H, quint, J=6.9 Hz), 2.19 (2H, t, J=6.9 Hz), 2.67 (2H, t, J=6.9 Hz), 2.69 (2H, t, J=6.0 Hz), 3.11–3.22 (2H, m), 4.95 (1H, br), 7.10–7.30 (9H, m), 7.40–7.50 (6H, m)

PREPARATION 10

To a suspension of phenyl [1-methyl-5-(tritylamino)pyrazol-4-yl]carbamate (423 mg) and tert-butyl 2-{[3-(tritylamino)propyl]amino}ethylcarbamate (410 mg) in dehydrated chloroform (2.5 ml) was added N-ethyldiisopropylamine (0.152 ml), and the mixture was stirred under reflux for 16 hours. To the reaction mixture was added ethyl acetate, and the solution was washed successively with water, 5% aqueous citric acid solution, 1M aqueous sodium hydroxide solution and brine. The organic layer was dried over anhydrous sodium sulfate, filtered and concentrated in vacuo. The residue was purified by column chromatography on silica gel eluting with 5% methanol/methylene chloride to give tert-butyl (2-{N-({[1-methyl-5-(tritylamino)pyrazol-4-yl]amino}carbonyl)-N-[3-(tritylamino)propyl]-ethyl)carbamate (657 mg) as a solid.

$^1$H-NMR(CDCl$_3$) δ 1.22 (9H, s), 1.55–1.65 (3H, m), 2.08–2.18 (2H, m), 2.85 (3H, s), 3.05–3.18 (4H, m), 3.12–3.23 (2H, m), 5.01 (1H, br), 5.07 (1H, brs), 6.24 (1H, br), 7.04 (1H, s), 7.15–7.30 (24H, m), 7.37–7.45 (6H, m)

EXAMPLE 1

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (838 mg) in N,N-dimethylformamide (2.0 ml) was added 1,3-bis(trimethylsilyl)urea (1.26 g) and the mixture was stirred at room temperature for 30 minutes. To the solution was added potassium iodide (286 mg) and the mixture was stirred at room temperature for 30 minutes. To the reaction mixture was added a solution of tert-butyl (2-{N-({[1-methyl-5-(tritylamino)pyrazol-4-yl]amino}carbonyl)-N-[2-(tritylamino)ethyl]amino}-ethyl)carbamate (1.17 g) in N,N-dimethylformamide (3 ml) and the whole mixture was stirred at 45–50° C. for 2.5 hours. To the resulting reaction mixture was added ethyl acetate (60 ml) and the solution was washed successively with water (50 ml), 10% aqueous sodium trifluoroacetate (50 ml×2) and brine (50 ml), dried over anhydrous sodium sulfate and filtered. The filtrate was concentrated to about 8 ml in vacuo. The concentrate was poured into diisopropyl ether (100 ml) and the resulting precipitate was collected by filtration and dried in vacuo. To a solution of the solid in methylene chloride (4.7 ml) were added anisole (1.6 ml) and trifluoroacetic acid (4.7 ml).

The resulting solution was stirred at room temperature for 4 hours and poured into diisopropyl ether (100 ml). The resulting precipitate was collected by filtration and dried in vacuo to give a crude product (1.26 g), which was purified by preparative high-performance liquid chromatography (HPLC) utilizing ODS column. The eluate containing a desired product was concentrated to about 30 ml in vacuo. The concentrate was adjusted to about pH 3 with concentrated hydrochloric acid and chromatographed on Diaion (registered trademark) HP-20 (Mitsubishi Chemical Corporation) eluting with 30% aqueous 2-propanol. The eluate was concentrated to about 10 ml in vacuo and lyophilized to give 7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylate (58 mg) as an amorphous solid.

$^1$H-NMR(D$_2$O) δ 1.52 (6H, s), 3.20 (1H, d, J=17.6 Hz), 3.26 (4H, t, J=6.0 Hz), 3.51 (1H, d, J=17.6 Hz), 3.62–3.74 (4H, m), 3.74 (3H, s), 4.95 (1H, d, J=14.9 Hz), 5.27 (1H, d, J=14.9 Hz), 5.27 (1H, d, J=4.8 Hz), 5.83 (1H, d, J=4.8 Hz), 7.85 (1H, s)

EXAMPLE 2

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (889 mg) in N,N-dimethylformamide (2.0 ml) was added N-(trimethylsilyl)acetamide (856 mg) and the mixture was stirred at room temperature for 30 minutes. To the solution was added potassium iodide (303 mg) and the mixture was stirred at room temperature for 30 minutes. To the reaction mixture was added a solution of di-tert-butyl [[({[1-methyl-5-(tritylamino)pyrazol-4-yl]amino}carbonyl)imino]bis(2,1-ethanediyl)]biscarbamate (1.03 g) in N,N-dimethylformamide (2 ml) and the whole mixture was stirred at 45–55° C. for 2.75 hours. To the resulting reaction mixture was added ethyl acetate (20 ml) and the solution was washed successively with water (20 ml×2), 10% aqueous sodium trifluoroacetate (10 ml×2) and brine (10 ml), dried over anhydrous sodium sulfate and filtered. The filtrate was concentrated to about 9 ml in vacuo. The concentrate was poured into diisopropyl ether (45 ml) and the resulting precipitate was collected by filtration and dried in vacuo. To a solution of the solid in methylene chloride (4.7 ml) were added anisole (1.6 ml) and trifluoroacetic acid (4.7 ml).

The resulting solution was stirred at room temperature for 4 hours and poured into diisopropyl ether (80 ml). The resulting precipitate was collected by filtration and dried in vacuo to give a crude product (1.18 g), which was purified by preparative high-performance liquid chromatography (HPLC) utilizing ODS column. The eluate containing a desired product was concentrated to about 30 ml in vacuo. The concentrate was adjusted to about pH 3 with concentrated hydrochloric acid and chromatographed on Sepabeads (registered trademark) SP207 (Mitsubishi Chemical Corporation) eluting with 40% aqueous 2-propanol. The eluate was concentrated to about 10 ml in vacuo and 1M sulfuric acid (0.24 ml) was added. The resulting solution was lyophilized to give 7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylic acid hydrogensulfate (81 mg) as an amorphous solid.

$^1$H-NMR(D$_2$O) δ 1.59 (3H, s), 1.59 (3H, s), 3.24 (1H, d, J=17.9 Hz), 3.26 (4H, t, J=6.5 Hz), 3.46 (1H, d, J=17.9 Hz), 3.70 (4H, t, J=6.5 Hz), 3.70 (3H, s), 5.06 (1H, d, J=15.6 Hz), 5.23 (1H, d, J=15.6 Hz), 5.24 (1H, d, J=5.0 Hz), 5.85 (1H, d, J=5.0 Hz), 7.91 (1H, s)

EXAMPLE 3

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (647 mg) in N,N-dimethylformamide (1.5 ml) was added 1,3-bis(trimethylsilyl)urea (971 mg) and the mixture was stirred at room temperature for 30 minutes. To the solution was added potassium iodide (221 mg) and the mixture was stirred at room temperature for 30 minutes. To the reaction mixture was added a solution of tert-butyl (2-{N-({[1-methyl-5-(tritylamino)pyrazol-4-yl]amino}carbonyl)-N-[3-(tritylamino)propyl]amino}-ethyl)carbamate (918 mg) in N,N-dimethylformamide (2 ml) and the whole mixture was stirred at 45–50° C. for 2.5 hours. To the resulting reaction mixture was added ethyl acetate (50 ml) and the solution was washed successively with water (50 ml), 10% aqueous sodium trifluoroacetate (50 ml×2) and brine (50 ml), dried over anhydrous sodium sulfate and filtered. The filtrate was concentrated to about 8 ml in vacuo. The concentrate was poured into diisopropyl ether (60 ml) and the resulting precipitate was collected by filtration and dried in vacuo. To a solution of the solid in methylene chloride (3.7 ml) were added anisole (1.3 ml) and trifluoroacetic acid (3.7 ml).

The resulting solution was stirred at room temperature for 4 hours and poured into diisopropyl ether (60 ml). The resulting precipitate was collected by filtration and dried in vacuo to give a crude product (995 mg), which was purified by preparative high-performance liquid chromatography (HPLC) utilizing ODS column. The eluate containing a desired product was concentrated to about 30 ml in vacuo. The concentrate was adjusted to about pH 3 with concentrated hydrochloric acid and chromatographed on Diaion (registered trademark) HP-20 (Mitsubishi Chemical Corporation) eluting with 30% aqueous 2-propanol. The eluate was concentrated to about 10 ml in vacuo and lyophilized to give 7β-[(Z)-2-(5-amino-1,2,4-thiadiazol-3-yl)-2-(1-carboxy-1-methylethoxyimino)acetamido]-3-[3-amino-4-({[N-(2-aminoethyl)-N-(3-aminopropyl)amino]carbonyl}amino)-2-methyl-1-pyrazolio]methyl-3-cephem-4-carboxylate (62 mg) as an amorphous solid.

$^1$H-NMR(D$_2$O) δ 1.52 (6H, s), 1.95–2.10 (2H, m), 3.04 (2H, t, J=7.3 Hz), 3.15–3.29 (2H, m), 3.21 (1H, d, J=17.9 Hz), 3.39–3.50 (2H, m), 3.52 (1H, d, J=17.9 Hz), 3.59–3.70 (2H, m), 3.74 (3H, s), 4.95 (1H, d, J=15.1 Hz), 5.09 (1H, d, J=15.1 Hz), 5.27 (1H, d, J=5.0 Hz), 5.82 (1H, d, J=5.0 Hz), 7.83 (1H, s)

PREPARATION 11

To a suspension of 1,3-diamino-2-propanol (75 g) in water (370 ml) and tetrahydrofuran (500 ml) was added triethylamine (290 ml) dropwise under stirring. To the mixture was added a solution of di-tert-butyl dicarbonate (381 g) in tetrahydrofuran (250 ml) dropwise under cooling on an ice-water bath at a temperature below 25° C. over 40 minutes, and the mixture was stirred overnight at room temperature. The mixture was made acidic (pH=3) with 1N aqueous hydrochloric acid and extracted with ethyl acetate (1 L). The organic layer was washed with saturated aqueous sodium hydrogencarbonate solution and brine, and dried over anhydrous magnesium sulfate. Concentration under reduced pressure gave a residue, which was triturated with ethyl acetate (150 ml)—hexane (700 ml) to give di-tert-butyl (2-hydroxy-1,3-propanediyl)biscarbamate (164 g) as a white solid.

ESI Mass: 313.3 [M+Na]$^+$ (positive) $^1$H-NMR(CDCl$_3$) δ 1.44 (18H, s), 3.0–3.4 (4H, m), 3.6–3.9 (2H, m), 5.1–5.2 (2H, m)

PREPARATION 12

To a solution of di-tert-butyl (2-hydroxy-1,3-propanediyl) biscarbamate (200 g) in methylene chloride (1.2 L) was added triethylamine (384 ml) under cooling on an ice-water bath and then a solution of methanesulfonyl chloride (64 ml) in methylene chloride (300 ml) was dropwise added at a temperature below 15° C. The mixture was stirred at the same temperature for 1.5 hours and quenched with saturated aqueous sodium hydrogencarbonate solution (200 ml). The organic layer was made acidic (pH=3) with diluted hydrochloric acid, and washed with saturated aqueous sodium hydrogencarbonate solution and brine, and dried over anhydrous magnesium sulfate. Concentration under reduced pressure gave a residue, which was triturated with ethyl acetate (100 ml)—hexane (500 ml) to give 2-[(tert-butoxycarbonyl)amino]-1-{[(tert-butoxycarbonyl)amino]methyl}ethyl methanesulfonate (202 g) as a white solid.

ESI Mass: 391.1 [M+Na]$^+$ (positive) $^1$H-NMR(CDCl$_3$) δ 1.45 (18H, s), 3.09 (3H, s), 3.2–3.4 (2H, m), 3.4–3.6 (2H, m), 4.6–4.8 (1H, m), 5.0–5.3 (2H, m)

PREPARATION 13

To a solution of 2-[(tert-butoxycarbonyl)amino]-1-{[(tert-butoxycarbonyl)amino]methyl}ethyl methanesulfonate (200 g) was added phthalimide potassium salt (101 g), and the mixture was stirred overnight at 75° C. To the reaction mixture was added water (6 L), and the mixture was extracted with ethyl acetate (6 L). The organic layer was washed with water (1.5 L×3) and brine, and dried over anhydrous magnesium sulfate. Concentration under reduced pressure gave a residue, which was triturated with hexane (500 ml). The collected crystals was washed with hexane (100 ml×3), and the mother liquor was recrystallized from hexane (300 ml) and combined with the former crystals to give di-tert-butyl [2-(1,3-dioxo-1,3-dihydro-2H-isoindol-2-yl)-1,3-propanediyl]biscarbamate (168 g).

ESI Mass: 442.1 [M+Na]$^+$ (positive) $^1$H-NMR(CDCl$_3$) δ 1.32 (18H, s), 3.4–3.6 (2H, m), 3.6–3.9 (2H, m), 4.4–4.6 (1H, m), 4.8–5.2 (2H, m), 7.6–7.9 (4H, m)

PREPARATION 14

Di-tert-butyl [2-(1,3-dioxo-1,3-dihydro-2H-isoindol-2-yl)-1,3-propanediyl]biscarbamate (144 g) was suspended in ethanol (1.5 L), and hydrazine monohydrate (19.8 ml) was added dropwise to the suspension under cooling on an ice-water bath. The mixture was refluxed for 5 hours, and cooled to 5° C. on an ice-water bath. The precipitate was filtered off, and the filtrate was concentrated under reduced pressure and recrystallized from hexane (500 ml)—ethyl acetate (100 ml) to give di-tert-butyl (2-amino-1,3-propanediyl)biscarbamate (44.1 g) as crystals. The mother liquor (31.3 g), which proved to be satisfactorily pure by thin layer chromatography, was also used for the next reaction.

ESI Mass: 290.4 [M+H]$^+$ (positive) $^1$H-NMR(DMSO-d$_6$) δ 1.44 (18H, s), 2.8–3.3 (5H, m), 4.8–5.3 (4H, m)

PREPARATION 15

Di-tert-butyl {2-[({[1-methyl-5-(tritylamino)pyrazol-4-yl]amino}carbonyl)amino]-1,3-propanediyl}biscarbamate was obtained in the same manner as in Preparation 7 from phenyl [1-methyl-5-(tritylamino)pyrazol-4-yl]carbamate and di-tert-butyl (2-amino-1,3-propanediyl)biscarbamate except that N,N-dimethylformamide was used instead of chloroform.

ESI Mass: 692.3 [M+Na]$^+$ (positive) $^1$H-NMR(DMSO-d$_6$) δ 1.37 (18H, s), 2.69 (3H, s), 2.8–3.1 (4H, m), 3.5–3.7 (1H, m), 5.72 (1H, s), 5.83 (1H, d, J=7.5 Hz), 6.6–6.8 (2H, m)

EXAMPLE 4

7β-[(Z)-2-(5-Amino-1,2,4-thiadiazol-3-yl)-2-(1-carboxy-1-methylethoxyimino)acetamido]-3-(3-amino-4-{3-[2-amino-1-(aminomethyl)ethyl]ureido}-2-methyl-1-pyrazolio)methyl-3-cephem-4-carboxylic acid hydrogensulfate The title compound was obtained in the same manner as in Example 1 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl ({2-[({[1-methyl-5-(tritylamino) pyrazol-4-yl]amino}carbonyl)amino]-1,3-propanediyl}biscarbamate except that after chromatography on Diaion (registered trademark) HP20 and concentration in vacuo, an equivalent of sulfuric acid was added before lyophilization.

ESI Mass: 696.1 [M (free)+H]$^+$ (positive) $^1$H-NMR(D$_2$O) δ 1.62 (6H, s), 3.0–3.6 (6H, m), 3.71 (3H, s), 4.2–4.5 (1H, m), 5.04 and 5.24 (2H, ABq, J=15.8 Hz), 5.26 (1H, d, J=4.8 Hz), 5.87 (1H, d, J=4.7 Hz), 7.96 (1H, s)

PREPARATION 16

To a stirred solution of 1-methylpyrazole-4,5-diamine sulfate (2.1 g) and 3-ethoxy-3-oxopropanoic acid (1.32 g) in methylene chloride (10 ml) and tetrahydrofuran (10 ml) was added N-(3-dimethylaminopropyl)-N'-ethylcarbodiimide hydrochloride (3.83 g) and N-ethyldiisopropylamine (6.96 ml), and the mixture was stirred overnight. The solvent was removed under reduced pressure, and the residue which includes ethyl 3-[(5-amino-1-methylpyrazol-4-yl)amino]-3-oxopropanoate was used for the next reaction without further purification.

PREPARATION 17

The crude product of ethyl 3-[(5-amino-1-methylpyrazol-4-yl)amino]-3-oxopropanoate obtained in Preparation 16 was dissolved in N,N-dimethylformamide (20 ml), and trityl chloride (5.52 g) and triethylamine (4.14 ml) were added under stirring. The mixture was stirred overnight and quenched with water (10 ml). The whole mixture was extracted with ethyl acetate, washed with water and brine, and dried over anhydrous magnesium sulfate. Concentration under reduced pressure gave a residual oil, which was chromatographed on silica gel eluted with methylene chloride-ethyl acetate (2:3) to give ethyl 3-{[1-methyl-5-(tritylamino)pyrazol-4-yl]amino}-3-oxopropanoate (1.23 g).

ESI Mass: 491.2 $[M+Na]^+$ (positive), 467.3 $[M-H]^-$ (negative) $^1$H-NMR(DMSO-$d_6$) δ 1.18 (3H, t, J=7.1 Hz), 2.75 (3H, s), 3.04 (2H, s), 4.07 (2H, q, J=7.1 Hz)

PREPARATION 18

To a stirred solution of ethyl 3-{[1-methyl-5-(tritylamino)pyrazol-4-yl]amino}-3-oxopropanoate (1.3 g) in tetrahydrofuran (30 ml) was added 1N aqueous sodium hydroxide solution (3.1 ml) and the mixture was stirred at room temperature for 3 hours. Tetrahydrofuran was removed in vacuo and the residue was made acidic with diluted aqueous citric acid solution. The resulting precipitate was collected by filtration and dried under reduced pressure to give 3-{[1-methyl-5-(tritylamino)pyrazol-4-yl]amino}-3-oxopropanoic acid (1.22 g).

ESI Mass: 463.2 $[M+Na]^+$ (positive) $^1$H-NMR(DMSO-$d_6$) δ 2.74 (3H, s), 2.95 (2H, s), 5.56 (1H, s), 7.0–7.4 (16H, m), 8.54 (1H, s), 12.0–13.0 (1H, brs)

PREPARATION 19

A mixture of 3-{[1-methyl-5-(tritylamino)pyrazol-4-yl]amino}-3-oxopropanoic acid (600 mg), di-tert-butyl (2-amino-1,3-propanediyl)biscarbamate (434 mg) and N-(3-dimethylaminopropyl)-N'-ethylcarbodiimide hydrochloride (522 mg) in tetrahydrofuran (12 ml) and methylene chloride (6 ml) was stirred overnight at room temperature. Water was added and the whole mixture was extracted with ethyl acetate. The organic layer was washed with water and brine, and dried over anhydrous magnesium sulfate. Concentration under reduced pressure gave a residue, which was triturated with diisopropyl ether-ethyl acetate (2:1) to give di-tert-butyl {2-[(3-{[1-methyl-5-(tritylamino)pyrazol-4-yl]amino}-3-oxopropanoyl)amino]-1,3-propanediyl}biscarbamate (699 mg) as a white solid.

ESI Mass: 733.9 $[M+Na]^+$ (positive) $^1$H-NMR(DMSO-$d_6$) δ 1.37 (18H, s), 2.73 (3H, s), 2.83 (2H, s), 2.8–3.2 (4H, m), 3.6–3.9 (1H, m), 5.60 (1H, s), 6.6–6.8 (2H, m), 7.1–7.4 (16H, m), 7.80 (1H, d, J=8.2 Hz), 8.69 (1H, s)

EXAMPLE 5

7β-[(Z)-2-(5-Amino-1,2,4-thiadiazol-3-yl)-2-(1-carboxy-1-methylethoxyimino)acetamido]-3-{3-amino-4-[(3-{[2-amino-1-(aminomethyl)ethyl]amino}-3-oxopropanoyl)amino]-2-methyl-1-pyrazolio}methyl-3-cephem-4-carboxylate The title compound was obtained in the same manner as in Example 1 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl {2-[(3-{[1-methyl-5-(tritylamino)pyrazol-4-yl]amino}-3-oxopropanoyl)amino]-1,3-propanediyl}biscarbamate.

$^1$H-NMR($D_2O$) δ 1.54 (6H, s), 3.0–3.7 (8H, m), 3.78 (3H, s), 4.4–4.7 (1H, m), 4.9–5.2 (2H, m), 5.27 (1H, d, J=4.9 Hz), 5.85 (1H, d, J=4.7 Hz), 8.03 (1H, s)

PREPARATION 20

To a suspension of (2S)-2-{[(benzyloxy)carbonyl]amino}-3-[(tert-butoxycarbonyl)amino]propanoic acid (1.695 g) and 1-methyl-1H-pyrazole-4,5-diamine sulfate (1.05 g) in water (16 ml) were added triethylamine (1.4 ml) and N-(3-dimethylaminopropyl)-N'-ethylcarbodiimide hydrochloride (1.73 g). The mixture was stirred at room temperature for 2 hours. The resulting suspension was extracted with a mixed solvent of ethyl acetate and tetrahydrofuran. The extract was washed with water and brine, dried over anhydrous magnesium sulfate, filtered and concentrated in vacuo to give 2-benzyl 1-tert-butyl {(2S)-3-[(5-amino-1-methyl-1H-pyrazol-4-yl)amino]-3-oxo-1,2-propanediyl}biscarbamate (1.78 g) as a solid.

$^1$H-NMR(DMSO-$d_6$) δ 1.36 (9H, s), 3.20–3.35 (2H, m), 3.50 (3H, s), 4.10–4.25 (1H, m), 4.92 (2H, brs), 5.00 and 5.08 (2H, ABq, J=12.7 Hz), 6.84 (1H, t, J=5.5 Hz), 7.15 (1H, s), 7.26 (1H, d, J=8.1 Hz), 7.27–7.37 (5H, m), 9.20 (1H, brs)

PREPARATION 21

A solution of 2-benzyl 1-tert-butyl {(2S)-3-[(5-amino-1-methyl-1H-pyrazol-4-yl)amino]-3-oxo-1,2-propanediyl}biscarbamate (1.58 g) in tetrahydrofuran (28 ml) was treated with 10% palladium on carbon (0.75 g) under a hydrogen atmosphere for 2 hours at room temperature. After the catalyst was filtered off, the filtrate was concentrated in vacuo to give a crude oil, which was dissolved in tetrahydrofuran (28 ml). To the solution were added triethylamine (2.04 ml) and di-tert-butyl ({[(trifluoromethyl)sulfonyl]imino}methylene)biscarbamate (2.86 g) successively at room temperature. The mixture was stirred at room temperature overnight. To the reaction mixture was added water to quench the reaction. The mixture was extracted with ethyl acetate. The organic layer was washed with water and brine. The extract was dried over anhydrous magnesium sulfate, filtered and concentrated in vacuo. The residue was purified by silica gel column chromatography to give di-tert-butyl {[((1S)-2-[(5-amino-1-methyl-1H-pyrazol-4-yl)amino]-1-{[(tert-butoxycarbonyl)amino]methyl}-2-oxoethyl)amino]methylylidene}biscarbamate (1.53 g) as an amorphous solid.

$^1$H-NMR(DMSO-$d_6$) δ 1.36 (9H, s), 1.40 (9H, s), 1.48 (9H, s), 3.25–3.60 (3H, m), 3.51 (3H, s), 4.60–4.75 (1H, m), 4.96 (2H, brs), 7.05 (1H, t, J=6.1 Hz), 7.11 (1H, s), 9.25 (1H, d, J=7.5 Hz), 11.47 (1H, brs)

PREPARATION 22

To a solution of di-tert-butyl {[((1S)-2-[(5-amino-1-methyl-1H-pyrazol-4-yl)amino]-1-{[(tert-butoxycarbonyl)amino]methyl}-2-oxoethyl)amino]methylylidene}biscarbamate (1.72 g) in dichloromethane (17 ml) was added trityl chloride (931 mg). To the mixture was added triethylamine (0.53 ml) dropwise. The mixture was stirred at room temperature for 1 hour. The reaction mixture was dissolved in ethyl acetate. The solution was washed with water and brine. The extract was dried over anhydrous magnesium sulfate, filtered and concentrated in vacuo. The residue was purified by column chromatography on silica gel to give di-tert-butyl {(Z)-[((1S)-{[(tert-butoxycarbonyl)amino]methyl}-2-{[1-methyl-5-(tritylamino)-1H-pyrazol-4-yl]amino}-2-oxoethyl)amino]methylylidene}biscarbamate (2.25 g).

ESI Mass: 783 [M+H]$^+$ $^1$H-NMR(DMSO-d$_6$) δ 1.35 (9H, s), 1.42 (9H, s), 1.47 (9H, s), 2.75 (3H, s), 2.90–3.40 (3H, m), 4.35–4.50 (1H, m), 5.65 (1H, s), 6.92 (1H, t, J=5.8 Hz), 7.14–7.31 (16H, m), 8.48 (1H, s), 8.56 (1H, d, J=7.6 Hz)

EXAMPLE 6

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (681 mg) in N-methylmorpholine (2 ml) was added 1,3-bis(trimethylsilyl)urea (1.02 g) and the mixture was stirred at room temperature for 30 minutes. To the solution was added potassium iodide (183 mg) and the mixture was stirred at room temperature for 30 minutes. To the reaction mixture was added di-tert-butyl {(Z)-[((1S)-1-{[(tert-butoxycarbonyl)amino]methyl}-2-{[1-methyl-5-(tritylamino)-1H-pyrazol-4-yl]amino}-2-oxoethyl)amino]methylylidene}biscarbamate (939 mg) and the whole mixture was stirred at 35° C. overnight. To the resulting reaction mixture was added ethyl acetate (1.7 L) and the mixture was washed successively with water, 10% aqueous sodium thiosulfate solution, 10% aqueous sodium trifluoroacetate solution and brine, dried over magnesium sulfate and filtered. The filtrate was concentrated to about 1 L in vacuo. The concentrate was poured into diisopropyl ether and the resulting precipitate was collected by filtration and dried in vacuo. To a solution of the solid in methylene chloride (3.6 ml) were added anisole (1.2 ml) and trifluoroacetic acid (3.6 ml). The resulting solution was stirred at room temperature for 4 hours and poured into diisopropyl ether. The resulting precipitate was collected by filtration and dried in vacuo to give a crude product. The crude product was purified by preparative HPLC utilizing ODS column. The eluate containing a desired product was concentrated to about 30 ml in vacuo. The concentrate was adjusted to about pH 3 by addition of concentrated hydrochloric acid and chromatographed on Diaion (registered trademark) HP-20 eluting with 30% aqueous 2-propanol. The eluate was concentrated to about 30 ml in vacuo and 1 equivalent of 0.1M aqueous sulfuric acid solution was added. The mixture was lyophilized to give 7β-[(Z)-2-(5-amino-1,2,4-thiadiazol-3-yl)-2-(1-carboxy-1-methylethoxyimino)acetamido]-3-(3-amino-4-{[(2S)-3-amino-2-(guanidino)propanoyl]amino}-2-methyl-1-pyrazolio)methyl-3-cephem-4-carboxylic acid hydrogensulfate (115 mg) as an amorphous solid.

ESI Mass: 729.8 [M+Na]$^+$ IR(KBr) 1778, 1664, 1527, 1155, 1109 cm$^{-1}$ $^1$H-NMR(DMSO-d$_6$) δ 1.61 (6H, s), 3.20 and 3.43 (2H, ABq, J=17.8 Hz), 3.72 (3H, s), 4.55–4.80 (3H, m), 5.00 and 5.25 (1H, ABq, J=15.8 Hz), 5.24 (1H, d, J=4.9 Hz), 5.87 (1H, d, J=4.9 Hz), 7.97 (1H, s)

PREPARATION 23

To a suspension of phenyl (4,5,6,7-tetrahydropyrazolo[1,5-a]pyrimidin-3-yl)carbamate (5 g) in methylene chloride (150 ml) were added di-tert-butyl [iminobis(2,1-ethanediyl)]biscarbamate (8.81 g) and triethylamine (1.96 g) at room temperature, and the mixture was stirred under reflux for 19 hours. The mixture was concentrated in vacuo, and the residue was purified by column chromatography on silica gel to give di-tert-butyl [{[(4,5,6,7-tetrahydropyrazolo[1,5-a]pyrimidin-3-ylamino)carbonyl]imino}bis(2,1-ethanediyl)]biscarbamate (7 g).

$^1$H-NMR(DMSO-d$_6$) δ 1.37 (18H, s), 1.94–1.99 (2H, m), 2.94–3.32 (10H, m), 3.90–3.96 (2H, m), 5.38 (1H, brs), 6.83–6.92 (1H, m), 6.98 (1H, s), 7.49 (1H, s)

EXAMPLE 7

7β-[(Z)-2-(5-Amino-1,2,4-thiadiazol-3-yl)-2-(1-carboxy-1-methylethoxyimino)acetamido]-3-[3-({[bis(2-aminoethyl)amino]carbonyl}amino)-4,5,6,7-tetrahydro-1-pyrazolo[1,5-a]pyrimidinio]methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl [{[(4,5,6,7-tetrahydropyrazolo[1,5-a]pyrimidin-3-ylamino)carbonyl]imino}bis(2,1-ethanediyl)]biscarbamate.

$^1$H-NMR(DMSO-d$_6$) δ 1.61 (6H, s), 2.04–2.22 (2H, m), 3.19–3.56 (10H, m), 3.65–3.78 (2H, m), 4.04–4.18 (2H, m), 4.88–5.22 (2H, m), 5.24 (1H, d, J=4.7 Hz), 5.86 (1H, d, J=4.7 Hz), 7.85 (1H, s)

PREPARATION 24

To a stirred solution of phenyl [1-(2-hydroxyethyl)-5-(tritylamino)-1H-pyrazol-4-yl]carbamate (9 g) in N,N-dimethylformamide (63 ml) were added di-tert-butyl [iminobis(2,1-ethanediyl)]biscarbamate (5.95 g) and triethylamine (2.74 ml), and the mixture was stirred at room temperature for 3 hours. Water was added to the reaction mixture and the whole mixture was extracted with ethyl acetate. The extract was washed with water and brine and dried over anhydrous magnesium sulfate. Concentration under reduced pressure gave a crude product, which was triturated with ethyl acetate-diisopropyl ether (1:3). The resulting solid was collected by filtration to give di-tert-butyl [[({[1-(2-hydroxyethyl)-5-(tritylamino)-1H-pyrazol-4-yl]amino}carbonyl)imino]bis(2,1-ethanediyl)]biscarbamate (11.7 g).

$^1$H-NMR(DMSO-d$_6$) δ 1.36 (18H, s), 2.9–3.0 (4H, m), 3.0–3.15 (4H, m), 3.30–3.45 (4H, m), 4.70–4.78 (1H, m), 5.54 (1H, brs), 6.70–6.85 (1H, m), 7.04 (1H, s), 7.00–7.35 (16H, m)

EXAMPLE 8

7β-[(Z)-2-(5-Amino-1,2,4-thiadiazol-3-yl)-2-(1-carboxy-1-methylethoxyimino)acetamido]-3-[3-amino-4-({[bis(2-aminoethyl)amino]carbonyl}amino)-2-(2-hydroxyethyl)-1-pyrazolio]methyl-3-cephem-4-carboxylic acid hydrogensulfate The title compound was obtained in the same manner as in Example 6 from 4-methoxybenzyl 7β-[(Z)-2-(5-amino-1, 2,4-thiadiazol-3-yl)-2-(1-tert-butoxycarbonyl-1-methyl-ethoxyimino)acetamido]-3-chloromethyl-3-cephem-4-carboxylate and di-tert-butyl [[({[1-(2-hydroxyethyl)-5-(tritylamino)-1H-pyrazol-4-yl]amino}carbonyl)imino]bis(2,1-ethanediyl)]biscarbamate.

$^1$H-NMR(D$_2$O) δ 1.61 (6H, s), 3.22 and 3.51 (2H, ABq, J=17.9 Hz), 3.18–3.35 (4H, m), 3.65–3.80 (4H, m), 3.80–3.95 (2H, m), 4.32–4.47 (2H, m), 5.09 and 5.19 (2H, ABq, J=15.2 Hz), 5.26 (1H, d, J=4.9 Hz), 5.86 (1H, d, J=4.9 Hz), 7.97 (1H, s)

PREPARATION 25

A mixture of 1-methyl-1H-pyrazol-5-amine (2 g) and di-tert-butyl (2-oxo-1,3-propanediyl)biscarbamate (5.9 g) in acetic acid (20 ml) was stirred at 70° C. for 8 hours. To the reaction mixture was added ethyl acetate, and the mixture was neutralized with saturated aqueous sodium hydrogencarbonate solution. The organic layer was dried over anhydrous magnesium sulfate and concentrated in vacuo. The residue was purified by column chromatography on silica gel (ethyl acetate—ethyl acetate:ethanol=10:1) to give the desired product (1 g). The obtained compound was dissolved in methanol (20 ml) and 10% Pd/C (0.5 g) was added, and the mixture was hydrogenated under balloon pressure for 5 hours. The reaction mixture was filtered through a bed of Celite, and the filtrate was concentrated in vacuo to give di-tert-butyl [2-(5-amino-1-methyl-1H-pyrazol-4-yl)-1,3-propanediyl]biscarbamate (1 g).

$^1$H-NMR(DMSO-d$_6$) δ 1.36 (18H, s), 2.55–2.75 (1H, m), 2.85–3.10 (4H, m), 3.48 (3H, s), 4.82 (2H, brs), 6.50–6.70 (2H, m), 6.90 (1H, s)

PREPARATION 26

To a solution of di-tert-butyl [2-(5-amino-1-methyl-1H-pyrazol-4-yl)-1,3-propanediyl]biscarbamate (1.27 g) in methylene chloride (10 ml) were added 1,8-diazabicyclo[5.4.0]undec-7-ene (1.05 g) and trityl chloride (1.44 g) at room temperature. The mixture was stirred for 2 hours. Water was added and the mixture was extracted with ethyl acetate. The organic layer was dried over anhydrous magnesium sulfate and concentrated in vacuo. The residue was purified by column chromatography on silica gel (ethyl acetate:hexane=1:1) to give di-tert-butyl {2-[1-methyl-5-(tritylamino)-1H-pyrazol-4-yl]-1,3-propanediyl}biscarbamate (1.7 g).

$^1$H-NMR(DMSO-d$_6$) δ 1.36 (18H, s), 2.4–2.75 (5H, m), 2.61 (3H, s), 5.70 (1H, brs), 6.05–6.20 (2H, m), 6.99 (1H, s), 7.05–7.30 (15H, m)

EXAMPLE 9

7β-[(Z)-2-(5-Amino-1,2,4-thiadiazol-3-yl)-2-(1-carboxy-1-methylethoxyimino)acetamido]-3-(3-amino-4-[2-amino-1-(aminomethyl)ethyl]-2-methyl-1-pyrazolio}methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl (2-[1-methyl-5-(tritylamino)-1H-pyrazol-4-yl]-1,3-propanediyl)biscarbamate.

$^1$H-NMR(D$_2$O) δ 1.62 (6H, s), 3.15–3.70 (7H, m), 3.72 (3H, s), 4,99 (1H, d, J=16.2 Hz), 5.22 (1H, d, J=16.2 Hz), 5.27 (1H, d, J=4.8 Hz), 5.86 (1H, d, J=4.8 Hz), 8.03 (1H, s)

PREPARATION 27

To a suspension of (2S)-2-{[(benzyloxy)carbonyl]amino}-4-[(tert-butoxycarbonyl)amino]butanoic acid (6.0 g) and 1-methyl-1H-pyrazole-4,5-diamine sulfate (3.57 g) in water (60 ml) were added triethylamine (4.75 ml) and N-(3-dimethylaminopropyl)-N'-ethylcarbodiimide hydrochloride (5.88 g). The mixture was stirred at room temperature for 2 hours. The resulting suspension was extracted with a mixed solvent of ethyl acetate and tetrahydrofuran. The extract was washed with water and brine, dried over anhydrous magnesium sulfate, filtered and concentrated in vacuo. To a solution of the residue in dichloromethane (60 ml) was added trityl chloride (4.74 g). To the mixture was added triethylamine (4.75 ml) dropwise. The mixture was stirred at room temperature for 1 hour. The reaction mixture was dissolved in ethyl acetate. The solution was washed with water and brine. The organic layer was dried over anhydrous magnesium sulfate, filtered and concentrated in vacuo. The residue was purified by column chromatography on silica gel to give benzyl [(1S)-3-[(tert-butoxycarbonyl)amino]-1-({[1-methyl-5-(tritylamino)-1H-pyrazol-4-yl]amino}carbonyl)propyl]carbamate (5.55 g).

ESI Mass: 689.31 [M+H]$^+$ $^1$H-NMR(DMSO-d$_6$) δ 1.39 (9H, s), 1.40–1.75 (2H, m), 2.81 (3H, s), 2.82–3.00 (3H, m), 3.70–3.90 (1H, m), 5.00 and 5.08 (2H, ABq, J=12.6 Hz), 5.77 (1H, s), 6.72 (1H, t-like), 7.15–7.47 (22H, m), 8.25 (1H, brs)

PREPARATION 28

A solution of benzyl [(1S)-3-[(tert-butoxycarbonyl)amino]-1-({[1-methyl-5-(tritylamino)-1H-pyrazol-4-yl]amino}carbonyl)propyl]carbamate (1.38 g) and di-tert-butyl dicarbonate (0.87 g) in tetrahydrofuran (28 ml) was treated with 10% palladium on carbon (0.70 g) under a hydrogen atmosphere for 3 hours at room temperature. After the catalyst was filtered off, the filtrate was concentrated in vacuo to give a crude oil. The oil was purified by column chromatography on silica gel to give tert-butyl [(1S)-3-[(tert-butoxycarbonyl)amino]-1-({[1-methyl-5-(tritylamino)-1H-pyrazol-4-yl]amino}carbonyl)propyl]carbamate (1.00 g) as an amorphous solid.

ESI Mass: 655.34 [M+H]$^+$ $^1$H-NMR(DMSO-d$_6$) δ 1.39 (18H, s), 2.80–2.95 (3H, m), 2.83 (3H, s), 3.65–3.85 (1H, m), 5.78 (1H, brs), 6.69 (1H, t-like), 6.89 (1H, d, J=8.1 Hz), 7.15–7.32 (16H, m), 8.20 (1H, brs)

EXAMPLE 10

7β-[(Z)-2-(5-Amino-1,2,4-thiadiazol-3-yl)-2-(1-carboxy-1-methylethoxyimino)acetamido]-3-[3-amino-4-{[(2S)-2,4-diaminobutanoyl]amino}-2-methyl-1-pyrazolio]methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido)-3-chloromethyl-3-cephem-4-carboxylate and tert-butyl [(1S)-3-[(tert-butoxycarbonyl)amino]-1-({[1-methyl-5-(tritylamino)-1H-pyrazol-4-yl]amino}carbonyl)propyl]carbamate.

ESI Mass: 681.2 [M+H]$^+$ IR(KBr) 1772, 1527, 1402, 1109 cm$^{-1}$ $^1$H-NMR(DMSO-d$_6$) δ 1.57 (6H, s), 2.30–2.50 (2H, m), 3.20 (2H, t, J=8.4 Hz), 3.20 and 3.48 (2H, ABq, J=17.7 Hz), 3.73 (3H, s), 4.35 (1H, t, J=6.7 Hz), 4.98 and 5.21 (1H, ABq, J=15.3 Hz), 5.25 (1H, d, J=4.8 Hz), 5.85 (1H, d, J=4.8 Hz), 8.14 (1H, s)

PREPARATION 29 tert-Butyl ((3S)-4-[(5-amino-1-methyl-1H-pyrazol-4-yl)amino]-3-{[(benzyloxy)carbonyl]amino}-4-oxobutyl)carbamate The title compound was obtained in the same manner as in Preparation 20 from (2S)-2-{[(benzyloxy)carbonyl]amino}-4-[(tert-butoxycarbonyl)amino]butanoic acid.

$^1$H-NMR(DMSO-$d_6$) δ 1.37 (9H, s), 1.55–1.90 (2H, m), 2.85–3.08 (2H, m), 3.51 (3H, s), 4.00–4.18 (1H, m), 4.91 (1H, brs), 5.03 (2H, s), 6.77 (1H, t-like), 7.18 (1H, s), 7.25–7.40 (5H, m), 7.54 (1H, d, J=7.8 Hz), 9.22 (1H, brs)

PREPARATION 30

A solution of tert-butyl ((3S)-4-[(5-amino-1-methyl-1H-pyrazol-4-yl)amino]-3-{[(benzyloxy)carbonyl]amino}-4-oxobutyl)carbamate (1.51 g) in tetrahydrofuran (30 ml) was treated with 10% palladium on carbon (0.75 g) under a hydrogen atmosphere for 2 hours at room temperature. After the catalyst was filtered off, the filtrate was concentrated in vacuo to give a crude oil, which was dissolved in tetrahydrofuran (30 ml). To the solution were added triethylamine (1.94 ml) and di-tert-butyl ({[(trifluoromethyl)sulfonyl]-imino}methylene)biscarbamate (2.64 g) successively at room temperature. The mixture was stirred at room temperature overnight. To the reaction mixture was added water to quench the reaction. The mixture was extracted with ethyl acetate. The organic layer was washed with water and brine. The extract was dried over anhydrous magnesium sulfate, filtered and concentrated in vacuo. To a solution of the residue in dichloromethane (30 ml) was added trityl chloride (942 mg). To the mixture was added triethylamine (1.9 ml) dropwise. The mixture was stirred at room temperature overnight. The reaction mixture was dissolved in ethyl acetate. The solution was washed with water and brine. The extract was dried over anhydrous magnesium sulfate, filtered and concentrated in vacuo. The residue was purified by column chromatography on silica gel to give di-tert-butyl ((Z)-{[(1S)-3-[(tert-butoxycarbonyl)amino]-1-({[1-methyl-5-(tritylamino)-1H-pyrazol-4-yl]amino}carbonyl)propyl]amino}methylylidene)biscarbamate (1.95 g).

$^1$H-NMR(DMSO-$d_6$) δ 1.38 (9H, s), 1.42 (9H, s), 1.48 (9H, s), 1.50–1.85 (2H, m), 2.75–3.12 (2H, m), 2.79 (3H, s), 4.30–4.48 (1H, m), 5.62 (1H, s), 6.67 (1H, t-like), 7.14–7.29 (16H, m), 8.54 (1H, d, J=7.6 Hz), 8.61 (1H, brs)

EXAMPLE 11

7β-[(Z)-2-(5-Amino-1,2,4-thiadiazol-3-yl)-2-(1-carboxy-1-methylethoxyimino)acetamido]-3-(3-amino-4-{[(2S)-4-amino-2-(guanidino)butanoyl]amino}-2-methyl-1-pyrazolio)methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl ((Z)-{[(1S)-3-[(tert-butoxycarbonyl)amino]-1-({[1-methyl-5-(tritylamino)-1H-pyrazol-4-yl]amino}carbonyl)propyl]amino}methylylidene)biscarbamate ESI Mass: 691.11 [M+H]$^+$ IR(KBr) 1776, 1668, 1525, 1111 cm$^{-1}$ $^1$H-NMR(DMSO-$d_6$) δ 1.60 (6H, s), 1.75–2.50 (2H, m), 3.19 and 3.41 (2H, ABq, J=17.9 Hz), 3.70 (3H, s), 4.96 and 5.22 (2H, ABq, J=15.5 Hz), 5.23 (1H, d, J=4.8 Hz), 5.86 (1H, d, J=4.8 Hz), 7.89 (1H, s)

PREPARATION 31

Dess-Martin periodinane (4.2 g) was dissolved in methylene chloride (75 ml), and tert-butyl ((3S)-3-hydroxy-4-{[1-methyl-5-(tritylamino)-1H-pyrazol-4-yl]amino}-4-oxobutyl)carbamate (5 g) was added to the solution. The whole mixture was stirred at room temperature for 30 minutes and quenched with 1N aqueous sodium hydroxide solution (70 ml) with stirring for 30 minutes. The whole mixture was extracted with ethyl acetate. The extract was washed with water and brine and dried over anhydrous magnesium sulfate. The solvent was evaporated under reduced pressure to give a crude product, which was purified by column chromatography on silica gel (ethyl acetate:methylene chloride=1:4) to give tert-butyl (4-{[1-methyl-5-(tritylamino)-1H-pyrazol-4-yl]amino}-3,4-dioxobutyl)carbamate (3.4 g).

ESI Mass: 576.2 [M+Na]$^+$ (positive) $^1$H-NMR(CDCl$_3$) δ 1.39 (9H, s), 2.7–2.9 (2H, m), 2.72 (3H, s), 3.1–3.3 (2H, m), 5.89 (1H, s), 6.7–7.0 (1H, m), 7.0–7.3 (15H, m), 7.39 (1H, s), 8.93 (1H, s)

PREPARATION 32

To a stirred solution of diethyl (cyanomethyl)phosphonate (704 mg) in tetrahydrofuran (20 ml) was added sodium hydride (159 mg, 60% oil suspension) under ice-cooling. The mixture was stirred for 45 minutes with warming to room temperature. tert-Butyl (4-{[1-methyl-5-(tritylamino)-1H-pyrazol-4-yl]amino}-3,4-dioxobutyl)carbamate (2 g) was added to the mixture, and the whole mixture was stirred at room temperature for 2 hours. Water was added to the mixture, and the whole mixture was extracted with ethyl acetate. The extract was washed with water and brine and dried over anhydrous magnesium sulfate. The solvent was evaporated under reduced pressure to give a residual oil, which was triturated with a small amount of ethyl acetate and diluted with diisopropyl ether. The resulting precipitate was collected by filtration to give tert-butyl [(3E)-4-cyano-3-({[1-methyl-5-(tritylamino)-1H-pyrazol-4-yl]amino}carbonyl)-3-buten-1-yl]carbamate (1.41 g).

ESI Mass: 599.3 [M+Na]$^+$ (positive) $^1$H-NMR(CDCl$_3$) δ 1.37 (9H, s), 2.4–2.6 (2H, m), 2.77 (3H, s), 2.9–3.1 (2H, m), 5.52 (1H, s), 5.82 (1H, s), 6.8–7.0 (1H, m), 7.0–7.4 (16H, m), 8.75 (1H, s)

PREPARATION 33

To a stirred solution of tert-butyl [(3E)-4-cyano-3-({[1-methyl-5-(tritylamino)-1H-pyrazol-4-yl]amino}carbonyl)-3-buten-1-yl]carbamate (1.4 g) and di-tert-butyl dicarbonate (795 mg) in tetrahydrofuran (10 ml) was added PtO$_2$ (110 mg), and the mixture was stirred under hydrogen atmosphere for 5 days. The insoluble PtO$_2$ was filtered off, and the filtrate was concentrated under reduced pressure. The residue was purified by column chromatography on silica gel (ethyl acetate:methylene chloride=1:1) to give di-tert-butyl [3-({[1-methyl-5-(tritylamino)-1H-pyrazol-4-yl]amino}carbonyl)-1,5-pentanediyl]biscarbamate (1.04 g).

ESI Mass: 705.3 [M+Na]$^+$ (positive) $^1$H-NMR(CDCl$_3$) δ 1.38 (18H, s), 1.4–1.6 (4H, m), 1.8–2.0 (1H, m), 2.6–2.8 (4H, m), 2.78 (3H, s), 5.86 (1H, s), 6.6–6.8 (2H, m), 7.1–7.4 (16H, m), 7.81 (1H, s)

EXAMPLE 12

7β-[(Z)-2-(5-Amino-1,2,4-thiadiazol-3-yl)-2-(1-carboxy-1-methylethoxyimino)acetamido]-3-[3-amino-4-{[4-amino-2-(2-aminoethyl)butanoyl]amino}-2-methyl-1-pyrazolio]methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl [3-({[(1-methyl-5-(tritylamino)-1H-pyrazol-4-yl]amino}carbonyl)-1,5-pentanediyl]biscarbamate.

ESI Mass: 740.3 [M+H]$^+$ (positive) $^1$H-NMR(D$_2$O) δ 1.54 (6H, s), 1.8–2.2 (4H, m), 2.6–2.9 (1H, m), 2.9–3.2 (4H, m), 3.18 and 3.57 (2H, ABq, J=17.7 Hz), 3.8–4.0 (2H, m), 4.3–4.5 (2H, m), 4.8–5.2 (2H, m), 5.30 (1H, d, J=4.8 Hz), 5.85 (1H, d, J=4.8 Hz), 8.14 (1H, s)

PREPARATION 34

To a stirred solution of 2-[(tert-butoxycarbonyl)amino]-1-{[(tert-butoxycarbonyl)amino]methyl}ethyl methanesulfonate (10 g) in dimethyl sulfoxide (100 ml) was added sodium cyanide (2 g) at room temperature and the whole mixture was stirred overnight at room temperature. Water was added to the reaction mixture and the whole mixture was extracted with ethyl acetate. The extract was washed with water and brine and dried over anhydrous magnesium sulfate. The solvent was removed under reduced pressure and the residual oil was purified by column chromatography on silica gel (ethyl acetate:hexane=1:5) to give di-tert-butyl (2-cyano-1,3-propanediyl)biscarbamate (4.04 g).

ESI Mass: 322.3 (M+Na)$^+$ (positive) $^1$H-NMR(CDCl$_3$) δ 1.44 (18H, s), 2.6–2.7 (2H, m), 3.2–3.6 (4H, m), 3.8–4.0 (1H, m)

PREPARATION 35

Di-tert-butyl (2-cyano-1,3-propanediyl)biscarbamate was dissolved in concentrated hydrochloric acid (13 ml) and acetic acid (13 ml), and the mixture was refluxed for 5 hours. The reaction mixture was cooled and the solvent was evaporated under reduced pressure. Tetrahydrofuran (20 ml) and water (20 ml) were added to the residual oil and the whole mixture was neutralized with 1N aqueous sodium hydroxide solution. Di-tert-butyl dicarbonate (6.12 g) and triethylamine (9.31 ml) were added to the mixture. The whole mixture was stirred overnight at room temperature. The solvent was removed under reduced pressure, and the aqueous layer was made acidic (pH=2) with 1N aqueous hydrochloric acid. The whole mixture was extracted with ethyl acetate, and the extract was dried over anhydrous magnesium sulfate and concentrated under reduced pressure to give 3-[(tert-butoxycarbonyl)amino]-2-{[(tert-butoxycarbonyl)amino]methyl}propanoic acid (480 mg).

ESI Mass: 341.2 [M+Na]$^+$ (positive)

PREPARATION 36

To a solution of 3-[(tert-butoxycarbonyl)amino]-2-{[(tert-butoxycarbonyl)amino]methyl}propanoic acid (476 mg) in methylene chloride (6 ml) were added hydroxybenzotriazole (222 mg) and N-(3-dimethylaminopropyl)-N'-ethylcarbodiimide hydrochloride (573 mg), and the mixture was stirred for 10 minutes. 1-Methyl-N$^5$-trityl-1H-pyrazole-4,5-diamine (530 mg) was added to the above mixture, and the whole mixture was stirred at room temperature for 1 hour. Water was added to the mixture and the whole mixture was extracted with ethyl acetate. The extract was washed with water and brine and dried over anhydrous magnesium sulfate. The solvent was removed under reduced pressure to give tert-butyl (2-{[(tert-butoxycarbonyl)amino]methyl}-3-{[1-methyl-5-(tritylamino)-1H-pyrazol-4-yl]amino}-3-oxopropyl)carbamate (270 mg).

ESI Mass: 677.3 [M+Na]$^+$ (positive)

EXAMPLE 13

7β-[(Z)-2-(5-Amino-1,2,4-thiadiazol-3-yl)-2-(1-carboxy-1-methylethoxyimino)acetamido]-3-[3-amino-4-{[3-amino-2-(aminomethyl)propanoyl]amino}-2-methyl-1-pyrazolio]methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and tert-butyl (2-{[(tert-butoxycarbonyl)amino]methyl}-3-{[1-methyl-5-(tritylamino)-1H-pyrazol-4-yl]amino}-3-oxopropyl)carbamate.

$^1$H-NMR(D$_2$O) δ 1.56 (6H, s), 3.0–3.1 (2H, m), 3.20 and 3.48 (2H, ABq, J=17.8 Hz), 3.4–3.5 (2H, m), 4.0–4.2 (1H, m), 4.8–5.3 (2H, m), 5.25 (1H, d, J=4.8 Hz), 5.84 (1H, d, J=4.7 Hz), 8.0–8.1 (1H, m)

PREPARATION 37

To a solution of 2-(4,5-diamino-1H-pyrazol-1-yl)ethanol sulfate (2 g) and (2S)-4-[(tert-butoxycarbonyl)amino]-2-hydroxybutanoic acid (1.92 g) in water (8 ml) were added triethylamine (2.32 ml) and N-(3-dimethylaminopropyl)-N'-ethylcarbodiimide hydrochloride (1.76 g), and the mixture was stirred at room temperature for 3 hours. The whole mixture was extracted with ethyl acetate-tetrahydrofuran (1:1) and the solvent was evaporated under reduced pressure to give a crude product of tert-butyl ((3S)-4-{[5-amino-1-(2-hydroxyethyl)-1H-pyrazol-4-yl]amino}-3-hydroxy-4-oxobutyl)carbamate. The obtained crude product was used for Preparation 38 without further purification.

PREPARATION 38

To a solution of tert-butyl ((3S)-4-{[5-amino-1-(2-hydroxyethyl)-1H-pyrazol-4-yl]amino}-3-hydroxy-4-oxobutyl)carbamate (2.86 g) in N,N-dimethylformamide (30 ml) were added trityl chloride (3.48 g) and triethylamine (3.48 ml), and the mixture was stirred overnight at room temperature. Water was added to the reaction mixture, and the whole mixture was extracted with ethyl acetate. The extract was washed with water and brine and dried over anhydrous magnesium sulfate. Evaporation of the solvent under reduced pressure gave crude crystals, which were washed with ethyl acetate-diisopropyl ether (2:1) and collected by filtration to give tert-butyl ((3S)-3-hydroxy-4-{[1-(2-hydroxyethyl)-5-(tritylamino)-1H-pyrazol-4-yl]amino}-4-oxobutyl)carbamate (3.5 g).

ESI Mass: 608.3 [M+Na]$^+$ (positive) $^1$H-NMR(CDCl$_3$) δ 1.2–1.5 (1H, m), 1.39 (9H, s), 1.5–1.8 (1H, m), 2.8–3.1 (2H, m), 3.2–3.4 (2H, m), 3.4–3.6 (2H, m), 3.6–3.8 (1H, m), 4.92

(1H, t, J=5.0 Hz), 5.51 (1H, d, J=5.4 Hz), 6.07 (1H, s), 6.6–6.8 (1H, m), 7.0–7.4 (15H, m), 7.43 (1H, s), 8.02 (1H, s)

PREPARATION 39

To a stirred solution of tert-butyl ((3S)-3-hydroxy-4-{[1-(2-hydroxyethyl)-5-(tritylamino)-1H-pyrazol-4-yl]amino}-4-oxobutyl)carbamate (2.5 g) in N,N-dimethylformamide (25 ml) were added trityl chloride (1.25 g), triethylamine (1.78 ml) and 4-dimethylaminopyridine (52.1 mg), and the mixture was stirred for 1 hour. The reaction mixture was warmed up to 60° C. and stirred at the same temperature for 2 days. Water was added to the mixture, and the whole mixture was extracted with ethyl acetate. The extract was washed with water and brine and dried over anhydrous magnesium sulfate. Concentration under reduced pressure gave an oil, which was purified by column chromatography on silica gel (methylene chloride:ethyl acetate=5:1) to give tert-butyl [(3S)-3-hydroxy-4-oxo-4-({5-(tritylamino)-1-[2-(trityloxy)ethyl]-1H-pyrazol-4-yl}amino)butyl]carbamate (1.5 g).

ESI Mass: 851.3 [M+Na]$^+$ (positive) $^1$H-NMR(CDCl$_3$) δ 1.2–1.5 (1H, m), 1.39 (9H, s), 1.5–1.8 (1H, m), 2.8–3.1 (4H, m), 3.3–3.5 (2H, m), 3.6–3.8 (1H, m), 5.59 (1H, d, J=5.2 Hz), 5.95 (1H, s), 6.6–6.8 (1H, m), 7.1–7.4 (30H, m), 7.43 (1H, s), 8.32 (1H, s)

PREPARATION 40

To a stirred suspension of Dess-Martin reagent (845 mg) in methylene chloride (15 ml) was added tert-butyl [(3S)-3-hydroxy-4-oxo-4-({5-(tritylamino)-1-[2-(trityloxy)ethyl]-1H-pyrazol-4-yl}amino)butyl]carbamate (1.5 g) and the mixture was stirred at room temperature for 30 minutes. 1N aqueous sodium hydroxide solution (8 ml) was added to the mixture with stirring for 30 minutes and the whole mixture was extracted with ethyl acetate. The extract was washed with water and brine and dried over anhydrous magnesium sulfate. Concentration under reduced pressure gave an oil, which was purified by column chromatography on silica gel (ethyl acetate:methylene chloride=1:4) to give tert-butyl [3,4-dioxo-4-({5-(tritylamino)-1-[2-(trityloxy)ethyl]-1H-pyrazol-4-yl}amino)butyl]carbamate (1.33 g).

ESI Mass: 848.3 [M+Na]$^+$ (positive) $^1$H-NMR(CDCl$_3$) δ 1.38 (9H, s), 2.7–2.9 (2H, m), 2.9–3.0 (2H, m), 3.1–3.4 (4H, m), 5.90 (1H, s), 6.8–6.9 (1H, m), 7.1–7.4 (30H, m), 7.45 (1H, s), 8.99 (1H, s)

PREPARATION 41

To a stirred solution of diethyl (cyanomethyl)phosphonate (311 mg) in tetrahydrofuran (13 ml) was added sodium hydride (70.3 mg, 60% oil suspension) under nitrogen atmosphere at 0° C., and the mixture was stirred for 45 minutes with warming to room temperature. tert-Butyl [3,4-dioxo-4-({5-(tritylamino)-1-[2-(trityloxy)ethyl]-1H-pyrazol-4-yl}amino)butyl]carbamate (1.32 g) was added to the mixture and the stirring was continued for 30 minutes. Water was added to the reaction mixture and the whole mixture was extracted with ethyl acetate. The extract was washed with water and brine and dried over anhydrous magnesium sulfate. Concentration under reduced pressure gave tert-butyl {(3E)-4-cyano-3-[({5-(tritylamino)-1-[2-(trityloxy)ethyl]-1H-pyrazol-4-yl}amino)carbonyl]-3-buten-1-yl}carbamate (1.13 g).

ESI Mass: 872.3 [M+Na]$^+$ (positive) $^1$H-NMR(CDCl$_3$) δ 1.36 (9H, s), 2.4–2.6 (2H, m), 2.8–3.1 (4H, m), 3.2–3.4 (2H, m), 5.54 (1H, s), 5.80 (1H, s), 6.8–7.0 (1H, m), 7.0–7.5 (31H, m), 8.87 (1H, s)

PREPARATION 42

To a solution of tert-butyl ({3E)-4-cyano-3-[({5-(tritylamino)-1-[2-(trityloxy)ethyl]-1H-pyrazol-4-yl}amino)carbonyl]-3-buten-1-yl}carbamate (1.1 g) in ethanol (10 ml) was added di-tert-butyl dicarbonate (297 mg) and PtO$_2$ (59 mg), and the mixture was stirred for 5 days under hydrogen atmosphere. The catalyst was filtered off, and the filtrate was concentrated under reduced pressure to give an oil, which was purified by column chromatography on silica gel (methylene chloride:ethyl acetate=5:1→1:1) to give di-tert-butyl {3-[({5-(tritylamino)-1-[2-(trityloxy)ethyl]-1H-pyrazol-4-yl}amino)carbonyl]-1,5-pentanediyl}biscarbamate (570 mg).

ESI Mass: 978.4 [M+Na]$^+$ (positive) $^1$H-NMR(CDCl$_3$) δ 1.37 (18H, s), 1.7–2.0 (1H, m), 2.6–2.8 (4H, m), 2.8–3.0 (2H, m), 3.3–3.5 (2H, m), 5.87 (1H, s), 6.6–6.8 (2H, m), 7.1–7.4 (31H, m), 7.92 (1H, s)

EXAMPLE 14

7β-[(Z)-2-(5-Amino-1,2,4-thiadiazol-3-yl)-2-(1-carboxy-1-methylethoxyimino)acetamido]-3-[3-amino-4-{[4-amino-2-(2-aminoethyl)butanoyl]amino}-2-(2-hydroxyethyl)-1-pyrazolio]methyl-3-cephem-4-carboxylic acid hydrogensulfate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl {3-[({5-(tritylamino)-1-[2-(trityloxy)ethyl]-1H-pyrazol-4-yl}amino)carbonyl]-1,5-pentanediyl}biscarbamate.

$^1$H-NMR(D$_2$O) δ 1.54 (6H, s), 1.8–2.2 (4H, m), 2.6–2.9 (1H, m), 2.9–3.2 (4H, m), 3.18 and 3.57 (2H, ABq, J=17.7 Hz), 3.8–4.0 (2H, m), 4.3–4.5 (2H, m), 4.8–5.2 (2H, m), 5.30 (1H, d, J=4.8 Hz), 5.85 (1H, d, J=4.8 Hz), 8.14 (1H, s)

PREPARATION 43

To a solution of 2-(4,5-diamino-1H-pyrazol-1-yl)ethanol sulfate (5 g) in water (30 ml) and dioxane (15 ml) was added aqueous sodium hydroxide solution under ice-cooling to adjust the mixture to pH 7. Phenyl chloroformate (3.42 g) was added to the mixture with controlling pH at 7, and the whole mixture was stirred at room temperature for 2 hours. The reaction mixture was extracted with ethyl acetate-tetrahydrofuran (1:1) and the extract was dried over anhydrous magnesium sulfate. Evaporation of the solvent gave a crude product of phenyl [5-amino-1-(2-hydroxyethyl)-1H-pyrazol-4-yl]carbamate as an oil, which was used for Preparation 44 without further purification.

PREPARATION 44

To a stirred solution of phenyl [5-amino-1-(2-hydroxyethyl)-1H-pyrazol-4-yl]carbamate (5.45 g) in N,N-dimethylformamide (55 ml) were added triethylamine (8.69 ml) and trityl chloride (6.37 g), and the mixture was stirred at room temperature for 1 hour. Water was added to the reaction mixture and the whole mixture was extracted with ethyl acetate. The extract was washed with water and brine and dried over anhydrous magnesium sulfate. Concentration under reduced pressure gave a crude product, which was triturated with ethyl acetate-diisopropyl ether (1:2). The resulting solid was collected by filtration to give phenyl [1-(2-hydroxyethyl)-5-(tritylamino)-1H-pyrazol-4-yl]carbamate (3.5 g).

ESI Mass: 527.2 [M+Na]$^+$ (positive) $^1$H-NMR(CDCl$_3$) δ 3.12 (2H, t, J=5.9 Hz), 3.3–3.5 (2H, m), 4.92 (1H, t, J=5.1 Hz), 5.79 (1H, s), 6.9–7.5 (21H, m), 7.77 (1H, s)

PREPARATION 45

To a stirred solution of phenyl [1-(2-hydroxyethyl)-5-(tritylamino)-1H-pyrazol-4-yl]carbamate (1 g) in N,N-dimethylformamide (10 ml) were added di-tert-butyl (2-amino-1,3-propanediyl)biscarbamate (631 mg) and triethylamine (0.83 ml), and the mixture was stirred at room temperature for 3 hours. Water was added to the reaction mixture and the whole mixture was extracted with ethyl acetate. The extract was washed with water and brine and dried over anhydrous magnesium sulfate. Concentration under reduced pressure gave a crude product, which was triturated with ethyl acetate-diisopropyl ether (1:3). The resulting solid was collected by filtration to give di-tert-butyl {2-[({[1-(2-hydroxyethyl)-5-(tritylamino)-1H-pyrazol-4-yl]amino}carbonyl)amino]-1,3-propanediyl}biscarbamate (435 mg).

$^1$H-NMR(CDCl$_3$) δ 1.38 (18H, s), 2.8–3.0 (4H, m), 3.0–3.1 (2H, m), 3.3–3.5 (2H, m), 3.4–3.6 (1H, m), 4.78 (1H, t, J=5.1 Hz), 5.73 (1H, d, J=7.3 Hz), 5.80 (1H, s), 6.50 (1H, s), 6.5–6.8 (2H, m), 7.0–7.4 (16H, m)

EXAMPLE 15

7β-[(Z)-2-(5-Amino-1,2,4-thiadiazol-3-yl)-2-(1-carboxy-1-methylethoxyimino)acetamido]-3-[3-amino-4-[({[2-amino-1-(aminomethyl)ethyl]amino}carbonyl)amino]-2-(2-hydroxyethyl)-1-pyrazolio]methyl-3-cephem-4-carboxylate The title compound was obtained in the same manner as in Example 6 from 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate and di-tert-butyl {2-[({[1-(2-hydroxyethyl)-5-(tritylamino)-1H-pyrazol-4-yl]amino}carbonyl)amino]-1,3-propanediyl}biscarbamate.

$^1$H-NMR(D$_2$O) δ 1.54 (6H, s), 3.0–3.3 (5H, m), 3.4–3.7 (2H, m), 3.8–4.0 (2H, m), 4.2–4.5 (2H, m), 4.8–5.2 (2H, m), 5.28 (1H, d, J=4.8 Hz), 5.86 (1H, d, J=4.6 Hz), 8.00 (1H, s)

PREPARATION 46

To a suspension of 1-methyl-1H-pyrazole-4,5-diamine sulfate (2.10 g), (2S)-2-[(benzyloxycarbonyl)amino]-5-[(tert-butoxycarbonyl)amino]pentanoic acid (3.66 g) and triethylamine (3.04 g) in chloroform (50 ml) was added N-(3-dimethylaminopropyl)-N'-ethylcarbodiimide hydrochloride (1.91 g), and the mixture was stirred at room temperature for 15 hours. The reaction mixture was washed successively with 10% aqueous citric acid solution, brine and saturated aqueous sodium hydrogencarbonate solution. The organic layer was dried over anhydrous sodium sulfate, filtered and concentrated in vacuo to give a crude product of 1-benzyl 4-tert-butyl {(1S)-1-[(5-amino-1-methyl-1H-pyrazol-4-yl)carbamoyl]tetramethylene}biscarbamate as an oil. The crude product was used directly in the next step without further purification.

To a solution of the crude product of 1-benzyl 4-tert-butyl {(1S)-1-[(5-amino-1-methyl-1H-pyrazol-4-yl)carbamoyl]tetramethylene}biscarbamate and triethylamine (1.01 g) in chloroform (50 ml) was added triphenylmethyl chloride (2.78 g), and the mixture was stirred at room temperature for 2 hours. The reaction mixture was washed successively with 10% aqueous citric acid solution, brine and saturated aqueous sodium hydrogencarbonate solution. The organic layer was dried over anhydrous magnesium sulfate, filtered and concentrated in vacuo. The residue was purified by column chromatography on silica gel eluting with 2% methanol/chloroform to give 1-benzyl 4-tert-butyl ((1S)-1-{[1-methyl-5-(tritylamino)-1H-pyrazol-4-yl]carbamoyl}tetramethylene)biscarbamate (720 mg) as an oil.

$^1$H-NMR(CDCl$_3$) δ 1.41 (9H, s), 1.42–1.60 (4H, m), 2.90 (3H, s), 3.02–3.04 (1H, m), 3.23–3.25 (1H, m), 3.93–3.95 (1H, m), 4.62 (1H, br), 4.66 (1H, s), 5.10 (2H, s), 5.36 (1H, br), 6.98 (1H, br), 7.20–7.36 (20H, m), 7.52 (1H, s)

PREPARATION 47

A solution of 1-benzyl 4-tert-butyl ((1S)-1-{[1-methyl-5-(tritylamino)-1H-pyrazol-4-yl]carbamoyl}tetramethylene)biscarbamate (6.4 g) in methanol (100 ml) was treated with 10% palladium on carbon (1.0 g) under a hydrogen atmosphere at room temperature for 6 days. After the catalyst was filtered off, the filtrate was concentrated in vacuo. The residue was triturated with ether and dried in vacuo to give tert-butyl (4S)-4-amino-5-{[1-methyl-5-(tritylamino)-1H-pyrazol-4-yl]amino}-5-oxopentylcarbamate (2.2 g) as a solid.

$^1$H-NMR(CDCl$_3$) δ 1.42 (9H, s), 1.50–1.74 (4H, m), 2.94 (3H, s), 3.08–3.12 (2H, m), 3.17–3.19 (1H, m), 4.67 (1H, br), 4.83 (1H, s), 7.20–7.26 (15H, m), 7.37 (1H, s), 8.03 (1H, s)

PREPARATION 48

To a solution of tert-butyl (4S)-4-amino-5-{[1-methyl-5-(tritylamino)-1H-pyrazol-4-yl]amino}-5-oxopentylcarbamate (1.71 g) in tetrahydrofuran (30 ml) was added N-[2-(tert-butoxycarbonylamino)acetoxy]-succinimide (820 mg). The mixture was stirred at room temperature for 6 hours. To the reaction mixture was added chloroform (50 ml). The mixture was washed successively with 10% aqueous citric acid solution, brine and saturated aqueous sodium hydrogencarbonate solution. The organic layer was dried over anhydrous magnesium sulfate, filtered and concentrated in vacuo to give tert-butyl (4S)-4-{[2-(tert-butoxycarbonylamino)acetyl]amino}-5-{[1-methyl-5-(tritylamino)-1H-pyrazol-4-yl]amino}-5-oxopentylcarbamate (2.1 g) as an oil.

$^1$H-NMR(CDCl$_3$) δ 1.41 (9H, s), 1.43 (9H, s), 1.42–1.64 (4H, m), 2.87 (3H, s), 3.01–3.19 (2H, m), 3.71–3.80 (2H, m), 4.18–4.20 (1H, m), 4.75 (1H, br), 4.78 (1H, br), 5.27 (1H, br), 6.76 (1H, d, J=7 Hz), 7.18 (1H, br), 7.19–7.32 (15H, m), 7.52 (1H, s)

EXAMPLE 16

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.0 g) in N,N-dimethylformamide (3 ml) was added N-(trimethylsilyl)acetamide (965 mg) and the mixture was stirred at room temperature for 30 minutes. To the solution was added potassium iodide (341 mg) and the mixture was stirred at room temperature for 30 minutes. To the reaction mixture was added tert-butyl (4S)-4-{[2-(tert-butoxycarbonylamino)acetyl]amino}-5-{[1-methyl-5-(tritylamino)-1H-pyrazol-4-yl]amino}-5-oxopentylcarbamate (1.27 g), and the whole mixture was stirred at 40° C. for 4 hours. To the reaction mixture was added ethyl acetate (100 ml) and the mixture was washed successively with brine (50 ml), 10% aqueous sodium trifluoroacetate solution (50 ml) and brine (50 ml), dried over anhydrous magnesium sulfate and filtered. The filtrate was concentrated to about 5 ml in vacuo. The concentrate was poured into diisopropyl ether (120 ml) and the resulting precipitate was collected by filtration and dried in vacuo. To a solution of the solid in methylene chloride (4.5 ml) were added anisole (1.5 ml) and trifluoroacetic acid (3.0 ml). The resulting solution was stirred at room temperature for 16 hours and poured into diisopropyl ether (120 ml). The resulting precipitate was collected by filtration and dried in vacuo to give a crude product (1.42 g), which was purified by preparative HPLC utilizing ODS column. The eluate containing a desired product was concentrated to about 20 ml in vacuo. The concentrate was further purified by preparative HPLC utilizing ODS column eluting with 8% acetonitrile/water. The eluate was concentrated to about 10 ml in vacuo. The resulting solution was lyophilized to give 7β-[(Z)-2-(5-amino-1,2,4-thiadiazol-3-yl)-2-(1-carboxy-1-methylethoxyimino)acetamido]-3-[3-amino-4-({(2S)-5-amino-2-[(aminoacetyl)amino]pentanoyl}amino)-2-methyl-1-pyrazolio]methyl-3-cephem-4-carboxylate (46.3 mg) as an amorphous solid.

$^1$H-NMR(D$_2$O) δ 1.52 (6H, s), 1.69–2.02 (4H, m), 3.03 (2H, t, J=7.3 Hz), 3.19 (1H, d, J=17.9 Hz), 3.49 (1H, d, J=17.9 Hz), 3.74 (3H, s), 3.90 (2H, s), 4.49 (1H, m), 4.97 (1H, d, J=14.7 Hz), 5.12 (1H, d, J=14.7 Hz), 5.25 (1H, d, J=4.6 Hz), 5.83 (1H, d, J=4.6 Hz), 8.00 (1H, s)

PREPARATION 49

To a solution of (2S)-2-[(benzyloxycarbonyl)amino]-5-[(tert-butoxycarbonyl)amino]pentanoic acid (22.0 g) and triethylamine (6.7 g) in tetrahydrofuran (240 ml) was added methyl chloroformate (6.2 g) followed by stirring under ice-cooling for 30 minutes. To the reaction mixture was added a solution of 1-methyl-1H-pyrazole-4,5-diamine sulfate (12.6 g) and triethylamine (13.4 g) in water (50 ml) at the same temperature. The mixture was stirred at the room temperature for 1 hour. To the reaction mixture was added chloroform (240 ml), and the layers were separated. The organic layer was washed successively with 10% aqueous citric acid solution, brine and saturated aqueous sodium hydrogencarbonate solution. The organic layer was dried over anhydrous magnesium sulfate, filtered and concentrated in vacuo to give a crude product of 1-benzyl 4-tert-butyl {(1S)-1-[(5-amino-1-methyl-1H-pyrazol-4-yl)carbamoyl]tetramethylene}biscarbamate as an oil. The crude product was used directly in the next step without further purification.

A solution of the crude product of 1-benzyl 4-tert-butyl {(1S)-1-[(5-amino-1-methyl-1H-pyrazol-4-yl)carbamoyl]tetramethylene}biscarbamate in methanol (200 ml) was treated with 10% palladium on carbon (1.0 g) under a hydrogen atmosphere at room temperature for 6 days. After the catalyst was filtered off, the filtrate was concentrated in vacuo. The residue was triturated with ether and dried in vacuo to give tert-butyl (4S)-4-amino-5-[(5-amino-1-methyl-1H-pyrazol-4-yl)amino]-5-oxopentylcarbamate (5.5 g) as a solid.

$^1$H-NMR(CDCl$_3$) δ 1.40 (9H, s), 1.41 (9H, s), 1.42–1.44 (4H, m), 2.33–2.44 (2H, m), 2.85 (3H, s), 3.02–3.40 (2H, m), 3.38–3.39 (2H, m), 4.18–4.20 (1H, m), 4.74 (1H, br), 4.76 (1H, s), 5.24 (1H, br), 6.39 (1H, d, J=7 Hz), 7.17 (1H, br), 7.18–7.30 (15H, m), 7.52 (1H, s)

PREPARATION 50

To a solution of tert-butyl (4S)-4-amino-5-[(5-amino-1-methyl-1H-pyrazol-4-yl)amino]-5-oxopentylcarbamate (4.90 g) and triethylamine (1.52 g) in chloroform (100 ml) was added N-[3-(tert-butoxycarbonylamino)propionyloxy]succinimide (4.26 g). The mixture was stirred at room temperature for 17 hours. The mixture was washed with saturated aqueous sodium hydrogencarbonate solution. The organic layer was dried over anhydrous magnesium sulfate, filtered and concentrated in vacuo to give a crude product of tert-butyl (4S)-5-[(5-amino-1-methyl-1H-pyrazol-4-yl)amino]-4-{[3-(tert-butoxycarbonylamino)propionyl]amino}-5-oxopentylcarbamate as an oil. The crude product was used directly in the next step without further purification.

To a solution of the crude product of tert-butyl (4S)-5-[(5-amino-1-methyl-1H-pyrazol-4-yl)amino]-4-{[3-(tert-butoxycarbonylamino)propionyl]amino}-5-oxopentylcarbamate and triethylamine (1.52 g) in chloroform (100 ml) was added triphenylmethyl chloride (4.20 g), and the mixture was stirred at room temperature for 1 hour. The reaction mixture was washed successively with 10% aqueous citric acid solution, brine and saturated aqueous sodium hydrogencarbonate solution. The organic layer was dried over anhydrous magnesium sulfate, filtered and concentrated in vacuo to give tert-butyl (4S)-4-{[3-(tert-butoxycarbonylamino)propionyl]amino}-5-{[1-methyl-5-(tritylamino)-1H-pyrazol-4-yl]amino}-5-oxopentylcarbamate (7.20 g) as an oil.

$^1$H-NMR(CDCl$_3$) δ 1.40 (9H, s), 1.41 (9H, s), 1.42–1.44 (4H, m), 2.33–2.44 (2H, m), 2.85 (3H, s), 3.02–3.40 (2H, m), 3.38–3.39 (2H, m), 4.18–4.20 (1H, m), 4.74 (1H, br), 4.76 (1H, s), 5.24 (1H, br), 6.39 (1H, d, J=7 Hz), 7.17 (1H, br), 7.18–7.30 (15H, m), 7.52 (1H, s)

EXAMPLE 17

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (6.63 g) in N,N-dimethylformamide (20 ml) was added N-(trimethylsilyl)acetamide (6.39 g) and the mixture was stirred at room temperature for 30 minutes. To the solution was added potassium iodide (2.26 g) and the mixture was stirred at room temperature for 30 minutes. To the reaction mixture was added tert-butyl (4S)-4-{[3-(tert-butoxycarbonylamino)propionyl]amino}-5-{[1-methyl-5-(tritylamino)-1H-pyrazol-4-yl]amino}-5-oxopentylcarbamate (7.20 g), and the whole mixture was stirred at 40° C. for 3 hours. To the resulting reaction mixture was added ethyl acetate (600 ml) and the solution was washed successively with brine (300 ml), 10% aqueous sodium trifluoroacetate solution (300 ml) and brine (300 ml), dried over anhydrous magnesium sulfate and filtered. The filtrate was concentrated to about 30 ml in vacuo. The concentrate was poured into diisopropyl ether (700 ml) and the resulting precipitate was collected by filtration and dried in vacuo. To a solution of the solid in methylene chloride (30 ml) were added anisole (10 ml) and trifluoroacetic acid (30 ml). The resulting solution was stirred at room temperature for 5 hours and poured into diisopropyl ether (850 ml). The resulting precipitate was collected by filtration and dried in vacuo to give a crude product (9.50 g), which was purified by preparative HPLC utilizing ODS column. The eluate containing a desired product was concentrated to about 20 ml in vacuo. The concentrate was further purified by preparative HPLC utilizing ODS column eluting with 20% acetonitrile/water. The eluate was concentrated to about 10 ml in vacuo and 1.0 mol/l sulfuric acid (1.42 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-({(2S)-5-amino-2-[(3-aminopropionyl)amino]pentanoyl}amino)-2-methyl-1-pyrazolio]methyl-3-cephem-4-carboxylic acid hydrogensulfate (1.29 g) as an amorphous solid.

$^1$H-NMR(D$_2$O) δ 1.62 (6H, s), 1.73–2.03 (4H, m), 2.80 (2H, t, J=6.9 Hz), 3.05 (1H, t, J=7.3 Hz), 3.24 (1H, d, J=17.9 Hz), 3.28 (2H, t, J=6.9 Hz), 3.47 (1H, d, J=17.9 Hz), 3.74 (3H, s), 4.45 (1H, m), 5.07 (1H, d, J=16.5 Hz), 5.26 (1H, d, J=16.5 Hz), 5.26 (1H, d, J=5.0 Hz), 5.88 (1H, d, J=5.0 Hz), 8.07 (1H, s)

PREPARATION 51

To a solution of tert-butyl (4S)-4-amino-5-[(5-amino-1-methyl-1H-pyrazol-4-yl)amino]-5-oxopentylcarbamate (560 mg) and triethylamine (170 mg) in chloroform (30 ml) was added di-tert-butyl ({[(trifluoromethyl)sulfonyl]imino}methylene-biscarbamate (660 mg). The mixture was stirred at room temperature for 18 hours. The reaction mixture was washed with brine, and the organic layer was dried over anhydrous magnesium sulfate, filtered and concentrated in vacuo to give a crude product of tert-butyl (4S)-5-[(5-amino-1-methyl-1H-pyrazol-4-yl)amino]-4-[2,3-bis(tert-butoxycarbonyl)guanidino]-5-oxopentylcarbamate as an oil. The crude product was used directly in the next step without further purification.

To a solution of the crude product of tert-butyl (4S)-5-[(5-amino-1-methyl-1H-pyrazol-4-yl)amino]-4-[2,3-bis(tert-butoxycarbonyl)guanidino]-5-oxopentylcarbamate and triethylamine (170 mg) in chloroform (30 ml) was added triphenylmethyl chloride (470 mg), and the mixture was stirred at room temperature for 6 hours. The reaction mixture was washed successively with 10% aqueous citric acid solution, brine and saturated aqueous sodium hydrogencarbonate solution. The organic layer was dried over anhydrous magnesium sulfate, filtered and concentrated in vacuo. The residue was purified by column chromatography on silica gel eluting with 3% methanol/chloroform to give tert-butyl (4S)-4-[2,3-bis(tert-butoxycarbonyl)guanidino]-5-{[1-methyl-5-(tritylamino)-1H-pyrazol-4-yl]amino}-5-oxopentylcarbamate (850 mg) as an oil.

$^1$H-NMR(CDCl$_3$) δ 1.39 (9H, s), 1.44 (9H, s), 1.49 (9H, s), 1.57–1.79 (4H, m), 2.88 (3H, s), 3.05–3.16 (2H, m), 4.23–4.24 (1H, m), 4.63 (1H, s), 4.65 (1H, br), 7.22–7.33 (15H, m), 7.54 (1H, brs), 7.60 (1H, s), 8.57 (1H, d, J=7 Hz), 11.28 (1H, s)

EXAMPLE 18

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (680 mg) in N,N-dimethylformamide (2 ml) was added N-(trimethylsilyl)acetamide (660 mg) and the mixture was stirred at room temperature for 30 minutes. To the solution was added potassium iodide (232 mg) and the mixture was stirred at room temperature for 30 minutes. To the reaction mixture was added tert-butyl (4S)-4-[2,3-bis(tert-butoxycarbonyl)guanidino]-5-{[1-methyl-5-(tritylamino)-1H-pyrazol-4-yl]amino}-5-oxopentylcarbamate (810 mg), and the whole mixture was stirred at 40° C. for 4 hours. To the resulting reaction mixture was added ethyl acetate (100 ml) and the solution was washed successively with brine (50 ml), 10% aqueous sodium trifluoroacetate solution (50 ml) and brine (50 ml), dried over anhydrous magnesium sulfate and filtered. The filtrate was concentrated to about 5 ml in vacuo. The concentrate was poured into diisopropyl ether (120 ml) and the resulting precipitate was collected by filtration and dried in vacuo. To a solution of the solid in methylene chloride (3.0 ml) were added anisole (1.0 ml) and trifluoroacetic acid (3.0 ml). The resulting solution was stirred at room temperature for 4 hours and poured into diisopropyl ether (120 ml). The resulting precipitate was collected by filtration and dried in vacuo to give a crude product (0.54 g), which was purified by preparative HPLC utilizing ODS column. The eluate containing a desired product was concentrated to about 20 ml in vacuo. The concentrate was further purified by preparative HPLC utilizing ODS column eluting with 15% acetonitrile/water. The eluate was concentrated to about 10 ml in vacuo and 0.05 mol/l sulfuric acid (0.924 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-{[(2S)-5-amino-2-(guanidino)pentanoyl]amino}-2-methyl-1-pyrazolio]methyl-3-cephem-4-carboxylic acid hydrogensulfate (61.0 mg) as an amorphous solid.

$^1$H-NMR(D$_2$O) δ 1.58 (6H, s), 1.76–1.84 (2H, m), 1.86–1.96 (1H, m), 2.04–2.13 (1H, m), 3.04 (2H, t, J=7.3 Hz), 3.21 (1H, d, J=17.9 Hz), 3.46 (1H, d, J=17.9 Hz), 3.73 (3H, s), 4.36–4.42 (1H, m), 4.98 (1H, d, J=15.6 Hz), 5.20 (1H, d, J=15.6 Hz), 5.24 (1H, d, J=4.6 Hz), 5.84 (1H, d, J=4.6 Hz), 8.06 (1H, s)

PREPARATION 52

To a solution of (2S)-2-[(benzyloxycarbonyl)amino]-6-[(tert-butoxycarbonyl)amino]hexanoic acid (19.02 g) and triethylamine (5.56 g) in tetrahydrofuran (200 ml) was added methyl chloroformate (4.21 ml), followed by stirring under ice-cooling for 30 minutes. To the reaction mixture was added a solution of 1-methyl-1H-pyrazole-4,5-diamine sulfate (15.75 g) and triethylamine (15.2 g) in water (50 ml) at the same temperature. The mixture was stirred at room temperature for 30 minutes. To the reaction mixture was added chloroform (300 ml), and the layers were separated. The organic layer was washed successively with 10% aqueous citric acid solution, brine and saturated aqueous sodium hydrogencarbonate solution. The organic layer was dried over anhydrous magnesium sulfate, filtered and concentrated in vacuo to give a crude product of 1-benzyl 5-tert-butyl (1S)-{1-[(5-amino-1-methyl-1H-pyrazol-4-yl)carbamoyl]pentamethylene}biscarbamate as an oil. The crude product was used directly in the next step without further purification.

To a solution of the crude product of 1-benzyl 5-tert-butyl (1S)-{1-[(5-amino-1-methyl-1H-pyrazol-4-yl)carbamoyl]pentamethylene}biscarbamate in methanol (350 ml) was treated with 10% palladium on carbon (2.0 g) under a hydrogen atmosphere at room temperature for 6 days. After the catalyst was filtered off, the filtrate was concentrated in vacuo. The residue was triturated with ethyl acetate and dried in vacuo to give tert-butyl (5S)-5-amino-6-[(5-amino-1-methyl-1H-pyrazol-4-yl)amino]-6-oxohexylcarbamate (12.1 g) as a solid.

$^1$H-NMR(DMSO-d$_6$) δ 1.24–1.40 (4H, m), 1.36 (9H, s), 1.70–1.77 (2H, m), 2.88–2.91 (2H, m), 3.51 (3H, s), 3.80–3.82 (1H, m), 5.15 (2H, s), 6.77 (1H, br), 7.27 (1H, s), 10.05 (1H, br)

PREPARATION 53

To a solution of tert-butyl (5S)-5-amino-6-[(5-amino-1-methyl-1H-pyrazol-4-yl)amino]-6-oxohexylcarbamate (1.60 g) and triethylamine (0.47 g) in chloroform (100 ml) was added N-[3-(tert-butoxycarbonylamino)propionyloxy] succinimide (1.34 g). The mixture was stirred at room temperature for 15 hours. The mixture was washed with saturated aqueous sodium hydrogencarbonate solution. The organic layer was dried over anhydrous magnesium sulfate, filtered and concentrated in vacuo to give a crude product of tert-butyl (5S)-6-[(5-amino-1-methyl-1H-pyrazol-4-yl)amino]-5-{[3-(tert-butoxycarbonylamino)propionyl]amino}-6-oxohexylcarbamate (2.09 g) as an oil. The crude product was used directly in the next step without further purification.

To a solution of the crude product of tert-butyl (5S)-6-[(5-amino-1-methyl-1H-pyrazol-4-yl)amino]-5-{[3-(tert-butoxycarbonylamino)propionyl]amino}-6-oxohexylcarbamate and triethylamine (0.50 g) in chloroform (30 ml) was added triphenylmethyl chloride (1.37 g), and the mixture was stirred at room temperature for 16 hours. The reaction mixture was washed successively with 10% aqueous citric acid solution, brine and saturated aqueous sodium hydrogencarbonate solution. The organic layer was dried over anhydrous magnesium sulfate, filtered and concentrated in vacuo. The residue was purified by column chromatography on silica gel eluting with 3% methanol/chloroform to give tert-butyl (5S)-5-{[3-(tert-butoxycarbonylamino)propionyl]amino}-6-{[1-methyl-5-(tritylamino)-1H-pyrazol-4-yl]amino}-6-oxohexylcarbamate (1.62 g) as an oil.

$^1$H-NMR(CDCl$_3$) δ 1.24–1.70 (6H, m), 1.42 (18H, s), 2.30–2.44 (2H, m), 2.91 (3H, s), 3.06–3.10 (2H, m), 3.35–3.39 (2H, m), 4.01–4.05 (1H, m), 4.58 (1H, s), 4.66 (1H, br), 5.23 (1H, br), 6.21 (1H, br), 6.78 (1H, br), 7.12–7.32 (15H, m), 7.58 (1H, s)

EXAMPLE 19

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.36 g) in N,N-dimethylformamide (4 ml) was added N-(trimethylsilyl)acetamide (1.31 g) and the mixture was stirred at room temperature for 30 minutes. To the solution was added potassium iodide (465 mg) and the mixture was stirred at room temperature for 30 minutes. To the reaction mixture was added tert-butyl (5S)-5-{[3-(tert-butoxycarbonylamino)propionyl]amino}-6-{[1-methyl-5-(tritylamino)-1H-pyrazol-4-yl]amino}-6-oxohexylcarbamate (1.87 g), and the whole mixture was stirred at room temperature for 22 hours. To the resulting reaction mixture was added ethyl acetate (150 ml) and the solution was washed successively with brine (80 ml), 10% aqueous sodium trifluoroacetate solution (80 ml) and brine (80 ml), dried over anhydrous magnesium sulfate and filtered. The filtrate was concentrated to about 5 ml in vacuo. The concentrate was poured into diisopropyl ether (120 ml) and the resulting precipitate was collected by filtration and dried in vacuo. To a solution of the solid in methylene chloride (6.0 ml) were added anisole (2.0 ml) and trifluoroacetic acid (6.0 ml). The resulting solution was stirred at room temperature for 6 hours and poured into diisopropyl ether (120 ml). The resulting precipitate was collected by filtration and dried in vacuo to give a crude product (1.62 g), which was purified by preparative HPLC utilizing ODS column. The eluate containing a desired product was concentrated to about 20 ml in vacuo. The concentrate was further purified by preparative HPLC utilizing ODS column eluting with 20% acetonitrile/water. The eluate was concentrated to about 10 ml in vacuo and 0.05 mol/l sulfuric acid (6.96 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-({(2S)-6-amino-2-[(3-aminopropionyl)amino]hexanoyl}amino)-2-methyl-1-pyrazolio]methyl-3-cephem-4-carboxylic acid hydrogensulfate (286.7 mg) as an amorphous solid.

$^1$H-NMR(D$_2$O) δ 1.42–1.57 (2H, m), 1.61 (6H, d, J=3.2 Hz), 1.67–1.75 (2H, m), 1.78–1.96 (2H, m), 2.78 (2H, t, J=6.9 Hz), 3.00 (2H, t, J=7.8 Hz), 3.23 (1H, d, J=17.9 Hz), 3.27 (2H, t, J=6.9 Hz), 3.46 (2H, d, J=17.9 Hz), 3.73 (3H, s), 4.37–4.42 (1H, m), 5.04 (1H, d, J=15.6 Hz), 5.25 (1H, d, J=15.6 Hz), 5.25 (1H, d, J=5.0 Hz), 5.87 (1H, d, J=5.0 Hz), 8.05 (1H, s)

PREPARATION 54

To a solution of tert-butyl (5S)-5-amino-6-[(5-amino-1-methyl-1H-pyrazol-4-yl)amino]-6-oxohexylcarbamate (3.4 g) and triethylamine (1.21 g) in chloroform (100 ml) was added di-tert-butyl ({[(trifluoromethyl)sulfonyl]imino}methylene-biscarbamate (4.70 g). The mixture was stirred at room temperature for 15 hours. The reaction mixture was washed with brine, and the organic layer was dried over anhydrous magnesium sulfate, filtered and concentrated in vacuo to give a crude product of tert-butyl (5S)-5-[2,3-bis(tert-butoxycarbonyl)guanidino]-6-[(5-amino-1-methyl-1H-pyrazol-4-yl)amino]-6-oxohexylcarbamate as an oil. The crude product was used directly in the next step without further purification.

To a solution of the crude product tert-butyl (5S)-5-[2,3-bis(tert-butoxycarbonyl)guanidino]-6-[(5-amino-1-methyl-1H-pyrazol-4-yl)amino]-6-oxohexylcarbamate and triethylamine (1.01 g) in chloroform (100 ml) was added triphenylmethyl chloride (2.78 g), and the mixture was stirred at room temperature for 2 hours. The reaction mixture was washed successively with 10% aqueous citric acid solution, brine and saturated aqueous sodium hydrogencarbonate solution. The organic layer was dried over anhydrous magnesium sulfate, filtered and concentrated in vacuo. The residue was purified by column chromatography on silica gel eluting with 3% methanol/chloroform to give tert-butyl (5S)-5-[2,3-bis(tert-butoxycarbonyl)guanidino]-6-{[1-methyl-5-(tritylamino)-1H-pyrazol-4-yl]amino}-6-oxohexylcarbamate (5.60 g) as an oil.

$^1$H-NMR(CDCl$_3$) δ 1.21–1.79 (6H, m), 1.37 (9H, s), 1.44 (9H, s), 1.49 (9H, s), 2.88 (3H, s), 3.02–3.11 (2H, m), 4.14–4.19 (1H, m), 4.55 (1H, s), 4.58 (1H, br), 7.16–7.31 (15H, m), 7.53 (1H, br), 7.62 (1H, s), 8.52 (1H, d, J=7 Hz), 11.30 (1H, s)

EXAMPLE 20

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.02 g) in N,N-dimethylformamide (3.0 ml) was added N-(trimethylsilyl)acetamide (980 mg) and the mixture was stirred at room temperature for 30 minutes. To the solution was added potassium iodide (350 mg) and the mixture was stirred at room temperature for 30 minutes. To the reaction mixture was added tert-butyl (5S)-5-[2,3-bis(tert-butoxycarbonyl)guanidino]-6-{[1-methyl-5-(tritylamino)-1H-pyrazol-4-yl]amino}-6-oxohexylcarbamate (1.48 g), and the whole mixture was stirred at 40° C. for 4 hours. To the resulting reaction mixture was added ethyl acetate (150 ml) and the solution was washed successively with brine (75 ml), 10% aqueous sodium trifluoroacetate solution (75 ml) and brine (75 ml), dried over anhydrous magnesium sulfate and filtered. The filtrate was concentrated to about 5 ml in vacuo. The concentrate was poured into diisopropyl ether (150 ml) and the resulting precipitate was collected by filtration and dried in vacuo. To a solution of the solid in methylene chloride (3.0 ml) were added anisole (1.0 ml) and trifluoroacetic acid (3.0 ml). The resulting solution was stirred at room temperature for 4 hours and poured into diisopropyl ether (150 ml). The resulting precipitate was collected by filtration and dried in vacuo to give a crude product (0.92 g), which was purified by preparative HPLC utilizing ODS column. The eluate containing a desired product was concentrated to about 20 ml in vacuo. The concentrate was further purified by preparative HPLC utilizing ODS column eluting with 15% acetonitrile/water. The eluate was concentrated to about 10 ml in vacuo and 0.05 mol/l sulfuric acid (2.07 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-{[(2S)-6-amino-2-(guanidino)hexanoyl]amino}-2-methyl-1-pyrazolio]methyl-3-cephem-4-carboxylic acid hydrogensulfate (94.6 mg) as an amorphous solid.

$^1$H-NMR(D$_2$O) δ 1.45–1.56 (2H, m), 1.60 (6H, d, J=3.2 Hz), 1.66–1.75 (2H, m), 1.83–1.93 (1H, m), 1.98–2.08 (1H, m), 3.00 (2H, t, J=7.8 Hz), 3.22 (1H, d, J=17.9 Hz), 3.45 (1H, d, J=17.9 Hz), 3.72 (3H, s), 4.32–4.38 (1H, m), 5.00 (1H, d, J=15.6 Hz), 5.23 (1H, d, J=15.6 Hz), 5.24 (1H, d, J=4.6 Hz), 5.85 (1H, d, J=4.6 Hz), 8.07 (1H, s)

PREPARATION 55

To a solution of tert-butyl (5S)-5-amino-6-[(5-amino-1-methyl-1H-pyrazol-4-yl)amino]-6-oxohexylcarbamate (3.06 g) and triethylamine (1.09 g) in chloroform (30 ml) was added di-tert-butyl dicarbonate (2.36 g). The mixture was stirred at room temperature for 14 hours. The reaction mixture was washed with brine, and the organic layer was dried over anhydrous magnesium sulfate, filtered and concentrated in vacuo to give a crude product of di-tert-butyl (1S)-{1-[(5-amino-1-methyl-1H-pyrazol-4-yl)carbamoyl]pentamethylene}-biscarbamate as an oil. The crude product was used directly in the next step without further purification.

To a solution of the crude product of di-tert-butyl (1S)-{1-[(5-amino-1-methyl-1H-pyrazol-4-yl)carbamoyl]pentamethylene}biscarbamate and triethylamine (0.91 g) in chloroform (30 ml) was added triphenylmethyl chloride (2.51 g), and the mixture was stirred at room temperature for 6 hours. The reaction mixture was washed successively with 0.10% aqueous citric acid solution, brine and saturated aqueous sodium hydrogencarbonate solution. The organic layer was dried over anhydrous magnesium sulfate, filtered and concentrated in vacuo. The residue was purified by column chromatography on silica gel eluting with 3% methanol/chloroform to give di-tert-butyl (1S)-(1-{[1-methyl-5-(tritylamino)-1H-pyrazol-4-yl]carbamoyl}pentamethylene)biscarbamate (4.23 g) as an oil.

$^1$H-NMR(CDCl$_3$) δ 1.27–1.32 (2H, m), 1.42 (9H, s), 1.44 (9H, s), 1.46–1.63 (4H, m), 2.94 (3H, s), 3.09–3.10 (2H, m), 3.74–3.76 (1H, m), 4.56 (1H, br), 4.58 (1H, br), 4.97 (1H, br), 6.73 (1H, br), 7.20–7.31 (15H, m), 7.54 (1H, s)

EXAMPLE 21

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.36 g) in N,N-dimethylformamide (4.0 ml) was added N-(trimethylsilyl)acetamide (1.31 g) and the mixture was stirred at room temperature for 30 minutes. To the solution was added potassium iodide (465 mg) and the mixture was stirred at room temperature for 30 minutes. To the reaction mixture was added di-tert-butyl (1S)-(1-{[1-methyl-5-(tritylamino)-1H-pyrazol-4-yl]carbamoyl}pentamethylene)biscarbamate (1.37 g), and the whole mixture was stirred at 40° C. for 2 hours. To the resulting reaction mixture was added ethyl acetate (150 ml) and the solution was washed successively with brine (80 ml), 10% aqueous sodium trifluoroacetate solution (80 ml) and brine (80 ml), dried over anhydrous magnesium sulfate and filtered. The filtrate was concentrated to about 10 ml in vacuo. The concentrate was poured into diisopropyl ether (150 ml) and the resulting precipitate was collected by filtration and dried in vacuo. To a solution of the solid in methylene chloride (4.5 ml) were added anisole (1.5 ml) and trifluoroacetic acid (4.5 ml). The resulting solution was stirred at room temperature for 6 hours and poured into diisopropyl ether (150 ml). The resulting precipitate was collected by filtration and dried in vacuo to give a crude product (1.27 g), which was purified by preparative HPLC utilizing ODS column. The eluate containing a desired product was concentrated to about 20 ml in vacuo. The concentrate was further purified by preparative HPLC utilizing ODS column eluting with 15% acetonitrile/water. The eluate was concentrated to about 10 ml in vacuo and 0.05 mol/l sulfuric acid (3.64 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-[(2S)-(2,6-diaminohexanoyl)amino]-2-methyl-1-pyrazolio]methyl-3-cephem-4-carboxylic acid hydrogensulfate (166.4 mg) as an amorphous solid.

$^1$H-NMR(D$_2$O) δ 1.49–1.57 (2H, m), 1.61 (6H, d, J=3.2 Hz), 1.71–1.78 (2H, m), 1.95–2.09 (2H, m), 3.02 (2H, t, J=7.8 Hz), 3.23 (1H, d, J=17.9 Hz), 3.47 (1H, d, J=17.9 Hz), 3.74 (3H, s), 4.23 (1H, t, J=6.4 Hz). 5.01 (1H, d, J=16.0 Hz), 5.25 (1H, d, J=16.0 Hz), 5.25 (1H, d, J=5.0 Hz), 5.86 (1H, d, J=5.0 Hz), 8.13 (1H, s)

PREPARATION 56

To a solution of 5-amino-1-methyl-1H-pyrazole-4-carboxylic acid (7.1 g), N-(2-aminoethyl)tritylamine (15.1 g) and triethylamine (10.1 g) in chloroform (200 ml) was added N-(3-dimethylaminopropyl)-N'-ethylcarbodiimide hydrochloride (9.6 g), and the mixture was stirred at room temperature for 16 hours. The reaction mixture was washed successively with 10% aqueous citric acid solution, brine and saturated aqueous sodium hydrogencarbonate solution. The organic layer was dried over anhydrous sodium sulfate, filtered and concentrated in vacuo. The residue was triturated with ethyl acetate and dried in vacuo to give 5-amino-1-methyl-N-[2-(tritylamino)ethyl]-1H-pyrazole-4-carboxamide (11.4 g) as a solid.

$^1$H-NMR(CDCl$_3$) δ 2.35–2.38 (2H, m), 3.45–3.49 (2H, m), 3.63 (3H, s), 5.15 (1H, br), 5.91 (1H, br), 7.17–7.49 (16H, m)

PREPARATION 57

To a suspension of lithium aluminium hydride (3.78 g) in tetrahydrofuran (150 ml) was added 5-amino-1-methyl-N-[2-(tritylamino)ethyl]-1H-pyrazole-4-carboxamide (10.64 g) at room temperature. The mixture was stirred under reflux for 18 hours. After cooling on an ice bath, to the reaction mixture were added sodium fluoride (20 g) and aqueous tetrahydrofuran solution (10 ml). The insoluble materials were removed by filtration. The resulting filtrate was concentrated in vacuo, and the residue was dissolved in chloroform. The solution was washed with 10% aqueous sodium hydroxide solution. The organic layer was dried over anhydrous magnesium sulfate, filtered and concentrated in vacuo. The oily residue was triturated with ethyl acetate and dried in vacuo to give N-[(5-amino-1-methyl-1H-pyrazol-4-yl)methyl]-N'-tritylethane-1,2-diamine (3.2 g) as a solid.

$^1$H-NMR(CDCl$_3$) δ 2.45 (2H, br), 2.68 (2H, br), 3.34 (3H, s), 3.71 (2H, s), 6.94 (1H, br), 7.09–7.40 (16H, m)

PREPARATION 58

To a solution of N-[(5-amino-1-methyl-1H-pyrazol-4-yl)methyl]-N'-tritylethane-1,2-diamine (7.50 g) and triethylamine (2.86 g) in chloroform (100 ml) was added di-tert-butyl ({[(trifluoromethyl)sulfonyl]imino}-methylene)biscarbamate (11.05 g). The mixture was stirred at room temperature for 4 days. The reaction mixture was washed successively with 10% aqueous citric acid solution and brine, and the organic layer was dried over anhydrous magnesium sulfate, filtered and concentrated in vacuo. The residue was purified by column chromatography on silica gel eluting with 3% methanol/chloroform to give N-[(5-amino-1-methyl-1H-pyrazol-4-yl)methyl]-N',N"-bis(tert-butoxycarbonyl)-N-[2-(tritylamino)ethyl]guanidine (3.00 g) as a solid.

$^1$H-NMR(CDCl$_3$) δ 1.42 (9H, brs), 1.51 (9H, brs), 2.42–2.46 (2H, m), 3.30–3.34 (2H, m), 3.57 (3H, s), 4.08 (2H, s), 5.34 (1H, brs), 6.96 (1H, s), 7.21–7.41 (15H, m), 10.54 (1H, br)

PREPARATION 59

To a solution of N-[(5-amino-1-methyl-1H-pyrazol-4-yl)methyl]-N',N"-bis(tert-butoxycarbonyl)-N-[2-(tritylamino)ethyl]guanidine (1.84 g) in pyridine (10 ml) was added triphenylmethyl chloride (0.94 g), and the mixture was stirred at room temperature for 3 hours. To the reaction mixture was added chloroform (50 ml). The mixture was washed successively with 10% aqueous citric acid solution, brine and saturated aqueous sodium hydrogencarbonate solution. The organic layer was dried over anhydrous magnesium sulfate, filtered and concentrated in vacuo. The residue was purified by column chromatography on silica gel eluting with 3% methanol/chloroform to give N',N"-bis(tert-butoxycarbonyl{-N-([1-methyl-5-(tritylamino)-1H-pyrazol-4-yl]methyl}-N-[2-(tritylamino)ethyl]guanidine (1.60 g) as a solid.

$^1$H-NMR(CDCl$_3$) δ 1.32 (9H, s), 1.41 (9H, s), 2.25–2.45 (4H, m), 2.71 (3H, s), 3.35 (1H, brs), 3.59 (2H, s), 5.97 (1H, br), 7.06 (1H, s), 7.18–7.41 (30H, m), 10.21 (1H, br)

EXAMPLE 22

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.36 g) in N,N-dimethylformamide (4.0 ml) was added N-(trimethylsilyl)acetamide (1.31 g) and the mixture was stirred at room temperature for 30 minutes. To the solution was added potassium iodide (465 mg) and the mixture was stirred at room temperature for 30 minutes. To the reaction mixture was added N',N"-bis(tert-butoxycarbonyl)-N-{[1-methyl-5-(tritylamino)-1H-pyrazol-4-yl]methyl}-N-[2-(tritylamino)ethyl]guanidine (1.60 g), and the whole mixture was stirred at 40° C. for 4 hours. To the resulting reaction mixture was added ethyl acetate (150 ml) and the solution was washed successively with brine (80 ml), 10% aqueous sodium trifluoroacetate solution (80 ml) and brine (80 ml), dried over anhydrous magnesium sulfate and filtered. The filtrate was concentrated to about 10 ml in vacuo. The concentrate was poured into diisopropyl ether (150 ml) and the resulting precipitate was collected by filtration and dried in vacuo. To a solution of the solid in methylene chloride (6.0 ml) were added anisole (2.0 ml) and trifluoroacetic acid (6.0 ml). The resulting solution was stirred at room temperature for 6 hours and poured into diisopropyl ether (200 ml). The resulting precipitate was collected by filtration and dried in vacuo to give a crude product (1.40 g), which was purified by preparative HPLC utilizing ODS column. The eluate containing a desired product was concentrated to about 20 ml in vacuo. The concentrate was further purified by preparative HPLC utilizing ODS column eluting with 15% acetonitrile/water. The eluate was concentrated to about 10 ml in vacuo and 0.05 mol/l sulfuric acid (2.0 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-{[1-(2-aminoethyl)guanidino]methyl}-2-methyl-1-pyrazolio]methyl-3-cephem-4-carboxylic acid hydrogensulfate (61.9 mg) as an amorphous solid.

$^1$H-NMR(D$_2$O) δ 1.62 (6H, d, J=3.2 Hz), 3.26 (1H, d, J=17.9 Hz), 3.33 (2H, t, J=6.0 Hz), 3.54 (1H, d, J=17.9 Hz), 3.61 (2H, t, J=6.0 Hz), 3.72 (3H, s), 4.19 (2H, s), 5.01 (1H, d, J=15.6 Hz), 5.23 (1H, d, J=15.6 Hz), 5.27 (1H, d, J=5.0 Hz), 5.86 (1H, d, J=5.0 Hz), 8.09 (1H, s)

PREPARATION 60

A solution of diethyl 2-aminomalonate (1.68 g) and tert-butyl (2-aminoethyl)carbamate (3.20 g) in dehydrated chloroform (5 ml) was stirred under reflux. After 7 hours, additional tert-butyl (2-aminoethyl)carbamate (3.20 g) was added to the reaction mixture, and the mixture was stirred under reflux for 2 days. To the reaction mixture was added water, and the solution was washed with a mixed solvent of hexane and diisopropyl ether (1:1). The aqueous layer was extracted with methylene chloride. The organic layer was washed with water and extracted with 5% aqueous citric acid solution. The aqueous layer was washed with diethyl ether and basified with sodium hydroxide. The aqueous solution was extracted with methylene chloride. The organic layer was washed with brine, dried over anhydrous sodium sulfate, filtered and concentrated in vacuo. The residue was triturated with a mixed solvent of diisopropyl ether and diethyl ether to give di-tert-butyl 7-amino-6,8-dioxo-2,5,9,12-tetraazatridecanedioate (1.87 g) as a solid.

$^1$H-NMR(CDCl$_3$) δ 1.44 (18H, s), 2.19 (2H, br), 3.1–3.5 (8H, m), 4.00 (1H, s), 4.94 (2H, br), 8.01 (2H, br)

PREPARATION 61

To a suspension of phenyl N-[1-methyl-5-(tritylamino)-1H-pyrazol-4-yl]carbamate (949 mg) and di-tert-butyl 7-amino-6,8-dioxo-2,5,9,12-tetraazatridecanedioate (968 mg) in dehydrated chloroform (4 ml) was added N-ethyldiisopropylamine (0.342 ml), and the mixture was stirred under reflux for 5 hours. To the reaction mixture was added diethyl ether. The resulting precipitate was collected by filtration and dried in vacuo to give di-tert-butyl 7-[({[1-methyl-5-(tritylamino)-1H-pyrazol-4-yl]amino}carbonyl)amino]-6,8-dioxo-2,5,9,12-tetraazatridecanedioate (1.38 g) as a solid.

$^1$H-NMR(CDCl$_3$) δ 1.42 (18H, s), 2.93 (3H, s), 3.2–3.3 (4H, m), 3.3–3.4 (4H, m), 4.68 (1H, d, J=4.1 Hz), 5.63 (1H, br), 7.1–7.4 (15H, m), 7.36 (1H, br), 7.43 (1H, brs)

EXAMPLE 23

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (681 mg) in N,N-dimethylformamide (2 ml) was added N-(trimethylsilyl)acetamide (656 mg) and the mixture was stirred at room temperature for 30 minutes. To the solution was added potassium iodide (232 mg) and the mixture was stirred at room temperature for 55 minutes. To the reaction mixture was added a solution of di-tert-butyl 7-[({[1-methyl-5-(tritylamino)-1H-pyrazol-4-yl]amino}carbonyl)amino]-6,8-dioxo-2,5,9,12-tetraazatridecanedioate (784 mg) in N,N-dimethylformamide (2 ml), and the whole mixture was stirred at 45–50° C. for 3 hours and then at 50–55° C. for 1 hour. To the resulting reaction mixture was added ethyl acetate (50 ml) and the solution was washed successively with water (50 ml×2), 10% aqueous sodium trifluoroacetate solution (50 ml) and brine (50 ml), dried over anhydrous sodium sulfate and filtered. The filtrate was concentrated to about 5.5 g in vacuo. The concentrate was poured into diisopropyl ether (80 ml) and the resulting precipitate was collected by filtration and dried in vacuo. To a solution of the solid in methylene chloride (3 ml) were added anisole (1 ml) and trifluoroacetic acid (3 ml). The resulting solution was stirred at room temperature for 4 hours and poured into diisopropyl ether (80 ml). The resulting precipitate was collected by filtration and dried in vacuo to give a crude product (810 mg), which was purified by preparative HPLC utilizing ODS column. The eluate containing a desired product was concentrated to about 20 ml in vacuo. The concentrate was further purified by preparative HPLC utilizing ODS column eluting with 12% acetonitrile/water. The eluate was concentrated to about 10 ml in vacuo and 0.05M sulfuric acid (2.28 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-{[({1,3-bis[(2-aminoethyl)amino]-1,3-dioxopropan-2-yl}amino)carbonyl]amino}-2-methyl-1-pyrazolio]methyl-3-cephem-4-carboxylic acid hydrogensulfate (98 mg) as an amorphous solid.

$^1$H-NMR(D$_2$O) δ 1.61 (3H, s), 1.61 (3H, s), 3.18 (4H, t, J=5.7 Hz), 3.22 (1H, d, J=17.9 Hz), 3.49 (1H, d, J=17.9 Hz), 3.4–3.7 (4H, m), 3.72 (3H, s), 5.02 (1H, s), 5.08 (1H, d, J=16.0 Hz), 5.23 (1H, d, J=16.0 Hz), 5.26 (1H, d, J=5.0 Hz), 5.87 (1H, d, J=5.0 Hz), 7.95 (1H, s)

PREPARATION 62

To a suspension of 1-methyl-N$^5$-trityl-1H-pyrazole-4,5-diamine 1.60 g) in ethanol (50 ml) were added triethylamine (0.627 ml) and diethyl squarate (0.858 ml), and the mixture was stirred at room temperature for 22 hours. To the reaction mixture were added ethyl acetate (200 ml) and hexane (100 ml), and the solution was washed successively with water, 5% aqueous citric acid solution and brine. The organic layer was dried over anhydrous sodium sulfate, filtered and concentrated in vacuo. The crystalline residue was washed with diethyl ether and dried in vacuo to give 3-ethoxy-4-{[1-methyl-5-(tritylamino)-1H-pyrazol-4-yl]amino}-3-cyclobutene-1,2-dione (1.45 g) as a solid.

$^1$H-NMR(CDCl$_3$) δ 1.42 (3H, br), 2.99 (3H, s), 4.41 (1H, brs), 4.69 (2H, q, J=7.2 Hz), 6.40 (1H, br), 7.13–7.35 (16H, m)

PREPARATION 63

To a solution of di-tert-butyl [iminobis(2,1-ethanediyl)] biscarbamate (2.13 g) and 3-ethoxy-4-{[1-methyl-5-(tritylamino)-1H-pyrazol-4-yl]amino}-3-cyclobutene-1,2-dione (1.91 g) in chloroform (10 ml) was added triethylamine (0.558 ml), and the mixture was stirred under reflux. After 9 hours, additional di-tert-butyl [iminobis(2,1-ethanediyl)] biscarbamate (1.82 g) was added to the reaction mixture, and the mixture was stirred under reflux for 1 day. To the reaction mixture was added diethyl ether, and the solution was washed successively with 5% aqueous citric acid solution, water and brine. The organic layer was dried over anhydrous sodium sulfate, filtered and concentrated in vacuo. The residue was chromatographed on silica gel eluting with methylene chloride/methanol (20:1) to give di-tert-butyl {[(2-{[1-methyl-5-(tritylamino)-1H-pyrazol-4-yl]amino}-3,4-dioxocyclobut-1-en-1-yl)imino]bis(2,1-ethanediyl)}biscarbamate (1.84 g) as a solid.

$^1$H-NMR(CDCl$_3$) δ 1.39 (18H, s), 2.85 (3H, s), 3.0–3.2 (4H, m), 3.3–3.5 (2H, m), 3.7–3.9 (2H, m), 5.10 (1H, br), 5.16 (1H, br), 5.28 (1H, s), 7.1–7.4 (16H, m), 8.93 (1H, brs)

EXAMPLE 24

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (817 mg) in N,N-dimethylformamide (2.4 ml) was added N-(trimethylsilyl)acetamide (788 mg) and the mixture was stirred at room temperature for 30 minutes. To the solution was added potassium iodide (279 mg) and the mixture was stirred at room temperature for 30 minutes. To the reaction mixture was added a solution of di-tert-butyl {[(2-{[1-methyl-5-(tritylamino)-1H-pyrazol-4-yl]amino}-3,4-dioxocyclobut-1-en-1-yl)imino]bis(2,1-ethanediyl)}biscarbamate (883 mg) in N,N-dimethylformamide (1.8 ml), and the whole mixture was stirred at 45–50° C. for 3 hours and then at 50–55° C. for 3 hours. To the resulting reaction mixture was added ethyl acetate (50 ml) and the solution was washed successively with water (50 ml×2), 10% aqueous sodium trifluoroacetate solution (50 ml) and brine (50 ml), dried over anhydrous sodium sulfate and filtered. The filtrate was concentrated to about 8 g in vacuo. The concentrate was poured into diisopropyl ether (80 ml) and the resulting precipitate was collected by filtration and dried in vacuo. To a solution of the solid in methylene chloride (4.1 ml) were added anisole (1.36 ml) and trifluoroacetic acid (4.1 ml). The resulting solution was stirred at room temperature for 4 hours and poured into diisopropyl ether (100 ml). The resulting precipitate was collected by filtration and dried in vacuo to give a crude product (1.11 g), which was purified by preparative HPLC utilizing ODS column. The eluate containing a desired product was concentrated to about 20 ml in vacuo. The concentrate was further purified by preparative HPLC utilizing ODS column eluting with 10% acetonitrile/0.1% aqueous trifluoroacetic acid solution. The eluate (265 ml) was concentrated to about 10 ml in vacuo and lyophilized to give 7β-[(Z)-2-(5-amino-1,2,4-thiadiazol-3-yl)-2-(1-carboxy-1-methylethoxyimino)acetamido]-3-[3-amino-4-({2-[bis(2-aminoethyl)amino]-3,4-dioxo-1-cyclobuten-1-yl}amino)-2-methyl-1-pyrazolio]methyl-3-cephem-4-carboxylic acid trifluoroacetate (26 mg) as an amorphous solid.

$^1$H-NMR(D$_2$O) δ 1.62 (6H, s), 3.35 (1H, d, J=18.3 Hz), 3.40 (4H, t, J=6.0 Hz), 3.47 (2H, t, J=6.4 Hz), 3.73 (3H, s), 3.73 (1H, d, J=18.3 Hz), 3.9–4.1 (2H, m), 4.8–5.1 (1H, m), 5.12 (1H, d, J=15.1 Hz), 5.31 (1H, d, J=4.6 Hz), 5.83 (1H, d, J=4.6 Hz), 7.97 (1H, s)

PREPARATION 64

To a suspension of di-tert-butyl (2-amino-1,3-propanediyl)biscarbamate (810 mg) and 3-ethoxy-4-{[1-methyl-5-(tritylamino)-1H-pyrazol-4-yl]amino}-3-cyclobutene-1,2-dione (957 mg) in ethanol (10 ml) was added triethylamine (0.279 ml), and the mixture was stirred under reflux for 1 day. The reaction mixture was concentrated to about 5 ml in vacuo. To the concentrate was added diisopropyl ether. The precipitated crystals were collected by filtration and dried in vacuo to give di-tert-butyl {2-[(2-{[1-methyl-5-(tritylamino)-1H-pyrazol-4-yl]amino}-3,4-dioxocyclobut-1-en-1-yl)amino]-1,3-propanediyl}biscarbamate (1.22 g) as a solid.

$^1$H-NMR(DMSO-d$_6$) δ 1.37 (18H, s), 2.73 (3H, s), 2.9–3.3 (4H, m), 3.9–4.1 (1H, m), 5.84 (1H, br), 6.85 (2H, br), 7.07 (1H, brs), 7.1–7.3 (15H, m), 8.05 (1H, br)

EXAMPLE 25

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (817 mg) in N,N-dimethylformamide (2.4 ml) was added N-(trimethylsilyl)acetamide (788 mg) and the mixture was stirred at room temperature for 30 minutes. To the solution was added potassium iodide (279 mg) and the mixture was stirred at room temperature for 55 minutes. To the reaction mixture was added a solution of di-tert-butyl {2-[(2-{[1-methyl-5-(tritylamino)-1H-pyrazol-4-yl]amino}-3,4-dioxocyclobut-1-en-1-yl)amino]-1,3-propanediyl}biscarbamate (866 mg) in N,N-dimethylformamide (6.4 ml), and the whole mixture was stirred at 45–50° C. for 2.5 hours and then at 50–55° C. for 3 hours. To the resulting reaction mixture were added ethyl acetate (50 ml) and water (50 ml). After the precipitate was filtered off, the filtrate was separated. The organic layer was washed successively with water (50 ml), 10% aqueous sodium trifluoroacetate solution (50 ml) and brine (50 ml), dried over anhydrous sodium sulfate and filtered. The filtrate was concentrated to about 7 g in vacuo. The concentrate was poured into diisopropyl ether (80 ml) and the resulting precipitate was collected by filtration and dried in vacuo. To a solution of the solid in methylene chloride (3.4 ml) were added anisole (1.13 ml) and trifluoroacetic acid (3.4 ml). The resulting solution was stirred at room temperature for 4 hours and poured into diisopropyl ether (100 ml). The resulting precipitate was collected by filtration and dried in vacuo to give a crude product (902 mg), which was purified by preparative HPLC utilizing ODS column. The eluate containing a desired product was concentrated to about 20 ml in vacuo. The concentrate was further purified by preparative HPLC utilizing ODS column eluting with 8% acetonitrile/0.1% aqueous trifluoroacetic acid solution. The eluate (280 ml) was concentrated to about 10 ml in vacuo and lyophilized to give 7β-[(Z)-2-(5-amino-1,2,4-thiadiazol-3-yl)-2-(1-carboxy-1-methylethoxyimino)acetamido]-3-[3-amino-4-{[2-(1,3-diaminopropan-2-yl)amino-3,4-dioxo-1-cyclobuten-1-yl]amino}-2-methyl-1-pyrazolio]methyl-3-cephem-4-carboxylic acid trifluoroacetate (8.3 mg) as an amorphous solid.

$^1$H-NMR(D$_2$O) δ 1.62 (6H, s), 3.2–3.5 (5H, m), 3.6–3.8 (1H, m), 3.72 (3H, s), 4.6–5.0 (2H, m), 5.12 (1H, d, J=13.3 Hz), 5.31 (1H, d, J=4.6 Hz), 5.82 (1H, d, J=4.6 Hz), 8.04 (1H, s)

PREPARATION 65

To a solusion of 1,1'-oxalyldiimidazole (1.52 g) in N,N-dimethylformamide (16 ml) was added 1-methyl-N$^5$-trityl-1H-pyrazole-4,5-diamine (1.42 g) under ice-cooling, and the mixture was stirred at room temperature for 1 hour. To the reaction mixture was added a solution of di-tert-butyl [iminobis(2,1-ethanediyl)]biscarbamate (4.55 g) in N,N-dimethylformamide (4 ml) under ice-cooling, and the mixture was stirred at room temperature for 1 day and then allowed to stand at room temperature for 9 days. To the reaction mixture were added ethyl acetate (50 ml) and methylene chloride (20 ml). The resulting precipitate was collected by filtration and dried in vacuo to give di-tert-butyl [({2-[1-methyl-5-(tritylamino)-1H-pyrazol-4-yl]-2-oxoacetyl}imino)bis(2,1-ethanediyl)]biscarbamate (1.79 g) as a solid. The mother liquor was washed successively with water, 5% aqueous citric acid solution and brine. The organic layer was dried over anhydrous sodium sulfate, filtered and concentrated in vacuo. The crystalline residue was washed with a mixed solvent of methylene chloride and diethyl ether, dried in vacuo and combined with the former solid to give di-tert-butyl [({2-[1-methyl-5-(tritylamino)-1H-pyrazol-4-yl]-2-oxoacetyl}imino)bis(2,1-ethanediyl)]biscarbamate (2.44 g).

$^1$H-NMR(CDCl$_3$) δ 1.37 (9H, s), 1.45 (9H, s), 2.97 (3H, s), 3.2–3.4 (4H, m), 3.4–3.6 (2H, m), 3.78 (2H, t, J=6.2 Hz), 4.53 (1H, brs), 5.09 (1H, br), 5.34 (1H, br), 7.1–7.4 (15H, m), 7.49 (1H, s), 8.13 (1H, brs)

EXAMPLE 26

To a solution of 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (1.36 g, 2.00 mmol) in N,N-dimethylformamide (4 ml) was added N-(trimethylsilyl)acetamide (1.31 g) and the mixture was stirred at room temperature for 30 minutes. To the solution was added potassium iodide (465 mg) and the mixture was stirred at room temperature for 40 minutes. To the reaction mixture was added a solution of di-tert-butyl [({2-[1-methyl-5-(tritylamino)-1H-pyrazol-4-yl]-2-oxoacetyl}imino)bis(2,1-ethanediyl)]biscarbamate (1.42 g) in N,N-dimethylformamide (6 ml), and the whole mixture was stirred at 45–50° C. for 3 hours and then at 50–55° C. for 1 hour. To the resulting reaction mixture was added ethyl acetate (100 ml) and the solution was washed successively with water (100 ml×2), 10% aqueous sodium trifluoroacetate solution (100 ml) and brine (50 ml), dried over anhydrous sodium sulfate and filtered. The filtrate was concentrated to about 9 g in vacuo. The concentrate was poured into diisopropyl ether (150 ml) and the resulting precipitate was collected by filtration and dried in vacuo. To a solution of the solid in methylene chloride (4.8 ml) were added anisole (1.6 ml) and trifluoroacetic acid (4.8 ml). The resulting solution was stirred at room temperature for 4 hours and poured into diisopropyl ether (150 ml). The resulting precipitate was collected by filtration and dried in vacuo to give a crude product (1.24 g), which was purified by preparative HPLC utilizing ODS column. The eluate containing a desired product was concentrated to about 20 ml in vacuo. The concentrate was further purified by preparative HPLC utilizing ODS column eluting with 30% acetonitrile/water. The eluate was concentrated to about 10 ml in vacuo and 0.05M sulfuric acid (0.77 ml) was added. The resulting solution was lyophilized to give 7β-[(Z)-2-(5-amino-1,2,4-thiadiazol-3-yl)-2-(1-carboxy-1-methylethoxyimino)acetamido]-3-[3-amino-4-({2-[bis(2-aminoethyl)amino]-2-oxoacetyl}amino)-2-methyl-1-pyrazolio]methyl-3-cephem-4-carboxylic acid hydrogensulfate (30 mg) as an amorphous solid.

$^1$H-NMR(D$_2$O) δ 1.61 (6H, s), 3.24 (1H, d, J=17.9 Hz), 3.38 (2H, t, J=5.7 Hz), 3.41 (2H, t, J=6.4 Hz), 3.47 (1H, d, J=17.9 Hz), 3.48 (2H, t, J=6.4 Hz), 3.72 (2H, t, J=5.7 Hz), 3.75 (3H, s), 5.10 (1H, d, J=15.4 Hz), 5.26 (1H, d, J=5.0 Hz), 5.27 (1H, d, J=15.4 Hz), 5.87 (1H, d, J=5.0 Hz), 8.15 (1H, s)

This application is based on application No. 2003905084 filed in Australia on Sep. 18, 2003, the content of which is incorporated hereinto by reference.

The invention claimed is:

1. A compound of the formula [I]:

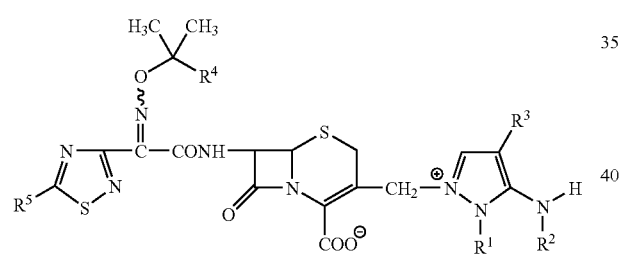

wherein
$R^1$ is lower alkyl or hydroxy(lower)alkyl, and
$R^2$ hydrogen or an amino protecting group selected from the group consisting of acyl, substituted or unsubstituted aryl(lower)alkylidene, and aryl(lower)alkyl, or
$R^1$ and $R^2$ are bonded together and form lower alkylene;
$R^3$ is -A-$R^6$
wherein
A is a bond, —NHCO—(CH$_2$CO)$_n$—, wherein n is 0 or 1, lower alkylene, —NH—CO—CO—, or

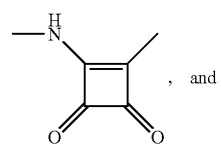

$R^6$ is

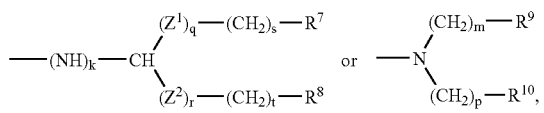

wherein
$Z^1$ and $Z^2$ are independently —NHCO— or —CONH—,
k, q and r are independently 0 or 1,
s and t are independently an integer of 0 to 6,
m and p are independently an integer of 0 to 6, and
$R^7$, $R^8$, $R^9$ and $R^{10}$ independently amino, amino protected with acyl, substituted or unsubstituted aryl(lower)alkylidene, or aryl(lower)alkyl, guanidino, guanidino protected with acyl, substituted or unsubstituted aryl(lower)alkylidene, or aryl(lower)alkyl, amidino or amidino protected with acyl, substituted or unsubstituted aryl(lower)alkylidene, or aryl(lower)alkyl;
$R^4$ is carboxy or esterified carboxy; and
$R^5$ is amino or amino protected with acyl, substituted or unsubstituted aryl(lower)alkylidene, or aryl(lower)alkyl;
or a pharmaceutically acceptable salt thereof.

2. The compound of claim 1, wherein
$R^1$ is lower alkyl or hydroxy(lower)alkyl, and
$R^2$ is hydrogen, aryl(lower)alkyl or acyl; or
$R^1$ and $R^2$ are bonded together and form lower alkylene;
$R^4$ is carboxy or esterified carboxy;
$R^5$ is amino, aryl(lower)alkylamino, or acylamino; and
$R^7$, $R^8$, $R^9$ and $R^{10}$ are independently amino, aryl(lower)alkylamino, acylamino, guanidino, acylguanidino, amidino or acylamidino;
or a pharmaceutically acceptable salt thereof.

3. The compound of claim 2, wherein
$R^1$ is lower alkyl or hydroxy(lower)alkyl, and
$R^2$ is hydrogen, aryl(lower)alkyl, lower alkanoyl or lower alkoxycarbonyl; or
$R^1$ and $R^2$ are bonded together and form lower alkylene;
$R^4$ is carboxy or lower alkoxycarbonyl;
$R^5$ is amino, aryl(lower)alkylamino, lower alkanoylamino or lower alkoxycarbonylamino; and
$R^7$, $R^8$, $R^9$ and $R^{10}$ are independently amino, aryl(lower)alkylamino, lower alkanoylamino, lower alkoxycarbonylamino, guanidino, 2,3-bis[(lower)alkoxycarbonyl]guanidino, amidino or $N^1,N^2$-bis[(lower)alkoxycarbonyl]amidino;
or a pharmaceutically acceptable salt thereof.

4. The compound of claim 3, wherein
$R^1$ is lower alkyl;
$R^2$ is hydrogen;
$R^4$ is carboxy;
$R^5$ is amino; and
$R^7$, $R^8$, $R^9$ and $R^{10}$ are amino;
or a pharmaceutically acceptable salt thereof.

5. The compound of claim 1, wherein
A is —NHCO—(CH$_2$CO)$_n$— wherein n is 0 or 1, and
$R^6$ is:

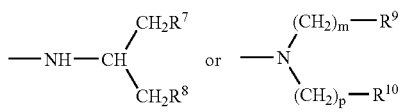

wherein m and p are independently an integer of 1 to 3, and
$R^7$, $R^5$, $R^9$ and $R^{10}$ are independently amino or amino protected by acyl, substituted or unsubstituted aryl(lower)alkylidene, or aryl(lower)alkyl;
or a pharmaceutically acceptable salt thereof.

6. The compound of claim 5, wherein
A is —NHCO—, and
$R^7$, $R^8$, $R^9$ and $R^{10}$ are amino;
or a pharmaceutically acceptable salt thereof.

7. The compound of claim 1, wherein
A is:
—NHCO—$(CH_2CO)_n$—, wherein n is 0 or 1,
—NH—CO—CO—, or

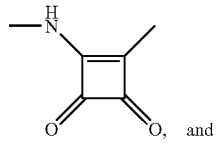

, and $R^6$ is:

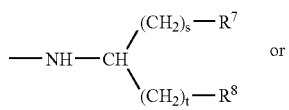 or

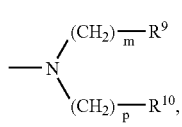, wherein s, t, m and p are independently an integer of 1 to 6, and
$R^7$, $R^8$, $R^9$ and $R^{10}$ are amino or amino protected by acyl, substituted or unsubstituted aryl(lower)alkylidene, or aryl(lower)alkyl;
or a pharmaceutically acceptable salt thereof.

8. The compound of claim 1, wherein
A is bond or —NHCO—, and
$R^6$ is:

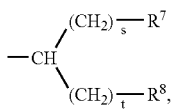, wherein s, t, $R^7$ and $R^8$ are each as defined in claim 1;
or a pharmaceutically acceptable salt thereof.

9. The compound of claim 8, wherein
A is —NHCO—, and
$R^7$ and $R^8$ are independently amino or guanidino;
or a pharmaceutically acceptable salt thereof.

10. The compound of claim 1, wherein
A is lower alkylene, and
$R^6$ is:

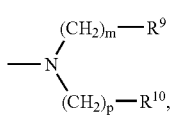, wherein m and p are each as defined in claim 1, and
$R^9$ and $R^{10}$ are independently amino or amidino;
or a pharmaceutically acceptable salt thereof.

11. The compound of claim 1, wherein
A is —NHCO— and
$R^6$ is:

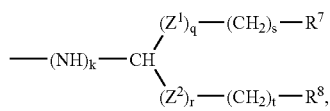, wherein
$Z^1$, $Z^2$, k, q and r are each as defined in claim 1,
s and t are independently an integer of 1 to 6, and
$R^7$ and $R^8$ are amino;
or a pharmaceutically acceptable salt thereof.

12. The compound of claim 1, which is selected from the group consisting of:
7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylate, 7β-[(Z)-2-(5-amino-1,2,4-thiadiazol-3-yl)-2-(1-carboxy-1-methylethoxyimino)acetamido]-3-{3-amino-4-({[bis(2-aminoethyl)amino]carbonyl}amino)-2-methyl-1-pyrazolio}methyl-3-cephem-4-carboxylic acid hydrogensulfate, 7β-[(Z)-2-(5-amino-1,2,4-thiadiazol-3-yl)-2-(1-carboxy-1-methylethoxyimino)acetamido]-3-[3-amino-4-({[N-(2-aminoethyl)-N-(3-aminopropyl)amino]carbonyl}amino)-2-methyl-1-pyrazolio]methyl-3-cephem-4-carboxylate, 7β-[(Z)-2-(5-amino-1,2,4-thiadiazol-3-yl)-2-(1-carboxy-1-methylethoxyimino)acetamido]-3-(3-amino-4-{3-[2-amino-1-(aminomethyl)ethyl]ureido}-2-methyl-1-pyrazolio)methyl-3-cephem-4-carboxylic acid hydrogensulfate, and 7β-[(Z)-2-(5-amino-1,2,4-thiadiazol-3-yl)-2-(1-carboxy-1-methylethoxyimino)acetamido]-3-{3-amino-4-[(3-{[2-amino-1-(aminomethyl)ethyl]amino}-3-oxopropanoyl)amino]-2-methyl-1-pyrazolio}methyl-3-cephem-4-carboxylate; or
a pharmaceutically acceptable salt thereof.

13. A process for preparing a compound of the formula [I]:

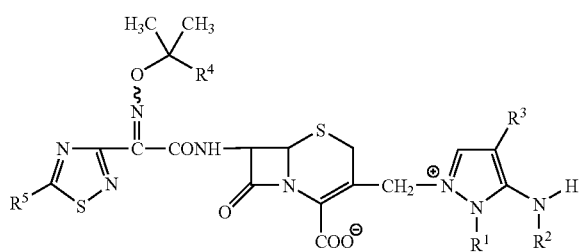

[I]

wherein
$R^1$ is lower alkyl or hydroxy(lower)alkyl, and
$R^2$ is hydrogen or amino protecting group which is acyl, substituted or unsubstituted aryl(lower)alkylidene, or aryl(lower)alkyl, or $R^1$ and $R^2$ are bonded together and form lower alkylene;
$R^3$ is -A-$R^6$
wherein
A is:
a bond,
—NHCO—$(CH_2CO)_n$—, wherein n is 0 or 1, lower alkylene,
—NH—CO—CO—, or

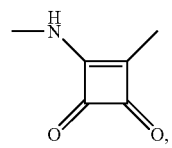

and $R^6$ is:

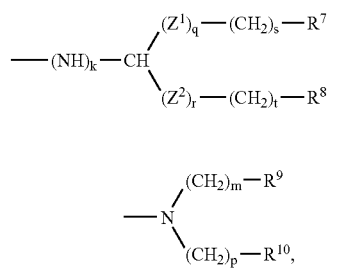

wherein
$Z^1$ and $Z^2$ are independently —NHCO— or —CONH—,
k, q and r are independently 0 or 1,
s and t are independently an integer of 0 to 6,
m and p are independently an integer of 0 to 6, and
$R^7$, $R^8$, $R^9$ and $R^{10}$ are independently amino, amino protected by acyl, substituted or unsubstituted aryl (lower)alkylidene, or aryl(lower)alkyl, guanidino, guanidino protected by acyl, substituted or unsubstituted aryl(lower)alkylidene, or aryl(lower)alkyl, amidino or amidino protected by acyl, substituted or unsubstituted aryl(lower)alkylidene, or aryl(lower)alkyl;
$R^4$ is carboxy or esterified carboxy; and
$R^5$ is amino or amino protected by acyl, substituted or unsubstituted aryl(lower)alkylidene, or aryl(lower)alkyl;
or a salt thereof;
said method comprising:
(1) reacting a compound of the formula [II]:

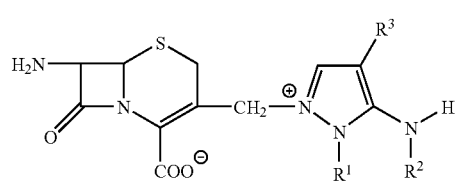

wherein $R^1$, $R^2$ and $R^3$ are each as defined above, or its reactive derivative at the amino group, or a salt thereof, with a compound of the formula [III]:

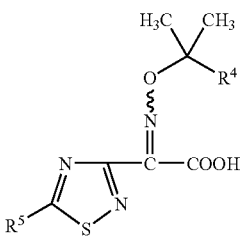

wherein $R^4$ and $R^5$ are each as defined above, or its reactive derivative at the carboxy group, or a salt thereof to give a compound of the formula [I]:

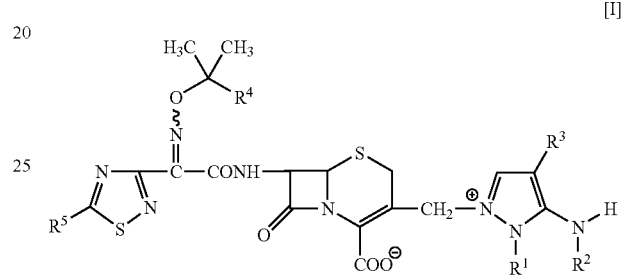

wherein $R^1$, $R^2$, $R^3$, $R^4$ and $R^5$ are each as defined above, or a salt thereof, or
(2) subjecting a compound of the formula [Ia]:

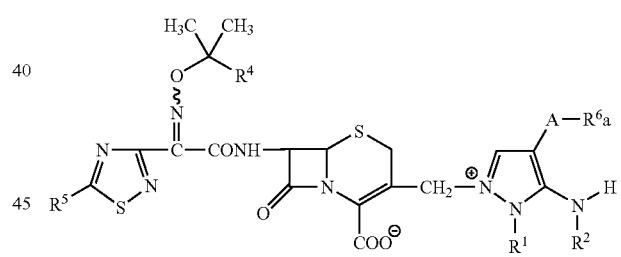

wherein $R^1$, $R^2$, $R^4$, $R^5$ and A are each as defined above, and $R^6$a is

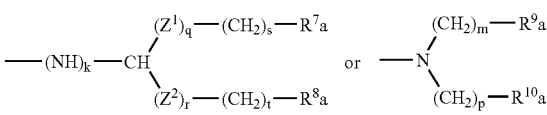

wherein $Z^1$, $Z^2$, k, q, r, s, t, m and p are each as defined above, and $R^7$a, $R^8$a, $R^9$a and $R^{10}$a are independently protected amino, protected guanidino or protected amidino, which protected groups are protected by a group selected from the group consisting of acyl, substituted or unsubstituted aryl(lower)alkylidene, and aryl(lower)alkyl; or a salt thereof;

to an elimination reaction of the amino protecting group to give a compound of the formula [Ib]:

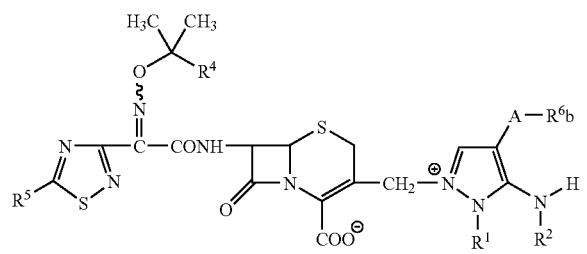

wherein
$R^1$, $R^2$, $R^4$, $R^5$ and A are each as defined above, and $R^6b$ is:

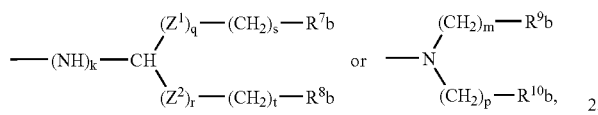

wherein $Z^1$, $Z^2$, k, q, r, s, t, m and p are each as defined above, and
$R^7b$, $R^8b$, $R^9b$ and $R^{10}b$ are independently amino, guanidino or amidino;
or a salt thereof; or (3) reacting a compound of the formula [VI]:

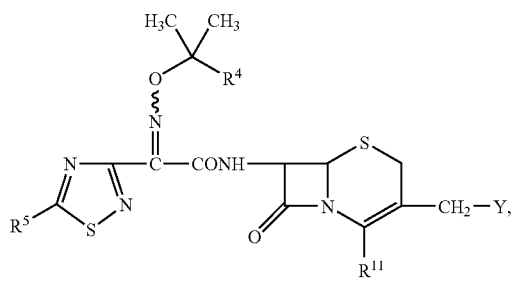

wherein $R^4$ and $R^5$ are each as defined above, $R^{11}$ is protected carboxy which is esterified carboxy, and
Y is a leaving group;
or a salt thereof;
with a compound of the formula [VII]:

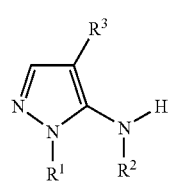

wherein $R^1$, $R^2$ and $R^3$ are each as defined above; or a salt thereof;

to give a compound of the formula [VIII]:

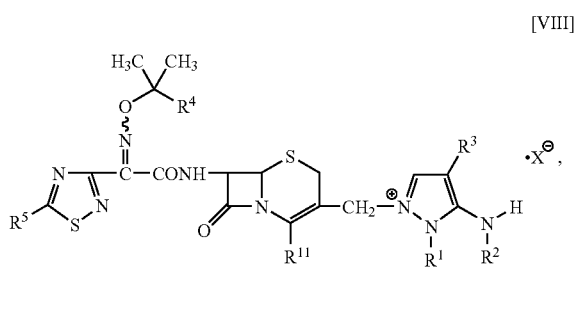

wherein $R^1$, $R^2$, $R^3$, $R^4$, $R^5$ and $R^{11}$ are each as defined above, and
$X^\ominus$ is an anion; or a salt thereof; and
subjecting the compound of the formula [VIII]; or a salt thereof;
to an elimination reaction of the carboxy protecting group, to give a compound of the formula [I]:

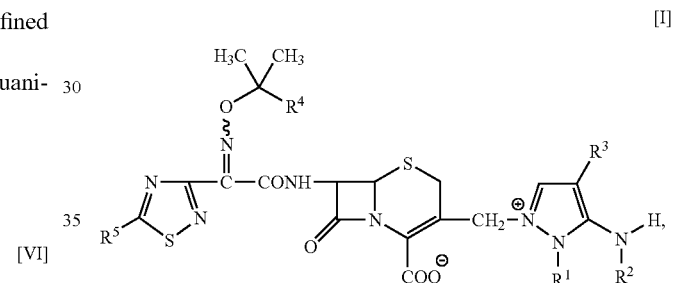

wherein $R^1$, $R^2$, $R^3$, $R^4$ and $R^5$ are each as defined above; or a salt thereof.

14. A pharmaceutical composition comprising:
the compound of claim 1 or a pharmaceutically acceptable salt thereof in admixture with a pharmaceutically acceptable carrier.

15. The composition of claim 14 in a form suitable for oral administration.

16. The composition of claim 14 in a form suitable for parenteral administration.

17. A method for making a medicament comprising admixing the compound of claim 1, or a pharmaceutically acceptable salt thereof, with a pharmaceutically acceptable carrier.

18. A method for the treatment of an infectious disease caused by a bacterium which comprises:
administering to a subject in need thereof the compound of claim 1, or a pharmaceutically acceptable salt thereof.

19. The method of claim 18, wherein said bacterium is a gram-negative bacterium.

20. The method of claim 18, wherein said bacterium is a gram-positive bacterium.

* * * * *